United States Patent [19]

Michaels et al.

[11] 4,434,660

[45] Mar. 6, 1984

[54] ULTRASONIC INSPECTION AND DEPLOYMENT APPARATUS

[75] Inventors: Jennifer E. Michaels; Thomas E. Michaels, both of Ithaca, N.Y.; Stephen J. Mech, Jr., Pasco, Wash.

[73] Assignee: The United States of America as represented by the United States Department of Energy, Washington, D.C.

[21] Appl. No.: 245,304

[22] Filed: Mar. 19, 1981

[51] Int. Cl.³ .................................................. G01N 29/04
[52] U.S. Cl. ........................................ 73/622; 73/619; 73/637; 73/638
[58] Field of Search .................. 73/622, 619, 625, 628, 73/634, 637, 638, 640, 641, 588

[56] References Cited

U.S. PATENT DOCUMENTS

| | | | |
|---|---|---|---|
| 3,382,707 | 5/1968 | Heselwood | 73/644 |
| 3,921,440 | 11/1975 | Toth | 73/622 |
| 3,930,404 | 1/1976 | Ryden | 73/622 |
| 3,983,374 | 9/1976 | Sorensen et al. | 73/619 |
| 4,114,456 | 9/1978 | Dury | 73/622 |
| 4,217,782 | 8/1980 | Pont | 73/637 |

*Primary Examiner*—Anthony V. Ciarlante
*Attorney, Agent, or Firm*—K. R. Bowers, Jr.; Z. L. Dermer

[57] ABSTRACT

An ultrasonic inspection apparatus for the inspection of metal structures, especially installed pipes.

The apparatus combines a specimen inspection element, an acoustical velocity sensing element, and a surface profiling element, all in one scanning head. A scanning head bellows contains a volume of oil above the pipe surface, serving as acoustical couplant between the scanning head and the pipe.

The scanning head is mounted on a scanning truck which is mobile around a circular track surrounding the pipe. The scanning truck has sufficient motors, gears, and position encoders to allow the scanning head six degrees of motion freedom.

A computer system continually monitors acoustical velocity, and uses that parameter to process surface profiling and inspection data. The profiling data is used to automatically control scanning head position and alignment and to define a coordinate system used to identify and interpret inspection data.

The apparatus is suitable for highly automated, remote application in hostile environments, particularly high temperature and radiation areas.

4 Claims, 17 Drawing Figures

45° INSPECTION WAVE

ULTRASONIC INSPECTION AND DEPLOYMENT APPARATUS

GOVERNMENT CONTRACT

This invention was conceived during performance of a contract with the United States Government, designated EY-76-C-14-2170.

BACKGROUND OF THE INVENTION

This application is substantially similar to a simultaneously filed application of identical title and inventive entity U.S. Pat. No. 245,426 now abandoned.

This invention relates to a deployment apparatus for the performance of a task on a specimen, especially ultrasonic inspection of metal structures and more especially ultrasonic inspection of piping and pipe welds located in high temperature and high radiation environments.

Since defects in metal and welds can lead to overall failure, routine inspections are required in many applications. Non-destructive inspection using ultrasonic waves is now well known art. The general principle teaches that an ultrasonic wave, introduced into a specimen, is reflected on encountering a change in acoustical impedance. Pores, cracks, and other defect types in metal strongly reflect sound waves, creating echoes.

Ultrasonic testing equipment introduces sound waves of frequency above 100,000 cycles per second into the specimen to be inspected and records on an oscilliscope style screen the pulses of echoes resulting. Informed analysis of the patterns on the screen allows identification of echoes which are created by the existence of a specific defect such as voids and material discontinuities. More sophisticated methods allow preparation of a pictorial representation of the specimen interior which also identifies defect locations and size.

Generation of an ultrasonic wave is most often done using a piezoelectric crystal to which an impulse voltage is applied. The crystal vibrates mechanically at its resonant frequency in response to the impulse applied, creating an ultrasonic wave. A piezoelectric crystal, if exposed to a mechanical vibration, will also function in reverse to generate a corresponding electrical voltage. Thus, a piezoelectric crystal may be used as a T-transducer; a transmitter of ultrasonic waves, or as an R-transducer; a receiver of ultrasonic waves. A single transducer, designated a TR transducer, may perform both roles by transmitting an ultrasonic pulse for several microseconds followed by several thousand microseconds sensitivity to incoming sound. A pair of transducers may be operated in association such that one "pitch" transducer transmits ultrasonic waves while the other "catch" transducer receives pitch waaves as well as any echoes.

High frequency sound waves propagate poorly in compressible fluids such as air. In the absence of affirmative contact between the transducer and the specimen, an incompressible couplant between the surfaces of these must be used to transmit sound waves therebetween. A film of oil, glycerine, or water or a solid wedge is the usual couplant.

Ultrasonic inspections characteristically require numerous test positions of the transducer with respect to the specimen in order to completely inspect all specimen areas. Movement of the transducer between test sites is a repetitious task, and generates voluminous data. A high degree of automation is desirable, especially if the specimen is located in a hostile environment.

Liquid metal fast breeder reactors have large installed pipes containing hot liquid sodium in radiation areas. Regulations proposed for breeder reactors may require routine weld inspections on specific pipes, with test failure criterion based on defect characteristics such as size.

While defect size is of interest in anticipating specimen failure, the time rate of growth of defects is of greater importance. The historical establishment of failure criterion based on defect characteristics measurable at a single point in time is considered a result of limitations of then-existing inspection art rather than attention to real failure modes. Since an installed pipe moves over time due to thermal expansion and other reasons, it is extremely difficult to inspect a given pore or crack twice, separated over a time interval of perhaps a year, in order to obtain defect growth data. A specific defect cannot be precisely relocated and data obtained once cannot be repeated. Consequently, current practice which bases failure criterion on defect size, can easily require repair of a defect, requiring expensive plant shutdown, which defect may in reality be unstressed and not propagating. Also, a small, but stressed crack which is actually growing, may be considered safe.

If an inspection apparatus capable of precise, repeatable inspection of specific defects could be developed, new inspection failure criterion could be developed which would be both safer and more economic.

Precise data repeatability over a time interval, which reveals defect growth, is of obvious importance to inspection of such specimens as aircraft wing supports. Of further importance to applicability to pipes in nuclear power plants is the degree of automation achievable.

Consequently, it is desired to provide a highly automated ultrasonic inspection apparatus, able to accurately repeat data scans, operable in high temperature and radiation environments and especially adapted to inspection of welds on large installed pipes.

SUMMARY OF THE INVENTION

The invention is an apparatus for ultrasonic inspection of a metal specimen combining several features which together make a high degree of data repeatability and automation feasible.

It is intended that an initial scan or inspection survey of the specimen will be obtained, perhaps prior to initial operation. During this scan, a profiling function of the apparatus discovers and stores the position of surface features of the specimen as well as positions of internal defects. Some surface features, such as reference holes or scratches may be deliberately introduced by the operator. The surface features are used by a computer to define a coordinate system. The computer then collects defect data during inspection scans which are repeatable in space defined by the surface-feature-based coordinate system. Consequently, future inspections, even years later, can relocate specific defects even if the entire specimen has shifted location, by computer recognition of the reference surface features.

The apparatus has a mechanical scanner track which permanently or temporarily attaches to a specimen. The mechanism has a sufficient number of axes of motion such that the scanner can be moved over the specimen surface.

A scanning head contains multiple ultrasonic transducer elements in a single housing to perform three functions: (1) surface profiling; (2) specimen inspection; and (3) couplant acoustic velocity sensing. A single TR transducer for surface profiling is used to measure the time-of-flight of the sound wave reflected off the specimen surface. Since the velocity of sound in the couplant is also monitored, the distance of the transducer housing to the specimen surface can be calculated and the surface features accurately mapped as position data. This data is stored for future use.

Additionally, the peak amplitude of the surface echo is measured and the entire scanning head tilted as necessary to maximize this echo, thereby ensuring optimum perpendicular alignment, if desired, of the scanning head with the surface. The surface profile information stored in a computer is used to automatically control the scanning head standoff distance during specimen inspection.

A pitch-catch transducer pair is used for specimen inspection.

A single TR transducer for velocity sensing is aimed at a reflector integral to the scanning head housing at a constant, known distance from this transducer. Sound from this transducer passes through a fixed length path through the couplant. The time-of-flight of the reflected wave from the reflector is used to calculate the speed of sound in the couplant.

The scanner head is equipped with a pliable bellows which bears against the specimen surface forming an enclosed volume between the specimen surface and the transducers in the scanner head. A uniform laminar flow of couplant is passed through the bellows volume such that acoustical communication between the transducers and the surface is maintained. The couplant itself is an oil chosen to be able to withstand the expected specimen temperature and chemically compatible with the environment.

The couplant containment means has an alternate arrangement described below, but both arrangements avoid a common problem generated by solid wedge type couplants which is the trapping of reflected waves under the wedge. A lack of wave trapping prevents there being a wide frequency range of meaningless noise such that the frequency content of echoes becomes useful data. The scanning device disclosed here utilizes frequency data and mathematical weighting thereof to discover the energy content of an echo using well-known techniques which greatly improve the applicability of the system to large-grained metal specimens often encountered in nuclear-grade piping.

The gathering of multiple transducer elements into a single housing is of significant advantage. The acoustical velocity in the couplant varies with couplant temperature which may vary between the locations of transducer elements used to measure acoustical velocity and transducers used for specimen inspection and surface profiling if these are separated. Such temperature variation would reduce the accuracy of the couplant acoustical velocity measurement with adverse effect on control and data acquisition functions. Also, installation of the surface profiling transducer in a common scanning head enables that device to establish perpendicularity between all transducers and the specimen surface, if so desired, and to eliminate reference errors that might result from changing transducers mounted in separate heads.

The apparatus has computerized control of the scanner mechanism allowing preprogrammed and operator initiated control of the scanner. Electronic feedback of information from the surface profiling function is used to adjust scanner head orientation and position during current scan operations.

From the above, it is seen that several features have been incorporated into the design of an ultrasonic inspection apparatus. The apparatus has a surface profiling element, a couplant acoustical velocity sensing element, and a specimen inspection element, all mounted in a common scanning head having a bellows-contained couplant volume. The apparatus has control mechanisms which use computer stored profile information and pattern recognition to automatically position and align the scanner head during specimen inspection. The apparatus control system automatically and repeatedly performs the specimen inspection using profile data. Finally, the apparatus has a scanning mechanism with degrees of motion freedom sufficient to permit coverage of the entire inspection area.

It is the combination of each of the above features together which enables the resulting apparatus to be best utilized for automatic, remote, repeatable inspection of specimens in hostile environments. Essentially all steps needed to position the scanner and acquire meaningful inspection data are automated such that the operator may be remotely located.

DESCRIPTION OF THE FIRST PREFERRED EMBODIMENT

The following detailed description relates to a first preferred embodiment which is the application of the apparatus to inspection of large diameter cylindrical installed pipe. The inventive concepts are also applicable to a metal specimen of other geometric shapes and sizes with necessary alterations to the mechanical system to accommodate whatever motion is necessary to closely scan an altered specimen geometry.

Figure 1:
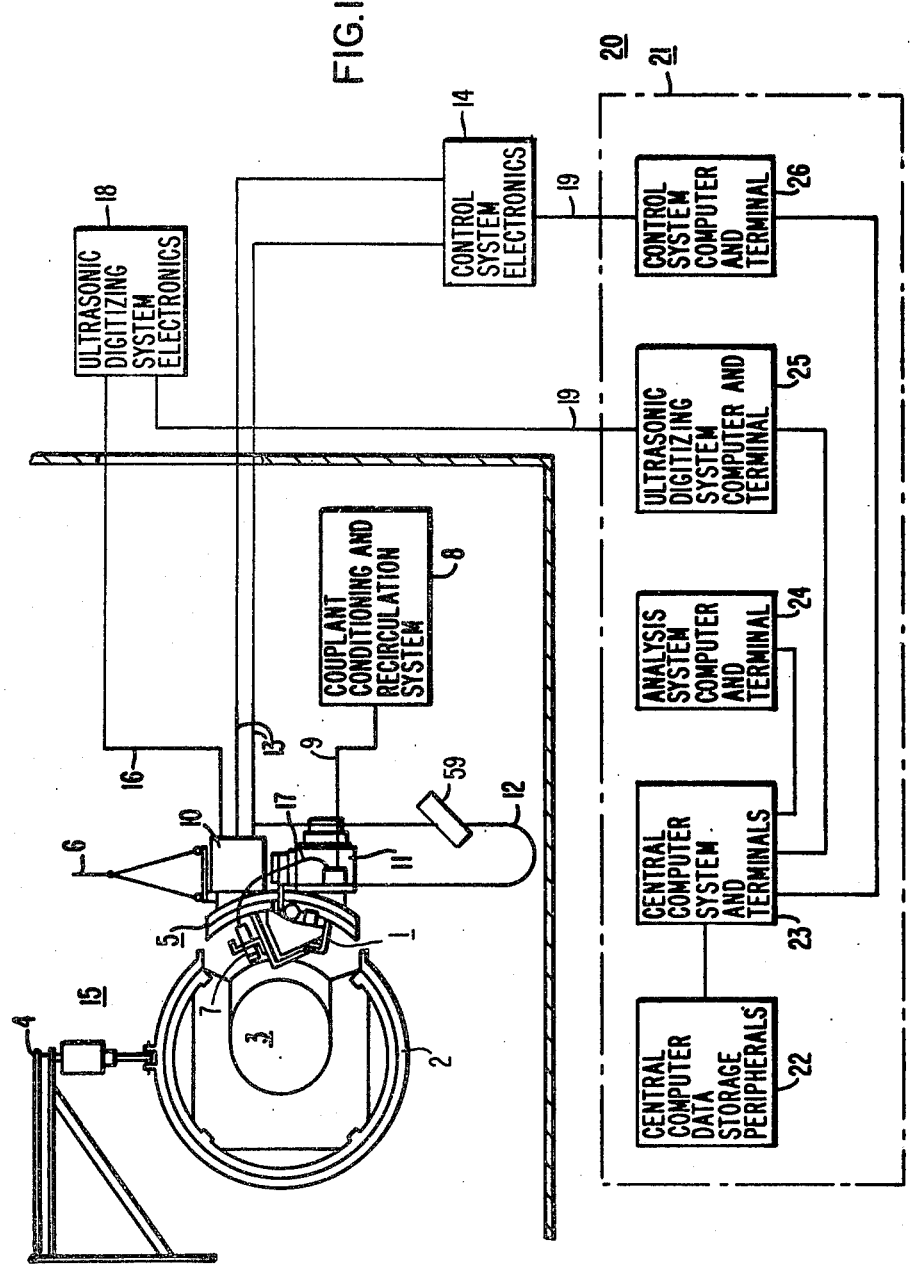
FIG. 1 is a schematic diagram of the complete ultrasonic inspection apparatus.

Referring to FIG. 1, the overall ultrasonic inspection apparatus has a scanning truck 1 mounted within a circular track 2 which surrounds and is supportively attached to a specimen pipe 3. Track 2 additionally has support means shown in FIG. 1 as a bracket 4. Track 2 has a removable section 5 shown in FIG. 1 as supported by a hoist 6 just prior to installation of removable section 5. Scanning truck 1 may be parked in the removable section 5 such that scanning truck 1 itself is removable along with removable section 5. Removable section 5 is of sufficient size to allow passage of the track 2 into circumscription around pipe 3.

The couplant supply to scanning head 7 is provided by a couplant conditioning and recirculation system 8 which includes couplant temperature control means. System 8 must be supplied with a sufficient reservoir of couplant or alternatively must have sumps to gather used couplant for recycle. The couplant itself must be an incompressible fluid, one suitable example being dimethyldiphenyl silicone fluid which is commercially available as GE-SE-1154. Hose 9 in FIG. 1 is intended to represent both couplant supply and return lines, while hose 17 represents scanning head 7 supply and return lines.

Removable track section 5 has an electrical junction box 10 attached thereto which remains in a fixed position with respect to track 2. A second junction box 11 is fixed to scanning truck 1 and consequently moves with scanning truck 1 around track 2. This movable junction box 11 supplies electrical and couplant fluid connections to scanning truck 1 and has flexible cable 12 spanning to junction box 10 of sufficient length to fully accommodate the necessary travel.

Scanning truck 1 will be shown hereinbelow to have multiple stepping motors, position encoders, and limit switches which are used to controllably move scanning truck 1 over the pipe 3 surface. Signal cables 13 are shown providing input and output signals to and from these components to a control panel 4 which is located outside cell 15, considered to be a hostile environment. Coaxial cable 16 transmits signals to and from the ultrasonic transducers in the scanning head 7 to a signal conditioning panel 18 where analog signals from the transducer are amplified and displayed. Cables 19 from these panels 14 and 18 may be grouped together for routing to a remote area 20 out of the hostile environment and perhaps to a mobile vehicle 21. This vehicle 21 is shown to contain a central computer 23 with a data storage peripheral 22, an analysis computer 24, a digitizing computer 25, and a control computer 26. The central computer 23 receives position information from control computer 26 and demands a preprogrammed sweep in time and space by scanner head 7 over the pipe 3 surface. Central computer 23 also receives scan data via digitizing computer 25 for analysis by analysis computer 24. Local control of scanning truck 1 is provided by a manual control pendant 59.

Figure 2:
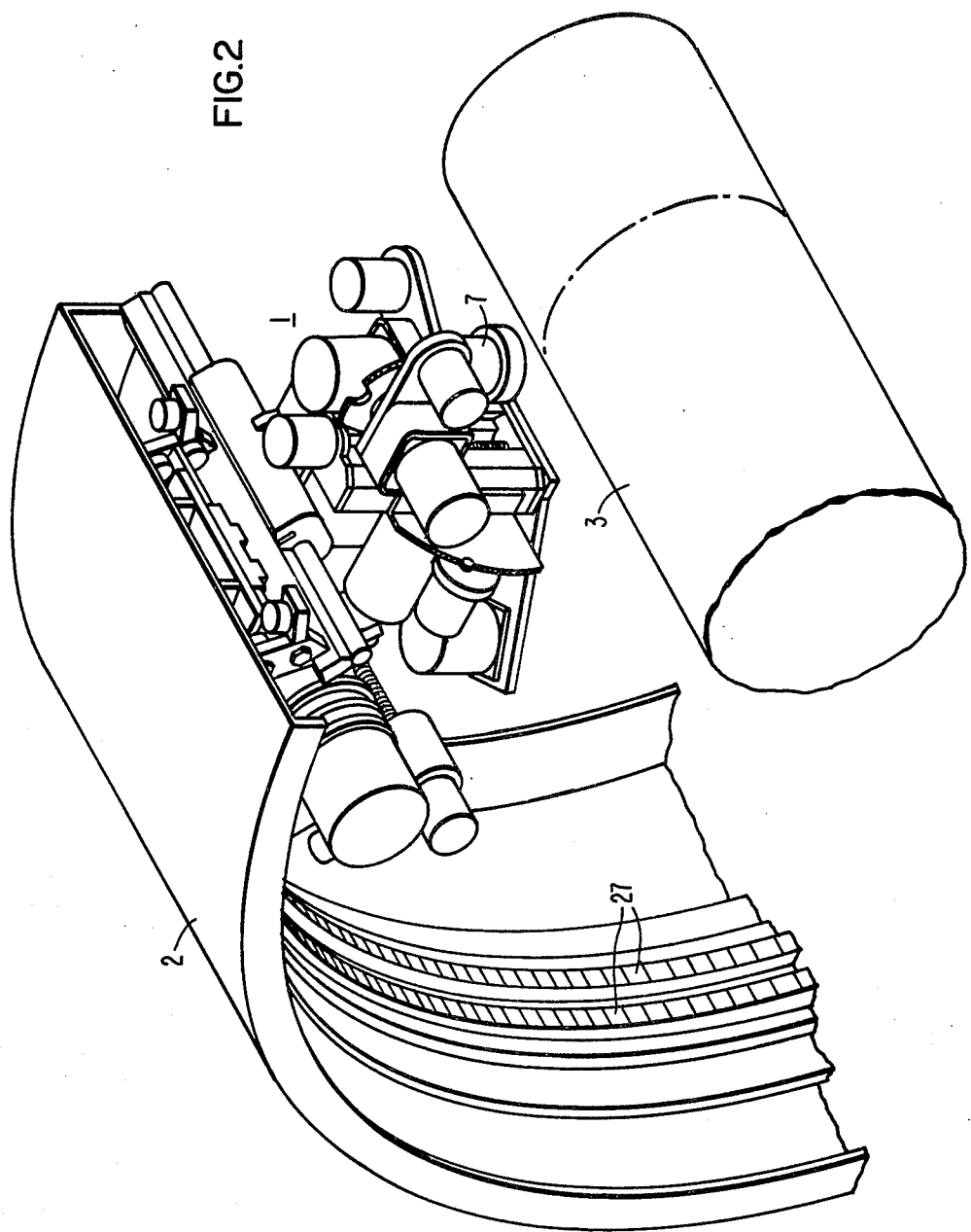
FIG. 2 is a perspective drawing of the scanner track assembly and scanner truck.
Figure 3:
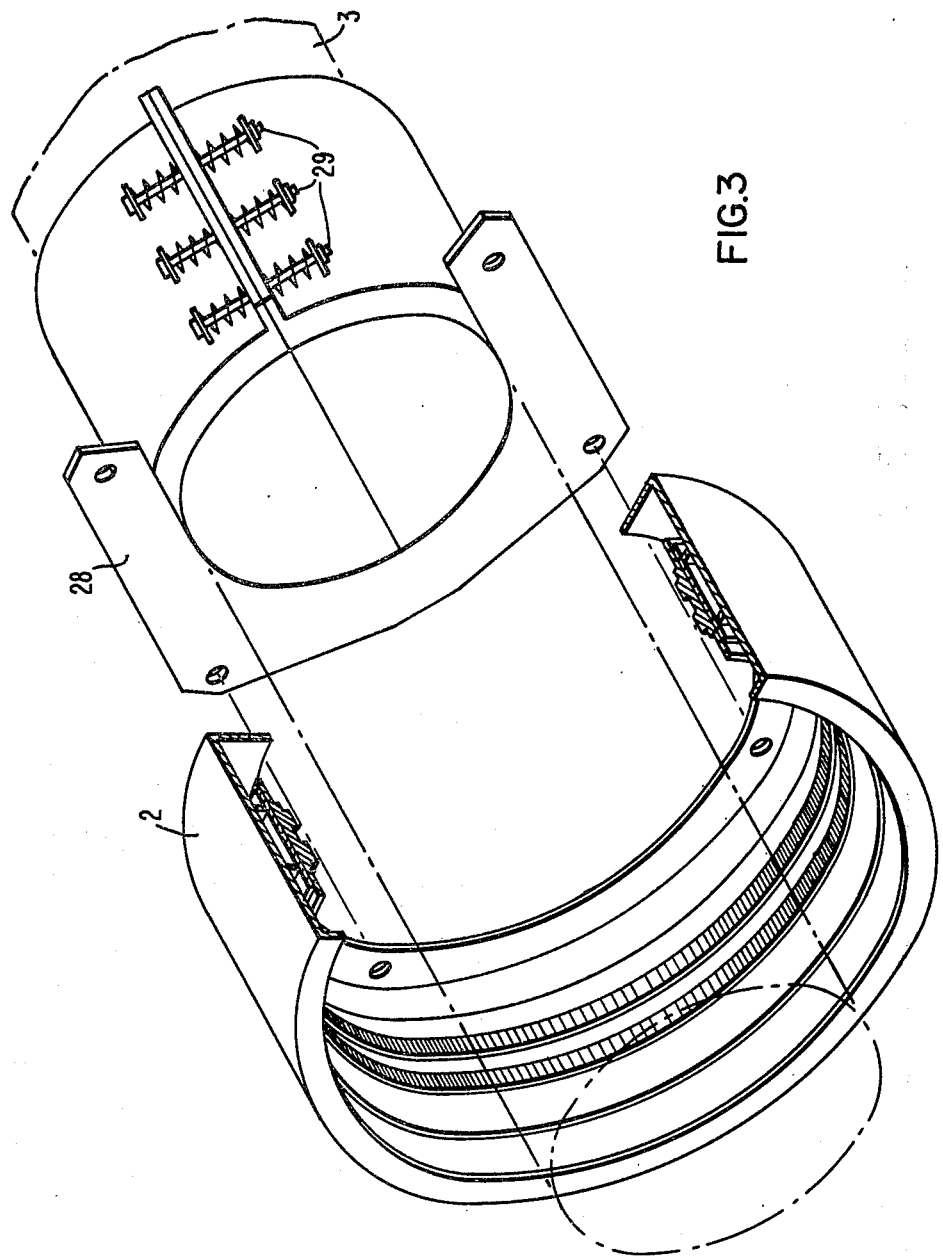
FIG. 3 is a perspective drawing of the scanner track assembly with support details.

FIG. 2 is a section of track 2 showing track internal gears 27 used by scanning truck 1 to move circumferentially around pipe 3. FIG. 3 shows details of the method by which track 2 is rigidly supported by and attached to pipe 3. Track 2 is bolted to a track support 28 which is held to pipe 3 by spring-loaded bolts 29.

Figure 4:
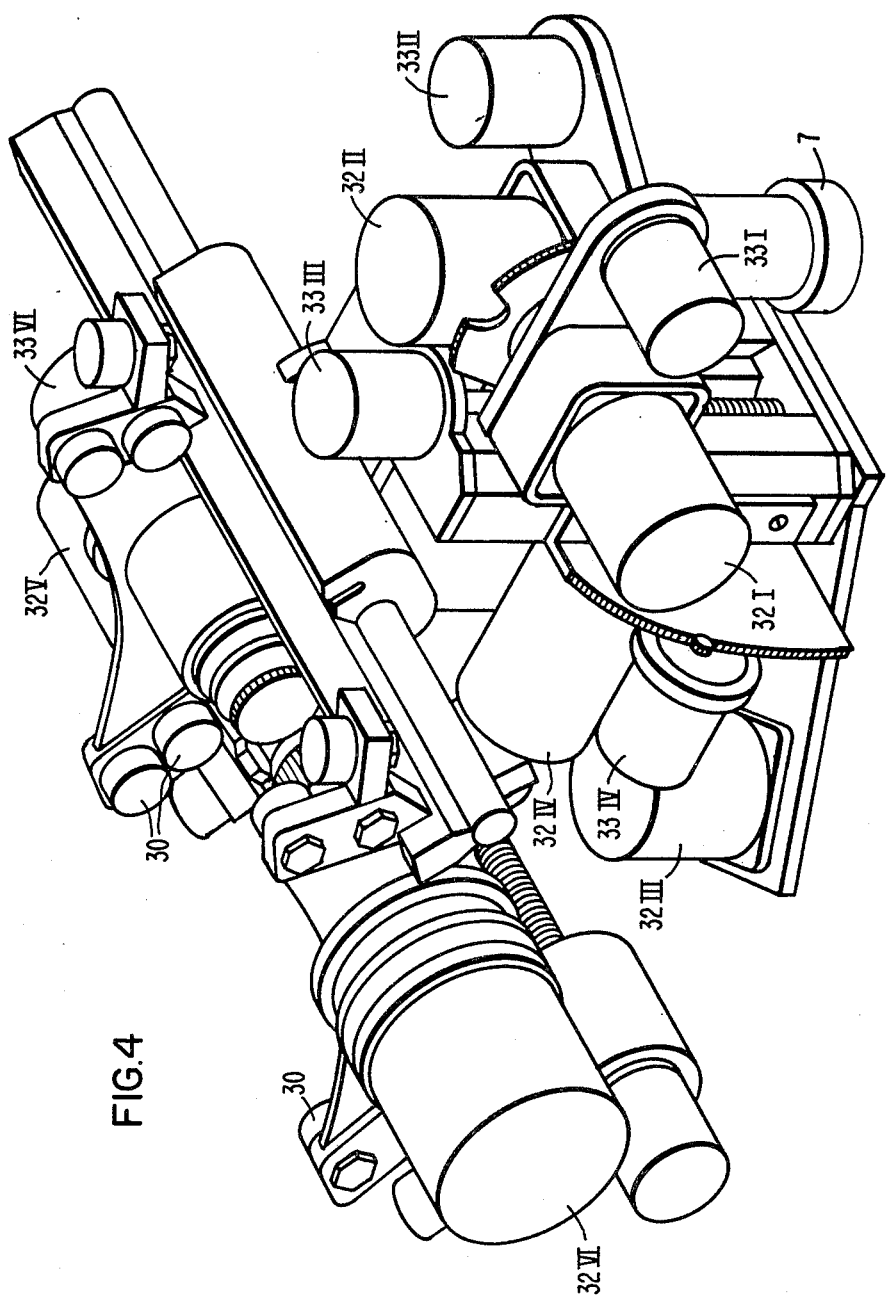
FIG. 4 is a drawing of the scanner truck.
Figure 5:
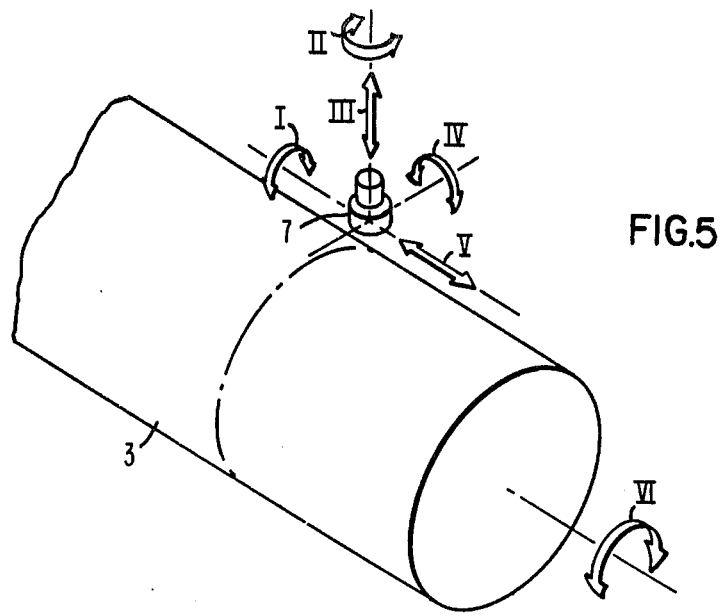
FIG. 5 is a schematic showing axis of motion of the scanner truck.

FIG. 4 is view of scanning truck 1. This scanning truck 1 is a frame having six degrees of freedom of motion which enables the computer control system to move scanner head 7 to any desired position over the pipe 3 and to tilt scanner head 7 at an angle to the pipe 3 surface. FIG. 4 shows cam rollers 30 which bear on a surface of track 2 and support scanning truck 1. Truck 1 has six groups each comprising a drive motor and a position encoder, associated with each of six degrees of freedom of scanning head 7. In FIG. 5, each of these six degrees of freedom, each being an axis or direction of motion of scanning head 7, are illustrated and labeled with a Roman numeral. In FIG. 4 and in FIGS. 6 to 11, the position encoders and drive motors associated with a particular direction or axis of motion is appropriately labeled with a Roman numeral from FIG. 5.

In FIGS. 4 and 6 to 11, all drive motors are labeled 32 and all position encoders are labeled 33.

Table 1 lists the range of travel for each of the six axis or directions of motion in FIG. 5 which is considered sufficient for the needs of this specific scanner geometry as applied to a 16" diameter pipe specimen.

TABLE 1

| Axis or Direction of Motion | Range |
|---|---|
| I circular plane rotation | ±5° |
| II radial axis rotation | ±40° |
| III radial travel | 2" (50.8 mm) |
| IV axial plane rotation | ±30° |
| V axial | 8" (203.2 mm) or ±4" (±101.6 mm) from weld |
| VI circumferential travel | 360° |

Figure 6:
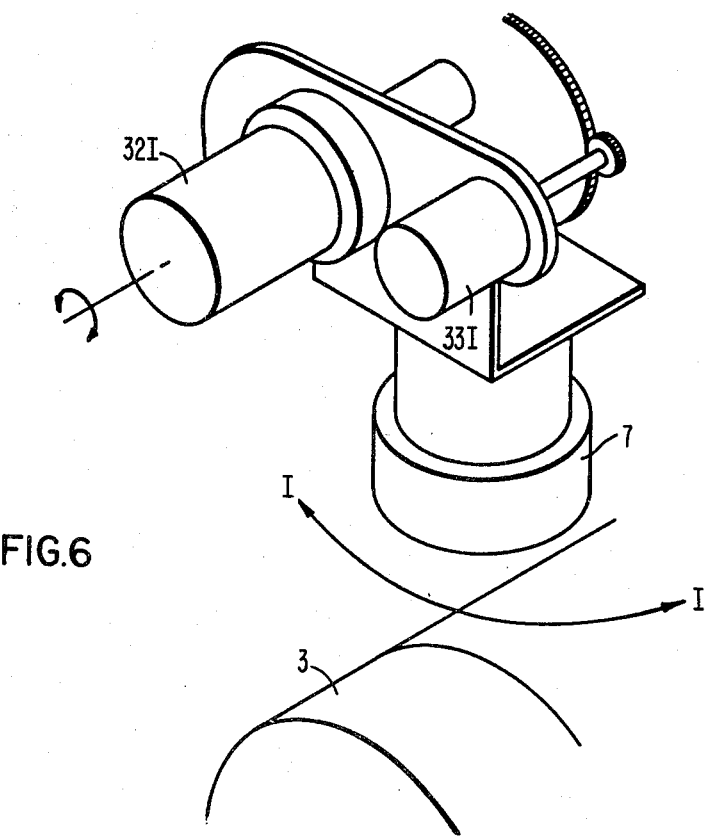
FIGS. 6 through 11 are drawings of components of the scanner truck; each of these drawings relates to a specific axis of motion as indicated in FIG. 5.

FIG. 6 is a schematic of components of scanning truck 1 which are used to achieve the circular plane rotation of scanning head 7, such motion identified as I in FIGS. 5 and 6.

Figure 7:
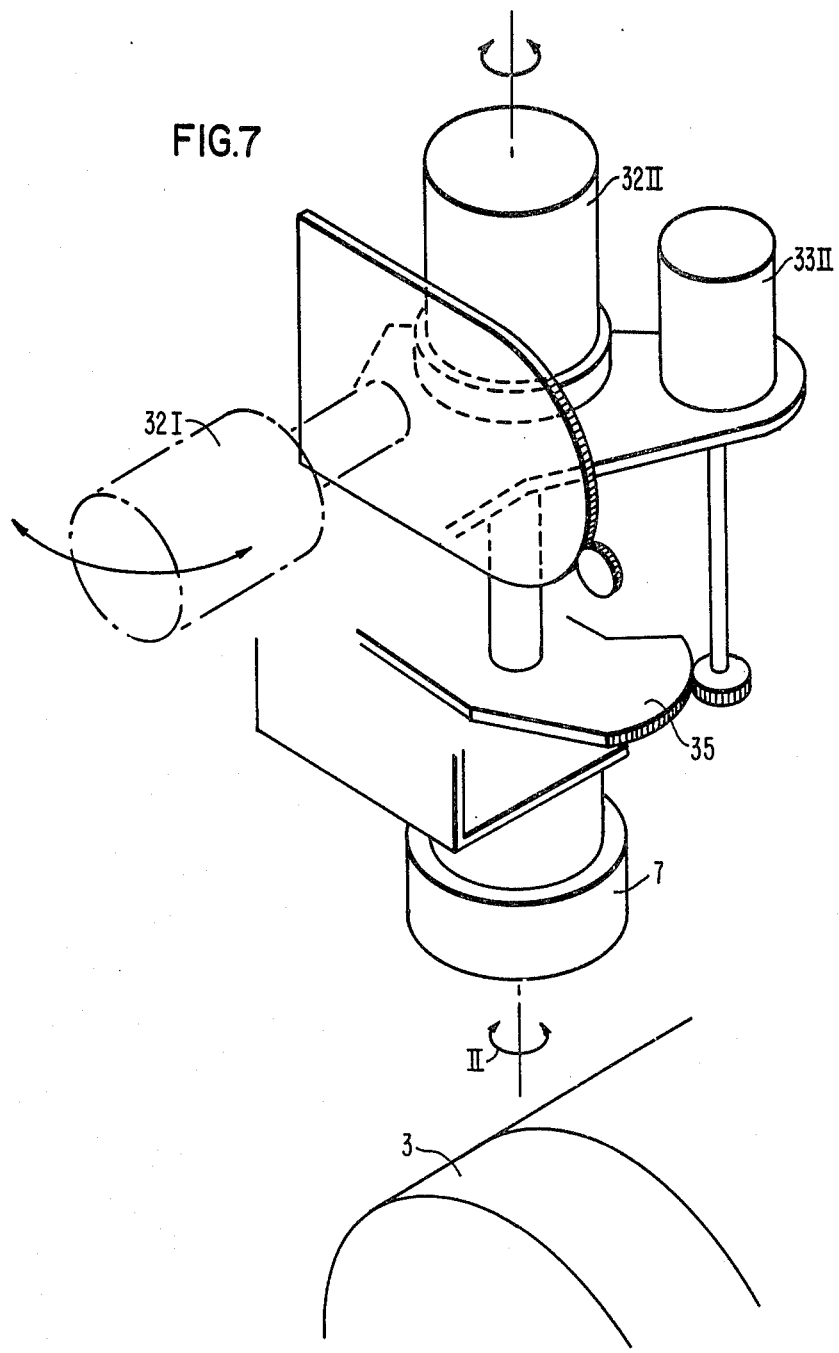

FIG. 7 is a schematic of components of scanning truck 1 which are used to achieve radial plane rotation of scanning head 7, such motion identified as II in FIGS. 5 and 7.

Figure 8:
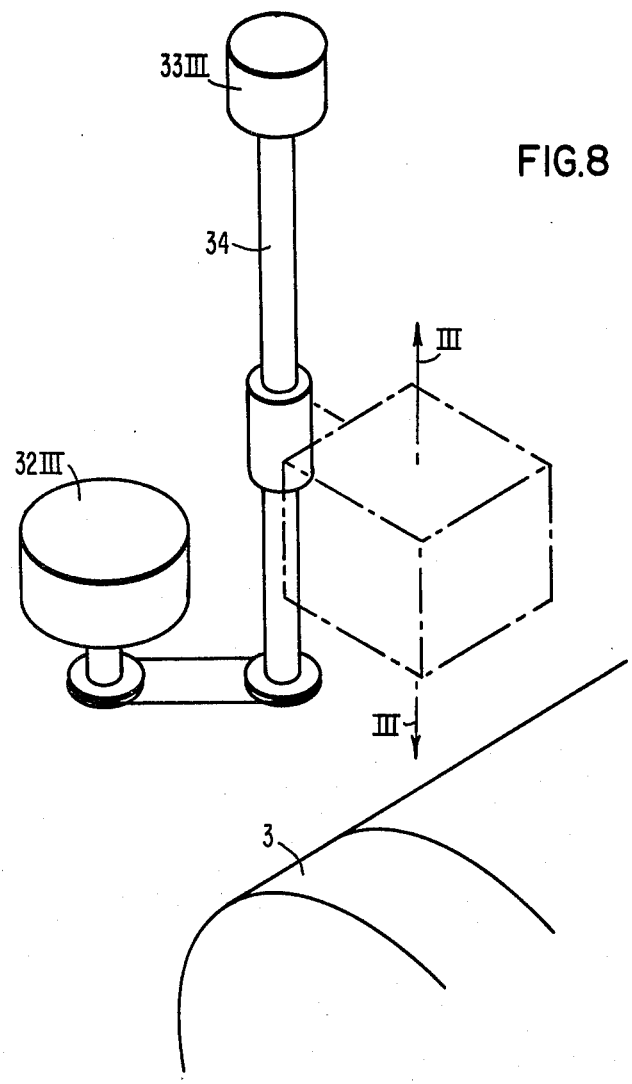

FIG. 8 is a schematic of components of scanning truck 1 which are used to achieve radial travel (parallel to the pipe radius) of scanning head 7, such motion identified as III in FIGS. 5 and 8. It is to be noted that lead screw 34 in FIG. 8 operates via a chain or belt drive from the drive motor (a stepping motor of 200 steps/revolution) to move scanning head 7 and also components associated with motions I and II.

Figure 9:
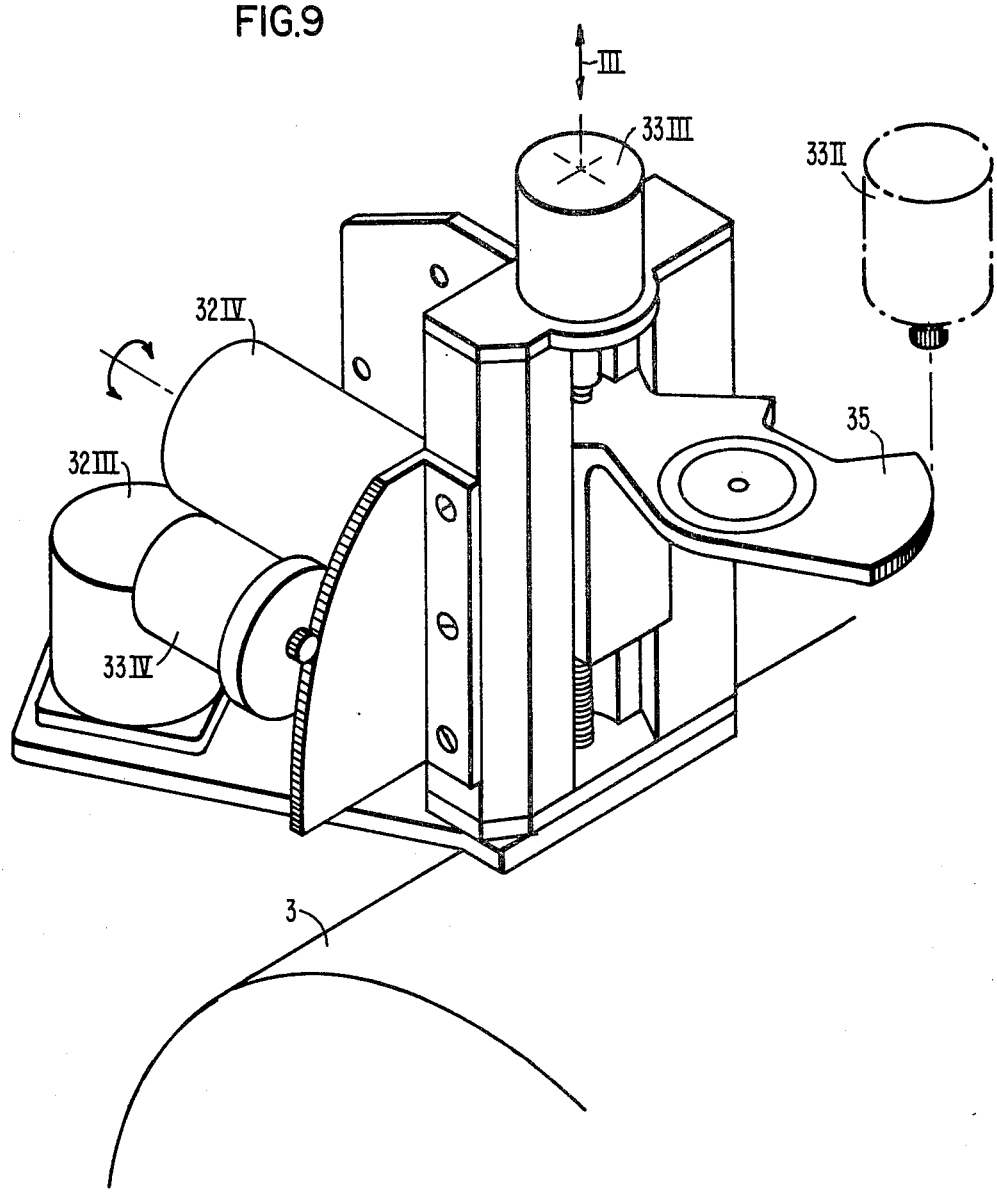

FIG. 9 is a schematic of components of scanning truck 1 which are used to achieve axial plane rotation of scanning head 7, such motion identified as IV in FIGS. 5 and 9. FIG. 9 also shows encoder feedback gear 35 which is associated with motion II.

Figure 10:
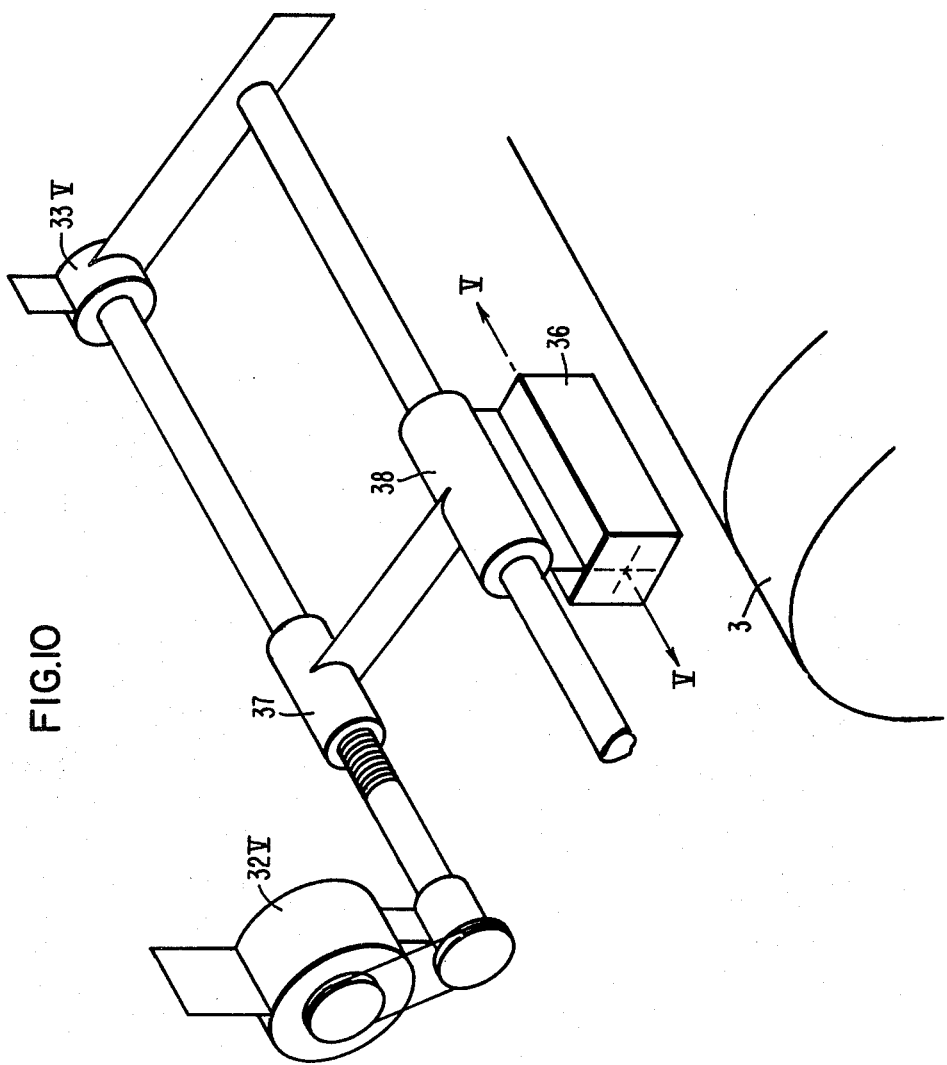

FIG. 10 is a schematic of components of scanning truck 1 which are used to achieve axial travel of scanning head 7 along pipe 3 length, such motion identified as V in FIGS. 5 and 10. Drive motor 32 is a stepping motor which drives a ball nut 37, thereby moving a frame 36 attached to a ball bushing 38. Frame 36 bears the entirety of the components of scanner truck 1 associated with notions I to IV.

Figure 11:
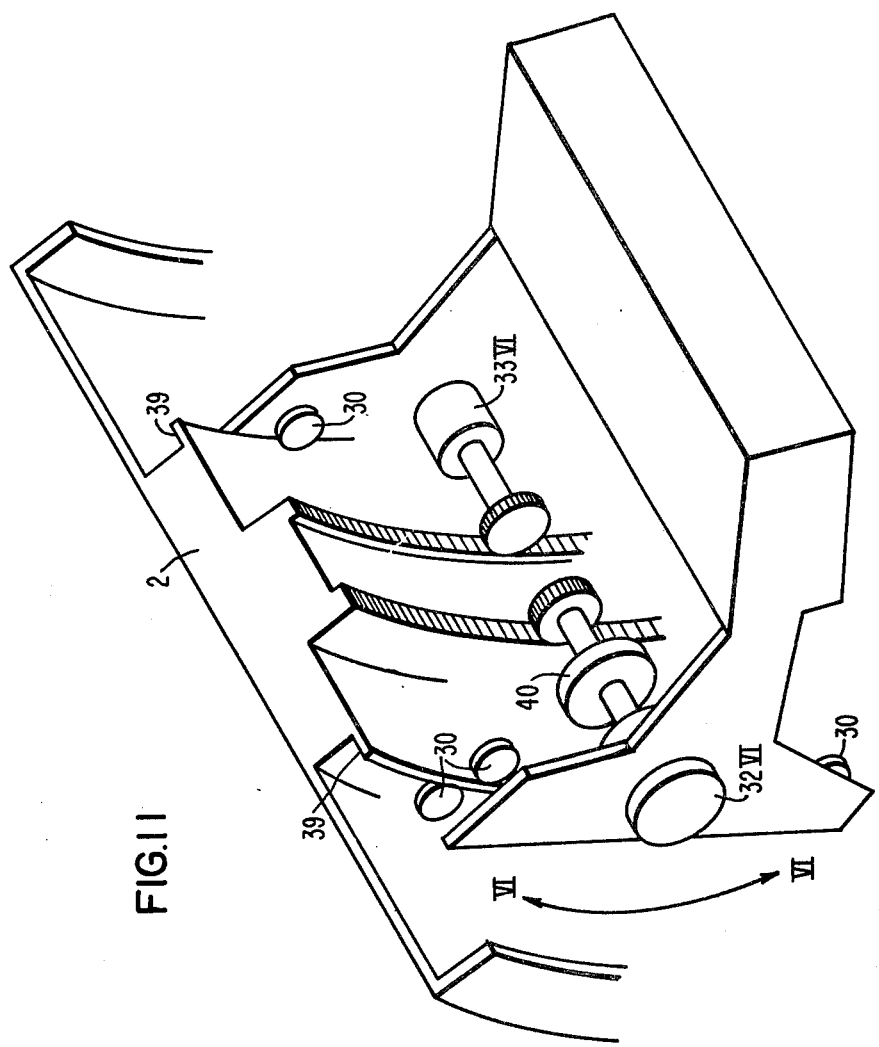

FIG. 11 is a schematic of components of scanning truck 1 which are used to achieve circumferential travel of scanning truck 1 around track 2, such motion identified as VI in FIGS. 5 and 11. Cam rollers 30 roll on track lip 39, supporting truck 1. The motion is impelled by stepping motor 32 via positive gear action and a speed reducer 40.

A study of FIGS. 6 through 11, or reference to FIG. 5, shows that scanning head 7 may be tilted at an angle to the pipe surface, moved to a desired standoff distance above the surface, and moved axially and circumferentially along pipe 3. The computer control system, by appropriate instructions to the driving motors and with feedback from the position encoders, can achieve a complete inspection sweep of a portion of the pipe surface, easily encompassing a weld and nearby material. Six degrees of motion freedom are necessary to achieve any arbitrary transducer orientation; in practice, fewer than 6 degrees of freedom may be adequate.

Figure 12:
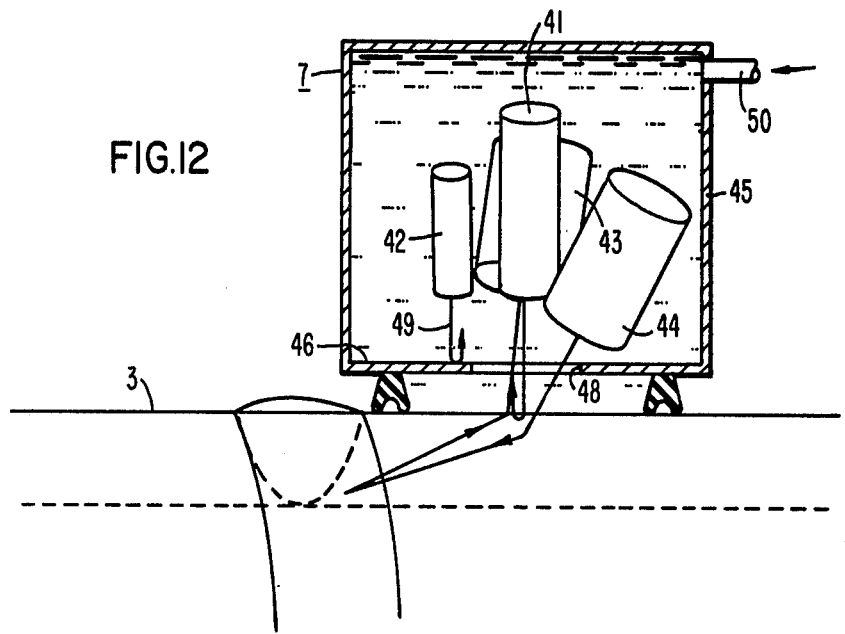
FIG. 12 is a schematic of the three element scanner head.

Refer to FIG. 12. Scanning head 7 can be seen to contain four elements: a profiling transducer 41, a velocity sensing transducer 42, and specimen inspection transducers; a pitch-catch pair 43 and 44. Outer case 45 of scanning head 7 has a opening 48 which is disposed to allow unhindered passage of ultrasonic waves from transducers 41, 43 and 44, but not transducer 42. The ultrasonic wave from this velocity sensing TR transducer 42 reflects off reflector surface 46, as shown by sound path arrow 49 in FIG. 12, and returns to TR transducer 42. This sound wave, having twice traversed a known distance through couplant, can be used to determine the acoustical velocity in the couplant using the time-of-flight of the signal. This acoustical velocity is temperature dependent, and is determined here at a site very close to the other transducer elements thereby minimizing error when the determined velocity is applied to data from the other transducers.

Scanner head 7 has a constant supply of couplant, shown entering scanning head 7 at inlet 50. The couplant flows through scanning head 7 and exits through opening 48 to fill a volume with couplant above and in contact with the pipe surface thereby providing an acoustical path for the ultrasonic waves between the pipe 3 surface and the transducers 41, 43 and 44.

Figure 16:
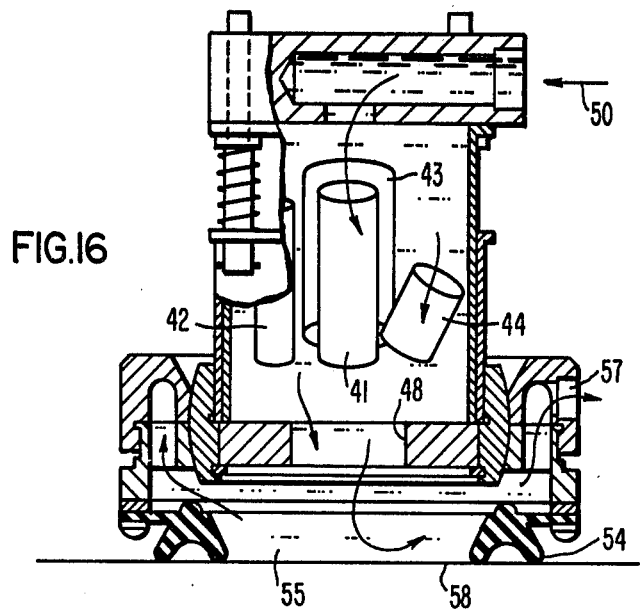
FIG. 16 is a section of the scanning head showing a bellows seal for forming a couplant volume.

FIG. 16 illustrates the containment method for the couplant volume above the specimen surface. Pressure-impelled couplant enters the scanning head at inlet 50, fills bellows volume 55, and flows out for recycle at outlet 57. Leakage past the bellows 54 and specimen surface 58 may be discarded or gathered for recycle. Bellows 54 must be sufficiently pliable to be capable of achieving reasonable seals within the expected angles of operation.

Figure 13:
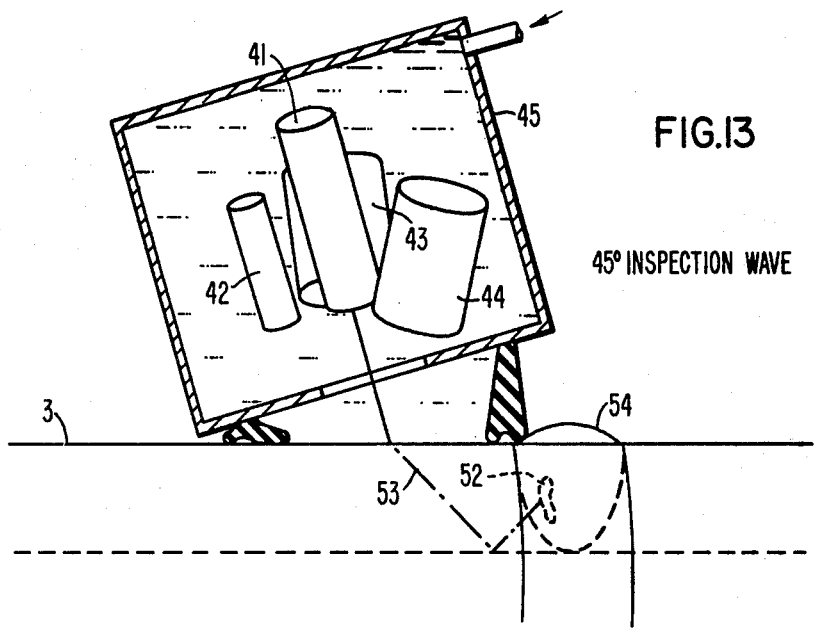
FIG. 13 is a schematic which illustrates a specimen inspection using a 45° ultrasonic wave.

It is well known in the art of ultrasonic inspection that different angles between the test signal and the specimen surface provide different defect image qualities. Various angles are therefore normally used, a 45° inspection angle being illustrated in FIG. 13. Internal void 52 reflects the wave 53 backward returning to the transducer for detection of the void 52 by detection of the echo. The application represented in this drawing is inspection of a weld 54 in the pipe 3 wall. FIG. 12 shows that inspection elements 43 and 44 have an angle of inclination with respect to each other. This is one possible pitch-catch configuration found effective for inspection of welds.

Figure 14:
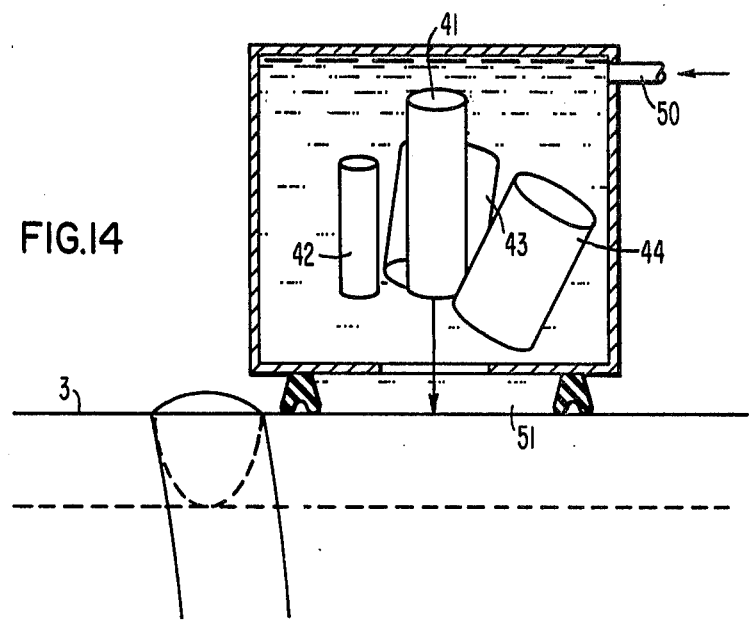
FIG. 14 is a schematic which illustrates outer surface profiling.
Figure 15:
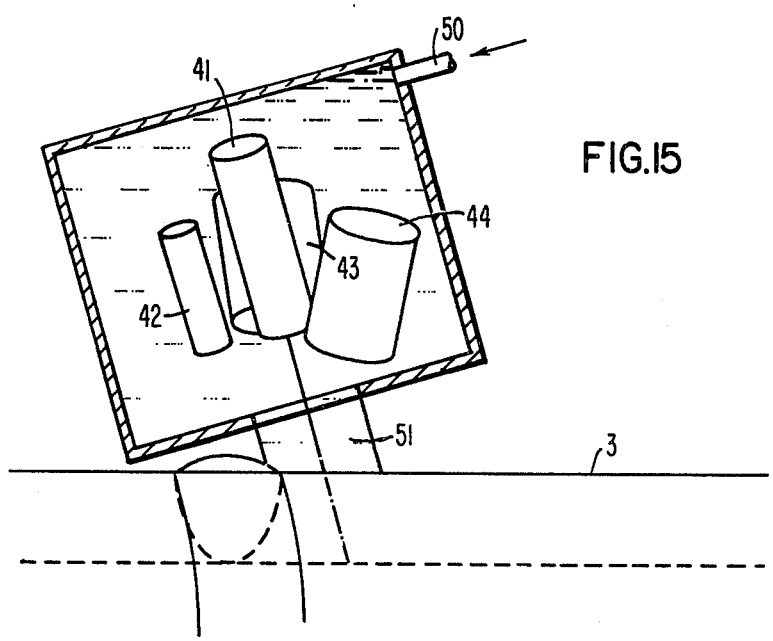
FIG. 15 is a schematic which illustrates inner surface profiling.

Refer to FIGS. 14 and 15. These drawings show use of the system to respectively accomplish outer and inner surface profiling.

FIG. 14 has the couplant containment arrangement described hereinabove, but FIG. 15 illustrates an alternate arrangement useful when the pipe surface geometry prevents an effective couplant seal, or surface or environmental temperatures are too high for the bellows material, or when an angle of scan is used in which the bellows does not seal. In FIG. 15, a steady stream 51 of couplant flows onto the pipe surface providing an acoustical path. The couplant flow is gathered by sumps for recycle.

The goal of providing the apparatus with automatic control with sufficient precision to allow data scans to be reliably repeated is achieved by use of a computer system. The computer receives input signals from all transducers as well as all position encoders associated with all degrees of motion freedom. In application, an initial profiling scan of the specimen surface is done, perhaps prior to operation or use. There is introduced onto a surface of the specimen a geometric pattern of marks sufficiently unique and durable as to be recognizable over specimen life. For example, three indentations forming a one inch sided equilateral triangle might be placed on the surface using a steel punch. These three points can be precisely located using the profile transducer and the points' coordinates (from the position encoders) stored by the computer. One of the three points, or a fourth point related in position to the other three (as for example, the center of the triangle) is used by the computer as a zero reference point for the definition of a computer coordinate system. As inspection and surface profiling scans are performed, either by a programmed or manually controlled sweep of scanner head 7, data from the transducers and position encoders are stored by the computer using the computer coordinate system.

In future scans, the computer can be instructed from a remote terminal to search for the reference marks which are presumed to still exist and to be immobile with respect to the specimen. Computers are well known to be capable of such pattern recognition. Upon locating the reference marks and storing their new coordinates, the old coordinates can be recalled and a coordinate transformation performed to relate the old coordinates to the new. This transformation, a routine mathematical art, can be applied to all old coordinate data such that an inspection scan identical to the initial or earlier one can be performed. The computer can automatically control a new scanning inspection over the identical route through space while storing inspection data in association with position encoder signals. Data received in the new scan can be compared with the data obtained previously to calculate defect propagation since the scan patterns are duplicates. Alternatively, a scan of any route can be done with data stored as received and comparison calculations nevertheless performed with appropriately paired data sets.

All transducer signals are initially echo or primary signal times-of-flight. The surface profile and inspection data are meaningful as position data for the point of reflection. The conversion of times-of-flight to geometrical position data is done by mulipliction of appropriate time intervals by the acoustical velocity as continuously monitored. The resulting position data can be stored directly or transformed to the computer reference system as desired.

The acoustical velocity is also monitored during inspection after position data are obtained. The acoustical velocity is used to continuously adjust transducer position and timing information to compensate for changes in sound refraction angle and travel time occasioned by such acoustical velocity change.

From the above, it is seen that inspecton repeatability and defect propagation calculations are possible due to storage of inspection data in conjunction with encoder position signals calibrated by deliberately added reference marks. As a further refinement, the computer coordinate system may be based on naturally occurring surface features recognizable by ultrasonic profiling equipment.

The computer control program for the scanning apparatus may have axial pipe profiling, circumferential pipe profiling, and specimen inspection phases. Axial pipe profiling may be used to determine the center of the weld, determine the angle between the longitudinal axis of the pipe and the axial drive (motion V in FIG. 5) if any, map the radial shrinkage of the pipe adjacent to the weld, map actual pipe wall thicknesses, and determine the physical edge of the weld bead. Circumferential surface profiling is used to determine the actual circular contour of the pipe relative to scanner truck 1 to determine correction factors for later control of scanning head 7 standoff distance, and to map physical details of the weld bead edge for possible realignment of present and future data scans.

Data from surface profiling can be used to control alignment of scanning head 7 such that a specific angle of wave impingement is constant throughout the scan even though the surface contour changes.

The computer control program may be so written as to allow the operator of the system to initiate a scan by specification of a particular reflection angle, offset distance along the pipe axis from the weld edge, and scanning head 7 standoff distance. The computer will then automatically accomplish a complete circumferential scan, holding the above parameters constant using previously generated profile data and real time corrections to compensate for acoustical velocity changes.

DESCRIPTION OF A SECOND EMBODIMENT

Figure 17:
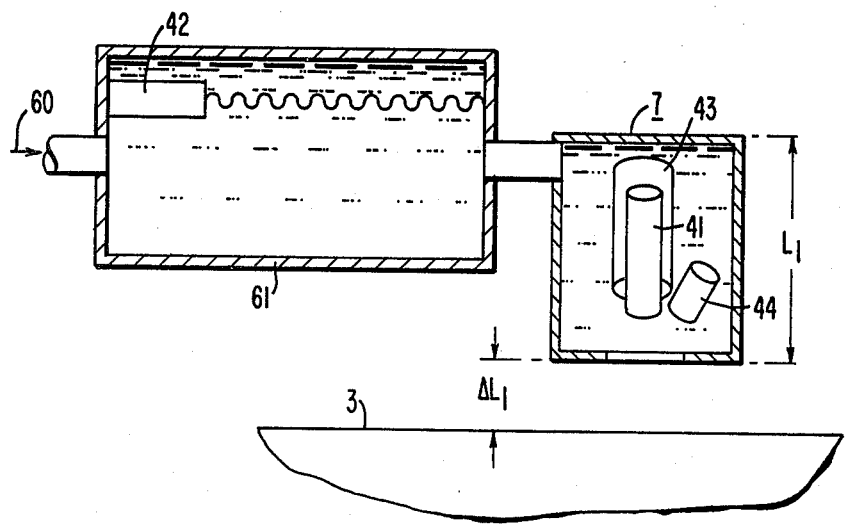
FIG. 17 is a schematic which illustrates an alternate velocity sensing transducer placement.

A second embodiment has been developed in response to a problem occasionally encountered: the installed specimen is located in a cramped location such that very little room for the scanning mechanism is available. It is desired to minimize the size of scanning head 7. This has been achieved by a modification to the first embodiment in which velocity transducer 42 is not located in scanning head 7 but is rather mounted elsewhere on scanning truck 1 in close proximity to scanning head 7. FIG. 17 is a schematic of the modification. In FIG. 17, a couplant stream 60 enters a casing 61 which houses velocity transducer 42. The velocity transducer 42 monitors the acoustical velocity within casing 61 which velocity is considered to be either identical to or of constant offset from the acoustical velocity in the vicinity of the other transducers in scanning head 7.

The size of scanning head 7 can now be smaller since scanning head 7 does not include the acoustical velocity transducer.

In practice, the difference between the acoustical velocity in casing 61 and in scanning head 7 can be determined prior to a scan and appropriate calibration factors calculated. Calibration factors so determined may be frequently checked during a scan by intermittent use of the profiling transducer or inspection transducers as a velocity transducer sensitive to the change in time-of-arrival of a signal over a small increment in stand-off distance ($\Delta L_1$). This calculation is of less accuracy than the measurement of acoustical velocities over greater distances and introduces small errors which must be accepted as a necessary penalty paid if spacial limitations are to be met.

Naturally, many variations of the scanning procedure can be used if the main computer program is so written. Preparation of appropriate computer control software programs to accomplish complete control of the system and proper storage and processing of the data is considered to be outside the present invention and within the capability of a reasonably skilled computer programmer. Albeit non-essential data, a complete listing of a computer program developed for use in a test model is included herein as Appendix A.

Operability of the ultrasonic inspection apparatus has been verified by construction of a working model and functional testing with 400° F. sodium filled piping with notch defects and deliberately added surface reference marks as well as natural weld features.

While the apparatus has been described as a weld inspection device, the novel features are obviously applicable to devices which perform tasks other than repeatedably, automatically locating defects in metal. For example, the inspection transducer in the scanning head could be replaced with a mechanical device intended to perform a special function such as a welding torch or screwdriver. Therefore, in the following claims, the word "inspection" is defined to encompass any task or act performed by the apparatus upon the specimen, the apparatus being characterized as an advanced deployment apparatus, such term "inspection" specifically including an ultrasonic search for defects.

The above specification and drawings are susceptible to various modifications without deviation from the true spirit and scope of the invention. For example, ultrasonic transducers of types other than piezoelectric crystals can be substituted. Therefore, this disclosure should be interpreted as illustrative rather than limiting.

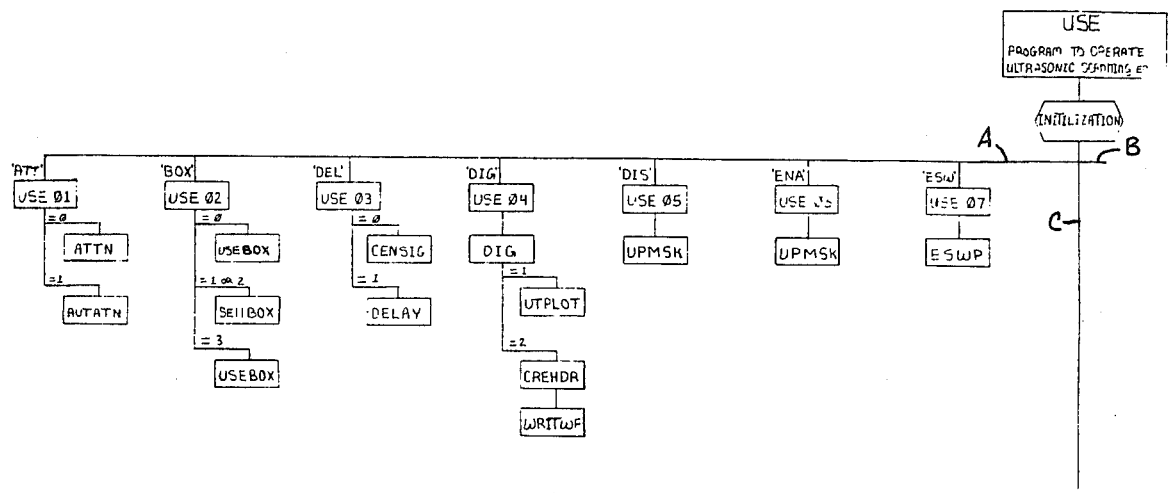

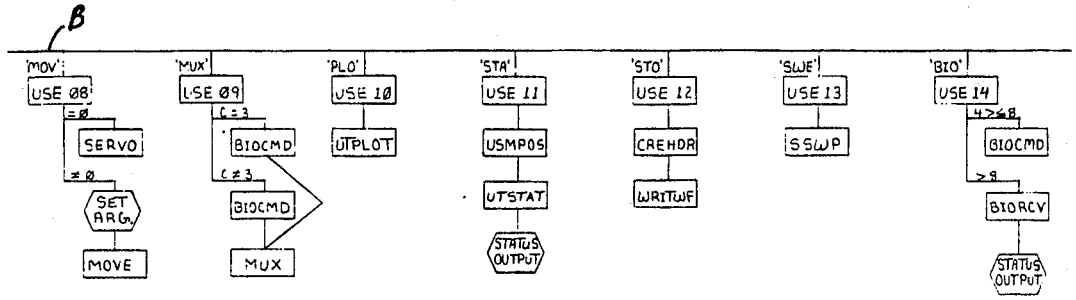
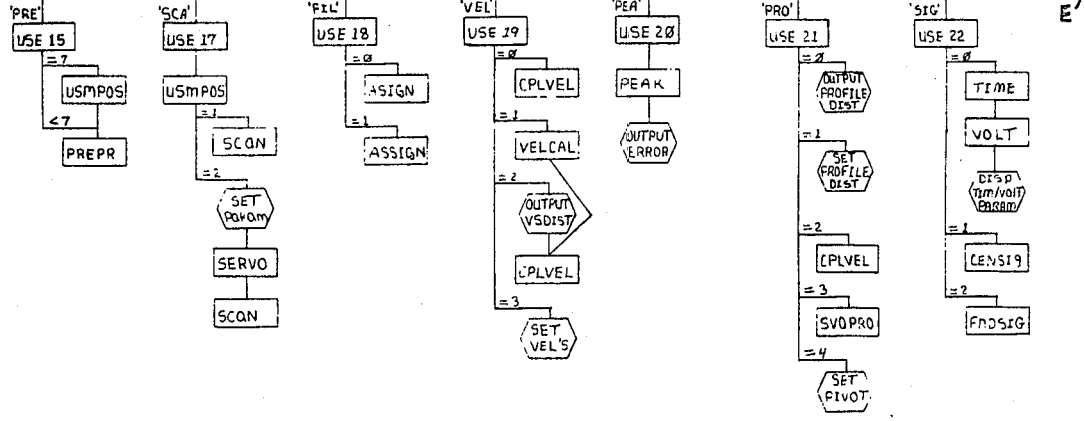
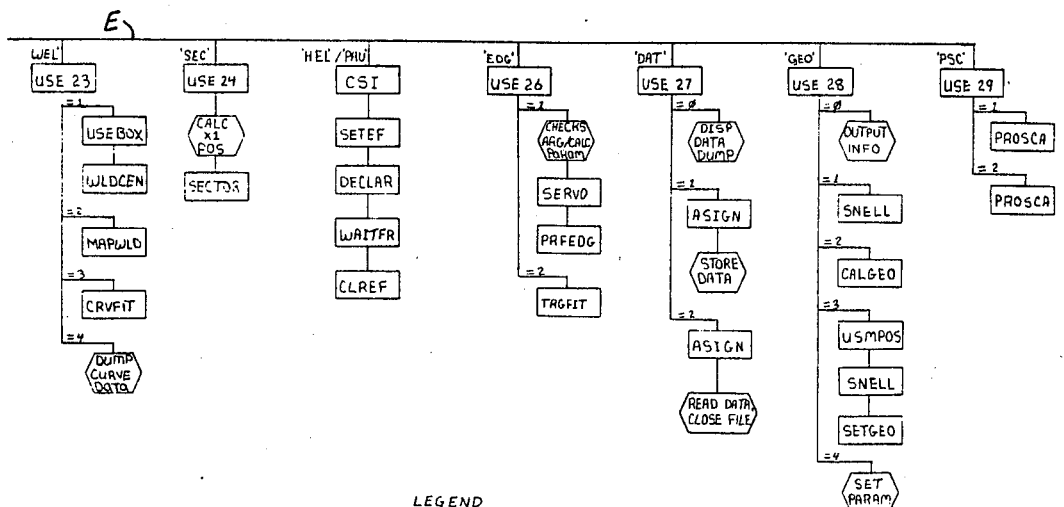
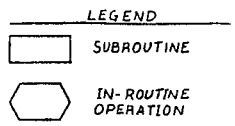
USE PROGRAM
HIERARCY
FLOW CHART
2/3/81

AMP.FTN; 1                    SPOOL DATE: 09-FEB-81

```
C*** SUBROUTINE AMP.FTN
C*** J. E. HORN ***
C*** 5/22/80 ***
C*** SUBROUTINE TO GET AMPLITUDE OF MINUS PEAK IN VOLTS ***
      SUBROUTINE AMP(V)
      COMMON /UT/ U(5)
C*** GET VOLTAGE AS FRACTION OF FULL SCALE ***
      CALL VOLT(VP,VM)
C*** SCALE USING VOLTAGE SCALE AND ATTENUATION ***
      V=-VM*U(4)*EXP(U(2)/8.685889638)
      RETURN
      END
```

ANSWR.FTN; 4                  SPOOL DATE: 09-FEB-81

```
C*** SUBROUTINE ANSWR.FTN ***
C*** J. E. HORN ***
C*** 1/8/80 ***
C*** SUBROUTINE TO ACCEPT YES OR NO ANSWERS ***
C*** IANS=1 IF YES; 0 IF NO ***
      SUBROUTINE ANSWR(IANS)
C*** PRINT PROMPT ***
100   WRITE(5,1)
1     FORMAT (1H+,$,'(Y OR N): ')
      READ(5,2,END=1000)IANS
2     FORMAT(A1)
C*** CHECK IF ANSWER VALID (Y OR N) ***
      IF(IANS.NE.'Y') GO TO 200
C*** ANSWER IS YES; SET IANS TO 1 ***
      IANS=1
      RETURN
200   IF(IANS.NE.'N') GO TO 300
C*** ANSWER IS NO; SET IANS TO 0 ***
      IANS=0
      RETURN
C*** ILLEGAL ANSWER - WRITE TO PREVENT OVERWRITE ***
300   WRITE(5,3)
3     FORMAT(1X)
      GO TO 100
1000  CALL EXIT
      END
```

ASIGN.FTN;14                    SPOOL DATE: 09-FEB-81

```
C*** SUBROUTINE ASIGN.FTN ***
C*** J. S. EMMONS ***
C*** 1/19/78 ***
C*** SUBROUTINE TO MAKE DEVICE ASSIGNMENTS ***
         SUBROUTINE ASIGN(ID)
         LOGICAL*1 NA,ISP
         COMMON /FNAME/ NC,NA(32)
         ISP="40
50       WRITE(5,1)
1        FORMAT('$ENTER FILENAME: ')
         READ(5,2,END=1000) NA
2        FORMAT(32A1)
         WRITE(5,3) NA
3        FORMAT(' FILENAME: ',32A1,/,
        .'$IS IT CORRECT? ')
         CALL ANSWR(IANS)
         IF(IANS.EQ.0) GO TO 50
         DO 100 I=1,32
            NC=33-I
            IF(NA(NC).NE.ISP) GO TO 200
100         CONTINUE
200      CALL ASSIGN(ID,NA,NC)
         RETURN
1000     CALL EXIT
         END
```

ATTN.FTN;4                      SPOOL DATE: 09-FEB-81

```
C*** SUBROUTINE ATTN.FTN ***
C*** J. E. HORN ***
C*** 11/6/79 ***
C*** SUBROUTINE TO SELECT UT ATTENUATION ***
         SUBROUTINE ATTN(A)
         COMMON /ARG/ NCMD(10),XARG(50)
C*** SEND COMMAND TO SET ATTENUATION ***
         NCMD(1)=3
         XARG(1)=A
         CALL SNDCMD(1,2,IERR)
C*** UPDATE COMMON ***
         CALL UTSTAT
         RETURN
         END
```

AUTATN.FTN;5                         SPOOL DATE: 09-FEB-81

```
C*** SUBROUTINE AUTATN.FTN ***
C*** J. E. HORN ***
C*** 3/29/80 ***
C*** SUBROUTINE TO AUTOMATICALLY ADJUST ATTENUATION SO THAT
C*** BIOMATION IS 84-96 PERCENT OF FULL SCALE ***
        SUBROUTINE AUTATN
        DIMENSION V(2)
        COMMON /UT/ U(5)
        COMMON /MASK/ MSKUSM(6),MSKUT(3),MSKTRM
        DATA VDES /0.9/
C*** SEE IF ATTENUATION MASKED ***
        IF(MSKUT(2).EQ.0) RETURN
        CALL UTSTAT
C*** READ BIOMATION VOLTAGE ***
100     CALL BIORCV(1,V)
        PV=AMAX1(V(1),-V(2))
        IF(PV.GE.0.84.AND.PV.LE.0.96) RETURN
C*** SET IF AT ATTENUATION LIMITS ***
        IF(U(2).EQ.0.0.AND.PV.LT.0.84) RETURN
        IF(U(2).GE.79.0.AND.PV.GT.0.96) RETURN
C*** CALCULATE ATTENUATION CHANGE ***
        DELATN=20.0*ALOG10(PV/VDES)
        IF(DELATN.LT.1.0.AND.DELATN.GT.0.0) DELATN=1.0
        IF(DELATN.GT.-1.0.AND.DELATN.LT.0.0) DELATN=-1.0
        ATN=U(2)+DELATN
        CALL ATTN(ATN)
        GO TO 100
        END
```

BADD.FTN;1                           SPOOL DATE: 09-FEB-81

```
C*** SUBROUTINE BADD.FTN ***
C*** J. S. EMMONS ***
C*** 2/5/78 ***
C*** REV #1 11/9/78 - CHANGED DELAYS ***
C*** REV #2 6/4/79 - REMOVED DELAYS FOR 11/10 UT ***
C*** SUBROUTINE TO SET DR11C ADDRESS ***
        SUBROUTINE BADD(I)
        CALL IPOKE("167770,1)
        CALL IPOKE("167772,I)
        CALL IPOKE("167770,0)
        RETURN
        END
```

BIN.FTN;1                            SPOOL DATE: 09-FEB-81

```
C*** SUBROUTINE BIN.FTN ***
C*** J. S. EMMONS ***
C*** 2/5/78 ***
C*** REV #1 11/9/78 - REMOVED DELAYS ***
C*** SUBROUTINE TO INPUT FROM DR11C ***
        SUBROUTINE BIN(I)
        I=IPEEK("167774)
        RETURN
        END
```

BIOCMD.FTN;1                SPOOL DATE: 09-FEB-81

```
C*** SUBROUTINE BIOCMD.FTN ***
C*** J.E. HORN ***
C*** 3/6/80 ***
C*** SUBROUTINE TO SEND BIOMATION COMMANDS ***
      SUBROUTINE BIOCMD(ICMD,X)
C*** COMMANDS ***
C*** #1 - SET VOLTAGE SCALE ***
C*** #2 - SET TIME SCALE ***
C*** #3 - SET TRIGGER ***
C*** #4 - SET WINDOW ***
C*** #5 - LOCK PANEL ***
C*** #6 - UNLOCK PANEL ***
C*** #7 - DISPLAY ON ***
C*** #8 - DISPLAY OFF ***
      COMMON /ARG/ NCMD(10),XARG(50)
      NCMD(1)=6
      XARG(1)=FLOAT(ICMD)
      XARG(2)=X
      CALL SNDCMD(1,2,IERR)
      RETURN
      END
```

BIORCV.FTN;1                SPOOL DATE: 09-FEB-81

```
C*** SUBROUTINE BIORCV.FTN ***
C*** J.E. HORN ***
C*** 3/6/80 ***
C*** SUBROUTINE TO RECEIVE FROM BIOMATION ***
      SUBROUTINE BIORCV (ICMD,X)
      DIMENSION X(2)
      COMMON /ARG/ NCMD(10),XARG(50)
C*** #1 - RECEIVE VOLTAGE ***
C*** #2 - RECEIVE TIME ***
C*** #3 - RECEIVE TRIGGER AND WINDOW ***
C*** SEND REQUEST TO UT SYSTEM ***
100   NCMD(1)=7
      XARG(1)=FLOAT(ICMD)
      CALL SNDCMD(1,2,IERR)
C*** WAIT FOR REPLY ***
200   CALL CMDINP (2,IFLG,IERR)
      IF(IERR.NE.0) GO TO 100
      IF(IFLG.EQ.0) GO TO 200
C*** DECODE REPLY COMMAND AND SEE IF RIGHT ONE ***
      CALL CMDDEC (2,IERR)
      IF(NCMD(1).NE.3.OR.IERR.NE.0) GO TO 100
      I=IFIX(XARG(1))
      IF(I.NE.ICMD) GO TO 100
C*** SET ARGUMENTS ***
      X(1)=XARG(2)
      X(2)=XARG(3)
      RETURN
      END
```

BOUT.FTN;1                  SPOOL DATE: 09-FEB-81

```
C*** SUBROUTINE BOUT.FTN ***
C*** J.S. EMMONS ***
C*** 2/5/78 ***
C*** REV #1 11/9/78 - CHANGED DELAYS ***
C*** SUBROUTINE TO OUTPUT TO DR11C ***
      SUBROUTINE BOUT(I)
      CALL IPOKE("167772,I)
      RETURN
      END
```

BOXSW.FTN;1                       SPOOL DATE: 09-FEB-81

```fortran
C*** SUBROUTINE BOXSW.FTN ***
C*** J. E. HORN ***
C*** 11/1/79 ***
C*** SUBROUTINE TO GET BOX SWITCH POSITIONS ***
        SUBROUTINE BOXSW (IFUN, IAX, IDIR, IBUT)
        COMMON /ARG/ NCMD(10), IARG(100)
C*** SET UP AND SEND COMMAND TO REQUEST SWITCHES ***
        NCMD(1)=5
100     CALL SNDCMD(1,1,IERR)
C*** WAIT FOR PROPER RESPONSE ***
200     CALL CMDINP(1,IFLG,IERR)
        IF(IERR.NE.0) GO TO 100
        IF(IFLG.EQ.0) GO TO 200
C*** DECODE COMMAND ***
        CALL CMDDEC(1,IERR)
        IF(NCMD(1).NE.2.OR.IERR.NE.0) GO TO 100
C*** RETURN SWITCH POSITIONS ***
        IFUN=IARG(1)
        IAX=IARG(2)
        IDIR=IARG(3)
        IBUT=IARG(4)
        RETURN
        END
```

CALGEO.FTN;22                    SPOOL DATE: 09-FEB-81

```
C*** SUBROUTINE CALGEO.FTN ***
C*** J. E. HORN ***
C*** 6/16/80 ***
C*** SUBROUTINE TO CALCULATE ULTRASONIC/MECHANISM GEOMETRY ***
      SUBROUTINE CALGEO(AINC,PL,DEDG,DCEN,IERR)
C*** AINC = INCIDENT ANGLE IN DEGREES ***
C*** PL   = COUPLANT PATH LENGTH IN INCHES ***
C*** DEDG = DISTANCE TO EDGE OF WELD IN INCHES ***
C*** DCEN = DISTANCE TO CENTER OF WELD IN INCHES ***
C*** IERR = 0 IF NO ERRORS ***
C***      = 1 IF OUT OF SECTOR ***
C***      = 2 IF X4 TOO FAR OFF ***
C***      = 4 IF X2 LIMITS EXCEEDED ***
C***      = 8 IF NO INTERSECTION WITH PARABOLA ***
C***      = 16 IF PAST PARABOLIC SADDLE POINT (IDEAL GEOMETRY USED) ***
C***      = 32 IF CAN'T CALCULATE IDEAL ***
      DIMENSION A(3),C(2),X2LIM(2),XPOS(6)
      COMMON /USM/ X(6)
      COMMON /PRFPAR/ PRDIST,DELANG,DI(2),DPIV,X3PIV
      COMMON /SECDAT/ NSIDE,X1(3),X4(3),X5(3),COEF(2,3),X2CEN(3),
     . V(3),X2END(2,3),PAR(3,3)
      COMMON /EDGFIT/ ECF(3)
      DATA SF/57.2957795/
C*** PERFORM INITIAL GEOMETRY CALCULATIONS ***
      CALL USMPOS
      XPOS(1)=X(1)
      CALL INIGEO(XPOS,C,A,X2LIM,ISIDE,IERR)
      IF(IERR.EQ.1) RETURN
C*** BEGIN CALCULATIONS ***
C*** CALCULATE CURRENT PIVOT DISTANCE AND PIVOT DISTANCE AT PROFILE ***
      PCUR=DPIV-(X(3)-X3PIV)
      PPR=DPIV-(XPOS(3)-X3PIV)
C*** CALCULATE TRANSDUCER ANGLE (CHANGE SIGN) ***
      TANG=-(X(5)-XPOS(5))
C*** CALCULATE X2 AND D AT BEAM INTERSECTION POINT ***
      X2BI=X(2)+(PCUR+DI(1))*SIN(TANG/SF)
      DBI=(DI(1)+PCUR)*COS(TANG/SF)-PPR
C*** CALCUATE ANGLE OF INSPECTION ELEMENTS ***
      IDIR=ISIDE*2-3
      AINSP=TANG+IDIR*DELANG
C*** CALCULATE TRUE ANGLE IN X2-D PLANE ***
      T=90.0-AINSP
C*** CALCULATE INTERSECTION POINT WITH PIPE SURFACE ***
      CALL PARINT(X2BI,DBI,T,A,X2LIM(1),X2LIM(2),X2SUR,DSUR,IERR2)
      IF(IERR2.EQ.1) IERR=IERR+4
      IF(IERR2.EQ.2) IERR=IERR+8
      IF(IERR2.EQ.2) GO TO 150
C*** CALULATE NORMAL ANGLE ***
      ANRM=ATAN(A(2)+2.0*A(3)*X2SUR)*SF
C*** SEE IF PAST PARABOLA SADDLE POINT ***
      IF(ISIDE.EQ.1.AND.ANRM.GT.0.0) GO TO 100
      IF(ISIDE.EQ 2.AND.ANRM.LT.0.0) GO TO 100
C*** ANRM O.K. - CALCULATE INCIDENT ANGLE AND PATH LENGTH ***
      AINC=ANRM+AINSP
      PL=DI(2)+(DSUR-DBI)/COS(AINSP/SF)
      GO TO 200
C*** CALCULATE IDEAL PARAMETERS ***
100   IERR=IERR+16
150   IF(AINSP.LT.90.0.AND.AINSP.GT.-90.0) GO TO 180
```

CALGEO.FTN;22                SPOOL DATE: 09-FEB-81

```
C*** CAN'T CALCULATE IDEAL PARAMETERS ***
        IERR=IERR+32
        RETURN
C*** CALCULATE INCIDENT ANGLE, PATH LENGTH, AND X2 SURFACE COORD ***
180     AINC=AINSP
        PL=DI(2)+(PRDIST-DBI)/COS(AINSP/SF)
        X2SUR=X2BI+(PL-DI(2))*SIN(AINSP/SF)
C*** CHANGE X2 SURFACE COORD TO DISTANCE FROM EDGE AND CENTER ***
200     X2E=ECF(1)+ECF(2)*COS(X(1)/SF)+ECF(3)*SIN(X(1)/SF)
        X2C=(X2CEN(1)+X2CEN(2)+X2CEN(3))/3.0
        DEDG=ABS(X2SUR-X2E)
        DCEN=ABS(X2SUR-X2C)
        RETURN
        END
```

CENSIG.FTN;7                 SPOOL DATE: 09-FEB-81

```
C*** SUBROUTINE CENSIG.FTN ***
C*** J. E. HORN ***
C*** 4/21/80 ***
C*** SUBROUTINE TO SERVO DELAY SO SIGNAL IS CENTERED ***
        SUBROUTINE CENSIG(IERR)
        COMMON /UT/ U(5)
        DATA FLOC/0.5/,FLIM/511.0/
        IERR=0
        CALL UTSTAT
C*** AUTOSCALE ***
        CALL AUTATN
C*** GET TIME ***
        CALL TIME(T)
        T=T-U(3)
        IF(T.GE.FLIM*U(5)) GO TO 1000
C*** CALCULATE DESIRED TIME ***
        DTIM=FLOC*511.0*U(5)
C*** CALCULATE DELTA TIME AND SET DELAY ***
        DT=DTIM-T
        DLY=U(3)-DT
        CALL DELAY(DLY)
C*** AUTOSCALE AGAIN ***
        CALL AUTATN
        RETURN
C*** ERROR - SIGNAL OUT OF WINDOW ***
1000    IERR=1
        RETURN
        END
```

CHKLNK.FTN;2                 SPOOL DATE: 09-FEB-81

```
C*** SUBROUTINE CHKLNK.FTN ***
C*** J. E. HORN ***
C*** 5/27/80 ***
C*** SUBROUTINE TO CHECK LINK VIA SIGNIFICANT EVENTS ***
        SUBROUTINE CHKLNK(IL,ISTAT)
        COMMON /LNKTSK/ LNKCMD,LNKARG(5),LNKFLG(2)
C*** SET UP COMMAND NUMBER AND ARGS PASSED ***
        LNKCMD=4
        LNKARG(1)=IL
C*** CALL ROUTINE TO SEND LINK COMMAND ***
        CALL SNDLNK
C*** SET UP ARGS RETURNED ***
        ISTAT=LNKARG(2)
        RETURN
        END
```

CLRSND.FTN;1                    SPOOL DATE: 09-FEB-81

```
C*** SUBROUTINE CLRSND.FOR ***
C*** J. E. HORN ***
C*** 6/8/79 ***
C*** SUBROUTINE TO CLEAR SENDER'S FIFO ***
        SUBROUTINE CLRSND(ICMP)
        IADD="070+ICMP
        CALL BADD("2000+IADD)
        CALL BOUT(0)
        RETURN
        END
```

CMDDEC.FTN;11                   SPOOL DATE: 09-FEB-81

```
C*** SUBROUTINE CMDDEC.FOR ***
C*** J. E. HORN ***
C*** 6/22/79 ***
C*** REV. #1 - 10/31/79 - 2 LINK COMMUNICATIONS ***
C*** SUBROUTINE TO DECODE NEXT COMMAND ***
        SUBROUTINE CMDDEC(IL,IERR)
        DIMENSION XARG(50)
        COMMON /RCV/ IC(2),IP(2),ICMD(128,2),MXC(2),LEN(20,2),NSIZ(2)
        COMMON /ARG/ NCMD(10),IARG(100)
        EQUIVALENCE (XARG(1),IARG(1))
        DATA ISTX/"002/,IETX/"003/,IEOT/"004/
        IERR=0
        NCMD(1)=0
C*** SEE IF EOT ***
        IF(ICMD(IP(IL),IL).NE.IEOT) GO TO 50
        IP(IL)=0
        RETURN
C*** MAKE SURE NEXT IS STX ***
50      IF(ICMD(IP(IL),IL).NE.ISTX) GO TO 300
        IP(IL)=IP(IL)+1
C*** SET COMMAND AND FILL UP ARGUMENT ARRAY ***
        NCMD(1)=ICMD(IP(IL),IL)
        IF(NCMD(1).LT.1.OR.NCMD(1).GT.MXC(IL)) GO TO 400
        IP(IL)=IP(IL)+1
        IF(LEN(NCMD(1),IL).EQ.0) GO TO 200
        DO 100 I=1,LEN(NCMD(1),IL)
           IARG(I)=ICMD(IP(IL),IL)
           IP(IL)=IP(IL)+1
100        CONTINUE
C*** MAKE SURE NEXT IS ETX ***
200     IF(ICMD(IP(IL),IL).NE.IETX) GO TO 300
        IP(IL)=IP(IL)+1
        RETURN
C*** STX/ETX ERROR
300     IERR=1
        RETURN
C*** COMMAND OUT OF RANGE ***
400     IERR=2
        RETURN
        END
```

COORD.FTN;3                    SPOOL DATE: 09-FEB-81

```
C*** SUBROUTINE COORD.FTN ***
C*** J. E. HORN ***
C*** 5/20/80 ***
C*** SUBROUTINE TO CALCULATE SCAN COORDS FROM SECTOR DATA ***
        SUBROUTINE COORD(XPOS,COEF,IERR)
        DIMENSION XPOS(6),COEF(2)
C*** XPOS = COORD ARRAY ***
C*** XPOS(1) AND XPOS(2) ARE PASSED; XPOS(3:6) ARE RETURNED ***
C*** COEF = X3 COEFFICIENT ARRAY - IT IS RETURNED ***
        COMMON /SECDAT/ ISIDE,X1(3),X4(3),X5(3),X3CF(2,3),X2CEN(3),V(3),
     .  X2EP(2,3),A(3,3)
        IERR=0
C*** SEE IF IN RANGE ***
        IF(XPOS(1).GE.X1(1).AND.XPOS(1).LE.X1(3)) GO TO 200
        IERR=1
        RETURN
C*** IN RANGE - SET X5 AND X6 ***
200     XPOS(5)=(X5(1)+X5(2)+X5(3))/3.0
        XPOS(6)=0.0
C*** SEE IF IN SECTION 1 OR 2 ***
        ISEC=1
        IF(XPOS(1).GT.X1(2)) ISEC=2
        F=(XPOS(1)-X1(ISEC))/(X1(ISEC+1)-X1(ISEC))
C*** INTERPOLATE X4 POSITION ***
        XPOS(4)=X4(ISEC)+F*(X4(ISEC+1)-X4(ISEC))
C*** INTERPOLATE X3 COEFFICIENTS ***
        DO 300 I=1,2
300        COEF(I)=X3CF(I,ISEC)+F*(X3CF(I,ISEC+1)-X3CF(I,ISEC))
        XPOS(3)=COEF(1)+COEF(2)*XPOS(2)
        RETURN
        END
```

CPLVEL.FTN;5                   SPOOL DATE: 09-FEB-81

```
C*** SUBROUTINE CPLVEL.FTN ***
C*** J. E. HORN ***
C*** 4/4/80 ***
C*** SUBROUTINE TO GET COUPLANT VELOCITY***
C*** FROM VELOCITY SENSING TRANSDUCER ***
        SUBROUTINE CPLVEL
        COMMON /UT/ U(5)
        COMMON /VELPAR/ VEL,VSDIST,SSVEL(2)
C*** REMEMBER CHANNEL AND SELECT #1 ***
        C=U(1)
        CALL MUX(1.0)
C*** ASSUME DELAY AND ATTENUATION SET PROPERLY ***
        CALL TIME (T)
C*** CALCULATE VELOCITY ***
        VEL=VSDIST*2.0/T
C*** RESTORE CHANNEL ***
        CALL MUX(C)
        RETURN
        END
```

CREHDR.FTN;5                          SPOOL DATE: 09-FEB-81

```
C*** SUBROUTINE CREHDR.FTN ***
C*** J.E. HORN **
C*** 3/6/80 ***
C*** SUBROUTINE TO CREATE WAVEFORM FROM COMMON AREAS ***
        SUBROUTINE CREHDR
        COMMON /USM/ X(6)
        COMMON /UT/ U(5)
        COMMON /WF/ IW(1024),RINDX(2)
        COMMON /HDR/ HD(128)
        COMMON /FNAME/ NC,RNAM(8)
C*** USM - HD(1-6) ***
        DO 100 I=1,6
100        HD(I)=X(I)
C*** UT - HD(11-15) **
        DO 200 I=1,5
200        HD(10+I)=U(I)
C*** INDICES - HD(21-22) ***
        HD(21)=RINDX(1)
        HD(22)=RINDX(2)
C*** HD(23)=TYPE  ***
        HD(23)=2.0
C*** HD(24)=SIZE ***
        HD(24)=1024.0
C*** FILENAME - HD (31-38)
        DO 300 I=1,8
300        HD(30+I)=RNAM(I)
        RETURN
        END
```

CRVFIT.FTN;5                    SPOOL DATE: 09-FEB-81

```fortran
C*** SUBROUTINE CRVFIT.FTN ***
C*** J. E. HORN ***
C*** 5/15/80 ***
C*** SUBROUTINE TO FIT AXIAL PROFILE DATA AND FIND SLOPE ANGLE ***
        SUBROUTINE CRVFIT(IERR)
        REAL*8 ARG1,ARG2,A(3),B(3),C(5)
        COMMON /PRFDAT/ NP,NSIDE,X2EP(2),X2(100),D(100)
        COMMON /PRFFIT/ COEF(3)
        DATA PI/3.141592654/
C*** CHECK IF ENOUGH POINTS - MUST BE AT LEAST 4 ***
        IERR=1
        IF(NP.LT.4) RETURN
        IERR=0
C*** ZERO OUT FIT ARRAYS ***
        DO 100 J=1,5
          C(J)=0.0
          IF(J.LE.3) B(J)=0.0
100     CONTINUE
C*** ACCUMULATE DATA INTO FIT ARRAYS ***
        DO 300 I=1,NP
          ARG1=1.0
          ARG2=D(I)
          DO 200 K=1,5
            C(K)=C(K)+ARG1
            ARG1=ARG1*X2(I)
            IF(K.GT.3) GO TO 200
            B(K)=B(K)+ARG2
            ARG2=ARG2*X2(I)
200       CONTINUE
300     CONTINUE
C*** PERFORM PARABOLIC FIT ***
        CALL FIT(XPK,C,B,A)
C*** CONVERT COEFFICIENTS TO SINGLE PRECISION ***
        DO 400 I=1,3
400       COEF(I)=SNGL(A(I))
        RETURN
        END
```

CSI.FTN;1                       SPOOL DATE: 09-FEB-81

```fortran
C*** SUBROUTINE CSI.FTN ***
C*** J. E. HORN ***
C*** 6/11/80 ***
C*** SUBROUTINE TO GET CSI COMMAND VIA EVENT FLAGS ***
        SUBROUTINE CSI
        COMMON /CSIEF/ NFLG(2)
C*** SET EVENT FLAG 1 AND DECLARE SIGNIFICANT EVENT ***
        CALL SETEF(NFLG(1))
        CALL DECLAR
C*** WAIT FOR FLAG 2 ***
        CALL WAITFR(NFLG(2))
C*** CLEAR FLAG 2 AND EXIT TO EXECUTE COMMAND ***
        CALL CLREF(NFLG(2))
        RETURN
        END
```

DELAY.FTN;3                         SPOOL DATE: 09-FEB-81

```
C*** SUBROUTINE DELAY.FTN ***
C*** J. E. HORN ***
C*** 11/6/79 ***
C*** SUBROUTINE TO SELECT UT DELAY ***
      SUBROUTINE DELAY(D)
      COMMON /ARG/NCMD(10),XARG(50)
C*** SEND COMMAND TO SET DELAY ***
      NCMD(1)=4
      XARG(1)=D
      CALL SNDCMD(1,2,IERR)
C*** UPDATE COMMON ***
      CALL UTSTAT
      RETURN
      END
```

ESWP.FTN;1                          SPOOL DATE: 09-FEB-81

```
C*** SUBROUTINE ESWP.FTN ***
C*** J. E. HORN ***
C*** 11/1/79 ***
C*** SUBROUTINE TO END SWEEP ***
      SUBROUTINE ESWP
      COMMON /USM/ XPOS(6),ISTAT
      COMMON /ARG/ NCMD(10),XARG(50)
C*** SET UP AND SEND COMMAND ***
      NCMD(1)=4
      CALL SNDCMD(1,1,IERR)
C*** UPDATE POSITION ***
      CALL USMPOS
      RETURN
      END
```

EXIUSE.FTN;2                        SPOOL DATE: 09-FEB-81

```
C*** SUBROUTINE EXIUSE.FTN ***
C*** J. E. HORN ***
C*** 6/12/80 ***
C*** SUBROUTINE TO EXIT USE PROGRAM ***
      SUBROUTINE EXIUSE
C*** ENABLE ALL FUNCTIONS ***
      IVAL=1
      IOPT=0
      CALL UPMSK(IVAL,IOPT)
C*** WRITE TERMINATION MESSAGE ***
      WRITE(5,1)
1     FORMAT(' *** EXITING USE PROGRAM ***')
      CALL EXIT
      END
```

FINCMD.FTN;1                    SPOOL DATE: 09-FEB-81

```
C*** SUBROUTINE FINCMD.FTN ***
C*** J. E. HORN ***
C*** 5/27/80 ***
C*** SUBROUTINE TO INDICATE COMMAND FINISHED VIA SIGNIFICANT EVENTS ***
      SUBROUTINE FINCMD
      COMMON /LNKTSK/ LNKCMD,LNKARG(5),LNKFLG(2)
C*** SET FLAG 2 AND DECLARE SIGNIFICANT EVENT ***
      CALL SETEF(LNKFLG(2))
      CALL DECLAR
      RETURN
      END
```

FIT.FTN;2                       SPOOL DATE: 09-FEB-81

```
C*** SUBROUTINE FIT.FTN ***
C*** J. E. HORN ***
C*** 4/17/80 ***
C*** SUBROUTINE TO COMPUTE PARABOLIC FIT AND FIND MAX (OR MIN) ***
      SUBROUTINE FIT(XPK,C,B,A)
      REAL*8 C(5),B(3),A(3),DET,X1,X2,X3
      DET=C(1)*C(3)*C(5)+2.0*C(2)*C(3)*C(4)-C(3)*C(3)*C(3)-
     . C(2)*C(2)*C(5)-C(1)*C(4)*C(4)
      X1=B(1)*C(3)*C(5)+B(2)*C(4)*C(3)+B(3)*C(2)*C(4)-B(3)*C(3)*C(3)-
     . B(2)*C(2)*C(5)-B(1)*C(4)*C(4)
      X2=C(1)*B(2)*C(5)+C(2)*B(3)*C(3)+C(3)*B(1)*C(4)-C(3)*B(2)*C(3)-
     . C(2)*B(1)*C(5)-C(1)*B(3)*C(4)
      X3=C(1)*C(3)*B(3)+C(2)*C(4)*B(1)+C(3)*C(2)*B(2)-C(3)*C(3)*B(1)-
     . C(2)*C(2)*B(3)-C(1)*C(4)*B(2)
      A(1)=X1/DET
      A(2)=X2/DET
      A(3)=X3/DET
      XPK=-X2/(2.0*X3)
      RETURN
      END
```

FIT3X3.FTN;2                           SPOOL DATE: 09-FEB-81

```fortran
C*** SUBROUTINE FIT3X3.FTN ***
C*** J. E. HORN ***
C*** 6/16/80 ***
C*** SUBROUTINE TO 3X3 SYSTEM OF EQUATIONS ***
      SUBROUTINE FIT3X3(A,B,C)
      REAL*8 A(3),B(3),C(3,3),D
C***
      D=     C(1,1)*(C(2,2)*C(3,3)-C(2,3)*C(3,2))
      D=D -  C(2,1)*(C(1,2)*C(3,3)-C(1,3)*C(3,2))
      D=D +  C(3,1)*(C(1,2)*C(2,3)-C(1,3)*C(2,2))
C***
      A(1)=     B(1)*(C(2,2)*C(3,3)-C(2,3)*C(3,2))
      A(1)=A(1)-B(2)*(C(1,2)*C(3,3)-C(1,3)*C(3,2))
      A(1)=A(1)+B(3)*(C(1,2)*C(2,3)-C(2,2)*C(1,3))
C***
      A(2)=    -B(1)*(C(2,1)*C(3,3)-C(2,3)*C(3,1))
      A(2)=A(2)+B(2)*(C(1,1)*C(3,3)-C(1,3)*C(3,1))
      A(2)=A(2)-B(3)*(C(1,1)*C(2,3)-C(1,3)*C(2,1))
C***
      A(3)=     B(1)*(C(2,1)*C(3,2)-C(2,2)*C(3,1))
      A(3)=A(3)-B(2)*(C(1,1)*C(3,2)-C(1,2)*C(3,1))
      A(3)=A(3)+B(3)*(C(1,1)*C(2,2)-C(1,2)*C(2,1))
C***
      DO 100 I=1,3
100     A(I)=A(I)/D
      RETURN
      END
```

FNDEDG.FTN;6                    SPOOL DATE: 09-FEB-81

```
C*** SUBROUTINE FNDEDG.FTN ***
C*** J. E. HORN ***
C*** 5/20/80 ***
C*** SUBROUTINE TO FIND EDGE OF WELD BEAD ***
C*** RETURNS X2 COORD OF WHEN VOLTAGE DROPS BELOW V2 ***
      SUBROUTINE FNDEDG(V1,V2,X2INC,X2LIM,X3CF,X2VAL,IERR)
C*** V1 = UPPER CUTOFF ***
C*** V2 = LOWER CUTOFF ***
C*** X2INC = X2 INCREMENT TOWARD WELD ***
C*** X2LIM = MAX DISTANCE X2 CAN GO ***
C*** X3CF = X3 LINEAR COEFFICIENTS ***
C*** X2VAL = X2 VALUE AT EDGE ***
C*** IERR = 0 IF O.K., NON-ZERO IF ERROR ***
      DIMENSION XX(6),X3CF(2)
      COMMON /USM/ X(6)
      IERR=0
C*** REMEMBER START POSITION ***
      CALL USMPOS
      DO 100 I=1,6
100      XX(I)=X(I)
      X2STRT=X(2)
      X2=X(2)
C*** START FIRST LOOP - GO UNTIL V ABOVE V1 ***
      I=0
      DX2=-X2INC
C*** CALCULATE COORDS ***
200   DEL=DX2*I
      XX(2)=X2+DEL
      IF(ABS(XX(2)-X2STRT).GT.X2LIM) GO TO 1000
      XX(3)=X3CF(1)+X3CF(2)*XX(2)
      CALL MOVE(XX)
C*** CHECK PANIC ***
      CALL PANIC(IPNC)
      IF(IPNC.NE.0) GO TO 1200
C*** GET AMPLITUDE AND COMPARE TO V1 ***
      CALL AMP(V)
      IF(V.GE.V1) GO TO 300
      I=I+1
      GO TO 200
C*** SWITCH DIRECTION - GO UNTIL V BELOW V2 ***
300   X2=X(2)
      I=0
      DX2=X2INC
C*** SAVE PREVIOUS VALUES ***
400   VLST=V
      XLST=X(2)
C*** CALCULATE COORDS ***
      DEL=DX2*I
      XX(2)=X2+DEL
      XX(3)=X3CF(1)+X3CF(2)*XX(2)
      IF(ABS(XX(2)-X2STRT).GT.X2LIM) GO TO 1000
      CALL MOVE(XX)
C*** CHECK PANIC ***
      CALL PANIC(IPNC)
      IF(IPNC.NE.0) GO TO 1200
C*** GET AMPLITUDE AND COMPARE TO V2 ***
      CALL AMP(V)
      IF(V.LE.V2) GO TO 500
      I=I+1
```

FNDEDG.FTN;6                    SPOOL DATE: 09-FEB-81

```
              GO TO 400
C*** CALCULATE X2VAL BY INTERPOLATION AND RETURN ***
500      F=(V2-VLST)/(V-VLST)
         X2VAL=XLST+F*(X(2)-XLST)
         RETURN
C*** ERROR CONDITIONS - MOVED TOO FAR ***
1000     IERR=1
         RETURN
1100     IERR=2
         RETURN
C*** PANIC ***
1200     IERR=3
         RETURN
         END
```

FNDSIG.FTN;7                    SPOOL DATE: 09-FEB-81

```
C*** SUBROUTINE FNDSIG.FTN ***
C*** J. E. HORN ***
C*** 4/21/80 ***
C*** SUBROUTINE TO FIND SIGNAL ***
         SUBROUTINE FNDSIG(IERR)
         DIMENSION DLY(2,3)
         COMMON /UT/ U(5)
         DATA VLIM/0.5/,DLY/20.0,80.0,15.0,70.0,10.0,100.0/
         IERR=0
         CALL UTSTAT
         IMUX=IFIX(U(1)+0.5)
C*** CALCULATE DELAY INCREMENT ***
         DEL=512.0*U(5)*0.9
         DEL=FLOAT(IFIX(DEL*10.0+0.5))/10.0
         NP=IFIX((DLY(2,IMUX)-DLY(1,IMUX))/DEL+0.5)+1
C*** TAKE OUT ALL ATTENUATION ***
         CALL ATTN(0.0)
         DO 100 I=1,NP
            D=DLY(1,IMUX)+(I-1)*DEL
            CALL DELAY(D)
C*** GET VOLTAGE ***
            CALL VOLT(VP,VM)
            V=-VM
            IF(V.GE.VLIM) GO TO 200
100      CONTINUE
C*** ERROR - NO SIGNAL FOUND ***
         IERR=1
         RETURN
C*** SIGNAL - SCALE AND ADJUST TIME ***
200      CALL CENSIG(IERR)
         CALL AUTATN
         CALL CENSIG(IERR)
         RETURN
         END
```

GETCMD.FTN;1                    SPOOL DATE: 09-FEB-81

```
C*** SUBROUTINE GETCMD.FTN ***
C*** J. E. HORN ***
C*** 5/27/80 ***
C*** SUBROUTINE TO GET COMMAND USING SIGNIFICANT EVENTS ***
        SUBROUTINE GETCMD
        COMMON /LNKTSK/ LNKCMD,LNKARG(5),LNKFLG(2)
C*** WAIT FOR EVENT FLAG 1 TO GO HIGH ***
        CALL WAITFR(LNKFLG(1))
C*** CLEAR IT ***
        CALL CLREF(LNKFLG(1))
C*** RETURN TO EXECUTE COMMAND ***
        RETURN
        END
```

INDEX.FTN;1                     SPOOL DATE: 09-FEB-81

```
C*** SUBROUTINE INDEX.FTN ***
C*** J. E. HORN ***
C*** 3/26/80 ***
C*** SUBROUTINE TO INDEX MOTOR ***
        SUBROUTINE INDEX(STP,IAX)
        DIMENSION XARG(50)
        COMMON /ARG/ NCMD(10),IARG(100)
        EQUIVALENCE (XARG(1),IARG(1))
C*** SEND INDEX COMMAND ***
        NCMD(1)=10
        XARG(1)=STP
        IARG(3)=IAX
        CALL SNDCMD(1,1,IERR)
        RETURN
        END
```

INIGED.FTN;5                    SPOOL DATE: 09-FEB-81

```
C*** SUBROUTINE INIGED.FTN ***
C*** J. E. HORN ***
C*** 6/16/80 ***
C*** SUBROUTINE TO PERFORM INITIAL GEOMETRY CALCULATION FOR CALGEO AND
C*** SETGEO ***
       SUBROUTINE INIGED(XPOS,C,A,X2LIM,ISIDE,IFLG)
C*** XPOS(1) AND XPOS(2) ARE AXIS 1 AND 2 COORDS ***
C*** IFLG = 0 IF NO ERRORS ***
C***        = 1 IF OUT OF SECTOR ***
C***        = 2 IF IN SECTOR BUT X4 TOO FAR OFF ***
       DIMENSION XPOS(6),C(2),A(3),X2LIM(2)
       COMMON /USM/ X(6)
       COMMON /SECDAT/ NSIDE,X1(3),X4(3),X5(3),COEF(2,3),X2CEN(3),V(3),
      . X2EP(2,3),PCF(3,3)
       DATA X4DEL/0.5/
       IFLG=0
       XPOS(2)=X(2)
C*** CALL COORD TO SEE IF IN SECTOR AND GET X3 COEFS, X3, X4, AND X5 ***
       CALL COORD(XPOS,C,IERR)
       IF(IERR.EQ.0) GO TO 100
C*** OUT OF SECTOR - FLAG IT AND RETURN ***
       IFLG=1
       RETURN
C*** SEE IF X4 IN RANGE ***
100    IF(ABS(XPOS(4)-X(4)).GT.X4DEL) IFLG=2
C*** INTERPOLATE PARABOLIC COEFFICIENTS AND X2 LIMITS ***
200    ISEC=1
       IF(X(1).GT.X1(2)) ISEC=2
       F=(X(1)-X1(ISEC))/(X1(ISEC+1)-X1(ISEC))
       DO 300 I=1,3
300      A(I)=PCF(I,ISEC)+F*(PCF(I,ISEC+1)-PCF(I,ISEC))
       DO 400 I=1,2
400      X2LIM(I)=X2EP(I,ISEC)+F*(X2EP(I,ISEC+1)-X2EP(I,ISEC))
C*** SET SIDE OF WELD ***
       ISIDE=NSIDE
       RETURN
       END
```

INISSG.FTN;2                    SPOOL DATE: 09-FEB-81

```
C*** SUBROUTINE INISSG.FTN ***
C*** J.E. HORN ***
C*** 3/26/80 ***
C*** SUBROUTINE  TO INITIALIZE SCAN SYNC GENERATOR ***
       SUBROUTINE INISSG(IAX)
       COMMON /ARG/ NCMD(10),IARG(100)
C*** SEND COMMAND TO INITIALIZE ***
       NCMD(1)=12
       IARG(1)=IAX
       CALL SNDCMD(1,1,IERR)
       RETURN
       END
```

```
C*** SUBROUTINE LNK01.FTN ***
C*** J.E. HORN ***
C*** 5/29/80 ***
C*** SUBROUTINE TO INPUT COMMAND STRING VIA SIGNIFICANT EVENTS ***
        SUBROUTINE LNK01
        COMMON /RCV/ IC(2),IP(2),ICMD(128,2),MXC(2),LEN(20,2),NSIZ(2)
        COMMON /LNKTSK/ LNKCMD,LNKARG(5),LNKFLG(2)
        DATA ISYN/"026/,ISTX/"002/,IETX/"003/,IEOT/"004/
        IL=LNKARG(1)
        IERR=0
        JFLG=0
        IP(IL)=0
C*** CHECK FOR FILLED FIFO ***
        CALL CHKRCV(ISTAT,IC(IL))
        IF(ISTAT.NE.0) GO TO 2000
C*** FIFO FILLED- READ IN UNTIL ETX-EOT ***
        ILAST=128-NSIZ(IL)+1
C*** IFLG=1,2,3. 1-COMMAND,2-ETX,3-EOT/STX ***
        DO 600 I=1,ILAST,NSIZ(IL)
            IHI =I+NSIZ(IL)-1
            CALL MRCV(ICMD(I,IL),1,NSIZ(IL),IC(IL))
            IF(I.NE.1) GO TO 200
            IF(ICMD(1,IL).NE.ISYN) GO TO 800
            IFLG=3
            IP(IL)=2
200         IF(IP(IL).GT.IHI) GO TO 600
            GO TO (300,400,500)IFLG
C*** HUNTING FOR COMMAND WORD ***
300         NCMD=ICMD(IP(IL),IL)
            IF(NCMD.LE.0.OR.NCMD.GT.MXC(IL)) GO TO 700
            IFLG=2
            IP(IL)=IP(IL)+LEN(NCMD,IL)+1
            GO TO 200
C*** HUNTING FOR ETX ***
400         IF(ICMD(IP(IL),IL).NE.IETX) GO TO 800
            IFLG=3
            IP(IL)=IP(IL)+1
            GO TO 200
C*** HUNTING FOR STX OR EOT ***
500         IF(ICMD(IP(IL),IL).EQ.IEOT) GO TO 900
            IF(ICMD(IP(IL),IL).NE.ISTX) GO TO 800
            IFLG=1
            IP(IL)=IP(IL)+1
            GO TO 200
600         CONTINUE
C*** ARRAY OVERFLOW BEFORE EOT ***
        IERR=1
        GO TO 1000
C*** COMMAND OUT OF RANGE ERROR ***
700     IERR=2
        GO TO 1000
C*** ILLEGAL CHARACTER ERROR ***
800     IERR=3
        GO TO 1000
C*** COMMAND PRESENT - NO ERRORS ***
900     JFLG=1
1000    IP(IL)=2
C*** FILL IN LINK ARGUMENTS ***
2000    LNKARG(2)=JFLG
```

LNK01.FTN;1                    SPOOL DATE: 09-FEB-81

```
        LNKARG(3)=IERR
        RETURN
        END
```

LNK02.FTN;1                    SPOOL DATE: 09-FEB-81

```
C*** SUBROUTNE LNK02.FTN ***
C*** J. E. HORN ***
C*** 5/29/80 ***
C*** SUBROUTINE TO SEND COMMANDS STRINGS VIA SIGNIFICANT EVENTS ***
        SUBROUTINE LNK02
        DIMENSION XARG(50)
        COMMON /SND/IC(2),IP(2),ICMD(128,2),MXC(2),LEN(20,2),NSIZ(2)
        COMMON /ARG/ NCMD(10),IARG(100)
        COMMON /LNKTSK/ LNKCMD,LNKARG(5),LNKFLG(2)
        EQUIVALENCE (XARG(1),IARG(1))
        DATA ISYN /"26/,ISTX/2/,IETX/3/,IEOT/4/
        N=LNKARG(1)
        IL=LNKARG(2)
        IERR=0
        ICMD(1,IL)=ISYN
C*** COMPUTE LENGTH AND NUMBER OF BLOCKS ***
        ILEN=2+3*N
        DO 100 I=1,N
100        ILEN=ILEN+LEN(NCMD(I),IL)
        NBLK=(ILEN-1) /NSIZ(IL)+1
C*** FILL UP ICMD ARRAY ***
        IP(IL)=2
        IAP=1
        DO 300 I=1,N
           ICMD(IP(IL),IL)=ISTX
           IP(IL)=IP(IL)+1
           IF(NCMD(I).GT.MXC(IL)) GO TO 1000
           ICMD(IP(IL),IL)=NCMD(I)
           IP(IL)=IP(IL)+1
C*** FILL IN COMMAND ARGUMENTS ***
           IF(LEN(NCMD(I),IL).EQ.0) GO TO 250
           DO 200 J=1,LEN(NCMD(I),IL)
              IF (IP(IL).GT.126) GO TO 1100
              ICMD(IP(IL),IL)=IARG(IAP)
              IP(IL)=IP(IL)+1
              IAP=IAP+1
200           CONTINUE
250        ICMD(IP(IL),IL)=IETX
           IP(IL)=IP(IL)+1
300     CONTINUE
C*** EOT - SEND COMMAND ***
        ICMD(IP(IL),IL)=IEOT
        CALL MSND(ICMD(1,IL),NBLK,NSIZ(IL),IC(IL))
        GO TO 2000
C*** IERR=1 - ILLEGAL COMMAND ***
1000    IERR=1
        GO TO 2000
C*** IERR=2 - ARRAY OVERFLOW **
1100    IERR=2
C*** SET LINK ARGUMENTS ***
2000    LNKARG(3)=IERR
        RETURN
        END
```

LNK03.FTN;2                    SPOOL DATE: 09-FEB-81

```
C*** SUBROUTINE LNK03.FTN ***
C*** J. E. HORN ***
C*** 5/27/80 ***
C*** SUBROUTINE TO RECEIVE WAVEFORM VIA SIGNIFICANT EVENTS ***
      SUBROUTINE LNK03
      COMMON /WF/ IW(1024),R(2),IWF
      COMMON /RCV/ IC(2),IP(2),ICD(128,2),MXC(2),L(20,2),NSIZ(2)
      DATA NBLK/16/
C*** RECEIVE WAVEFORM ***
      CALL MRCV(IW,NBLK,NSIZ(2),IC(2))
      RETURN
      END
```

LNK04.FTN;2                    SPOOL DATE: 09-FEB-81

```
C*** SUBROUTINE LNK04.FTN ***
C*** J. E. HORN ***
C*** 5/29/80 ***
C*** SUBROUTINE TO CHECK IF A COMMUNICATION ***
C*** LINK IS ACTIVE (DOES NOT CHECK FOR ERRORS - ONLY ***
C*** THAT SOMETHING ON OTHER END CAN TAKE DATA) ***
C*** IACT=-1 IF CAN'T CLEAR, 0 IF NOT ACTIVE; 1 IF ACTIVE ***
      SUBROUTINE LNK04
      DIMENSION IARR(64)
      COMMON /SND/ IC(2),IP(2),ICMD(128,2),MXC(2),LEN(20,2),NSIZ(2)
      COMMON /LNKTSK/ LNKCMD,LNKARG(5),LNKFLG(2)
      DATA ISYN/"026/,ISTX/"002/,IETX/"003/,IEOT/"004/,WT/5.0/
      IL=LNKARG(1)
C*** CLEAR FIFO ***
      CALL CLRSND(IC(IL))
C*** CHECK STATUS - VERIFY EMPTY ***
      CALL CHKSND(ISTAT,IC(IL))
      IF(ISTAT.NE.3) IACT=-1
      IF(ISTAT.NE.3) GO TO 1000
C*** SEND DATA ***
      CALL MSND (IARR,1,NSIZ(IL),IC(IL))
C*** CHECK STATUS OF LINK ***
      T=SECNDS(0.0)
50    CALL CHKSND (ISTAT,IC(IL))
      IF(ISTAT.EQ.3) GO TO 100
C*** LIMITS LENGTH OF TIME CHECKING STATUS; WT=WAIT TIME IN SECONDS ***
      DEL = SECNDS(T)
      IF(DEL.GE.WT) GO TO 200
      GO TO 50
200   CALL CLRSND(IC(IL))
      IACT=0
      GO TO 1000
100   IACT=1
C*** FILL LINK ARG ***
1000  LNKARG(2)=IACT
      RETURN
      END
```

MAPWLD.FTN;15                    SPOOL DATE: 09-FEB-81

```
C*** SUBROUTINE MAPWLD.FTN ***
C*** J. E. HORN ***
C*** 5/8/80 ***
C*** SUBROUTINE TO MAP EDGE OF WELD ***
        SUBROUTINE MAPWLD(MODE,X2INC,XWB,IERR)
C*** IF MODE = 1, GET VELOCITY; OTHERWISE, DON'T ***
        DIMENSION XX(6)
        COMMON /USM/ X(6)
        COMMON /UT/ U(5)
        COMMON /PRFDAT/ NP,ISIDE,X2EP(2),X2(100),D(100)
        COMMON /PRFCEN/ ICEN,X4REF,X5REF,X3CF(2),XCEN
        DATA X2LIM/2.0/,FR/0.5/
C*** GET CURRENT POSITION AND REMEMBER ***
        CALL USMPOS
        DO 100 I=1,6
100        XX(I)=X(I)
C*** SEE IF WELD BEAD CENTER HAS BEEN FOUND ***
        IF(ICEN.EQ.1) GO TO 200
C*** HAS NOT - ASSUME CONSTANT X3 COORD ***
        X3CF(1)=X(3)
        X3CF(2)=0.0
C*** REMEMBER X2 START POSITION AND CALCULATE X3 START ***
200     X2STRT=X(2)
        X3STRT=X3CF(1)+X3CF(2)*X2STRT
C*** INITIALIZE LOOP COUNTER ***
        I=1
C*** DECIDE WHICH SIDE ***
        ISIDE=1
        IF(X2INC.GT.0.0) ISIDE=2
C*** MOVE TO STARTING POINT AND CENTER SIGNAL ***
        CALL SERVO(X3STRT,3)
        CALL FNDSIG(IERR)
        IF(IERR.NE.0) GO TO 1100
C*** SET DELAY FORWARD BY 2 MICROSECS SO SIGNAL STAYS IN WINDOW ***
        DLY=U(3)+2.0
        CALL DELAY(DLY)
C*** GET INITIAL VOLTAGE ***
        CALL VOLT(VP,VM)
        VM=-VM
300     VMAX=VM
C*** SAVE X2 COORD AND VOLTAGE ***
400     X2LST=X(2)
        VMLST=VM
C*** CALCULATE COORDINATES ***
        XX(2)=X(2)+X2INC
        IF(ABS(XX(2)-X2STRT).GT.X2LIM) GO TO 1000
        XX(3)=X3CF(1)+X3CF(2)*XX(2)
        CALL MOVE(XX)
C*** CHECK PANIC ***
        CALL PANIC(IPNC)
        IF(IPNC.NE.0) GO TO 1200
C*** UPDATE VELOCITY AND MEASURE DISTANCE ***
        IF(MODE.EQ.1) CALL CPLVEL
        CALL MEADIS(D(I))
C*** STORE COORDS ***
        X2(I)=X(2)
        I=I+1
C*** GET VOLTAGE AND CHECK VALUE ***
        CALL VOLT(VP,VM)
```

MAPWLD.FTN;15                    SPOOL DATE: 09-FEB-81

```
              VM=-VM
              IF(VM.GT.VMAX) GO TO 300
              IF(VM.GT.FR*VMAX) GO TO 400
C*** FOUND EDGE OF WELD BEAD - INTERPOLATE ***
              F=(FR*VMAX-VMLST)/(VM-VMLST)
              XWB=X(2)+F*(X(2)-X2LST)
              NP=I-2
C*** IF MORE THAN 4 POINTS, IGNORE LAST 4 ***
              IF(NP.GT.4) NP=NP-4
C*** STORE X2 END POINTS ***
              X2EP(1)=X2(1)
              X2EP(2)=X2(NP)
              RETURN
C*** ERROR - DID NOT FIND WELD BEAD - MOVE TO START ***
1000          IERR=2
1100          CALL SERVO(X2STRT,2)
              CALL SERVO(X3STRT,3)
              RETURN
C*** PANIC ***
1200          IERR=3
              RETURN
              END
```

MEADIS.FTN;2                     SPOOL DATE: 09-FEB-81

```
C*** SUBROUTINE MEADIS.FTN ***
C*** J. E. HORN ***
C*** 5/7/80 ***
C*** SUBROUTINE TO MEASURE DISTANCE ULTRASONICALLY ***
              SUBROUTINE MEADIS(DIS)
              COMMON /VELPAR/ VEL,VSDIST,SSVEL(2)
C*** GET TIME AND CALCULATE DISTANCE ***
              CALL TIME(T)
              DIS=VEL*T*0.5
              RETURN
              END
```

MOVE.FTN;2                       SPOOL DATE: 09-FEB-81

```
C*** SUBROUTINE MOVE.FTN ***
C*** J.E.HORN ***
C*** 10/31/79 ***
C*** SUBROUTINE TO SERVO USM ***
        SUBROUTINE MOVE(XPOS)
        DIMENSION XPOS(6)
        COMMON /USM/ X(6),ISTAT
        COMMON /ARG/ NCMD(10),XARG(50)
C*** SET UP ARGUMENT TO SERVO ****
        DO 100 I=1,6
100         XARG(I)=XPOS(I)
        NCMD(1)=2
        CALL SNDCMD (1,1,IERR)
C*** GET POSITION/STATUS ***
        CALL USMPOS
        RETURN
        END
```

MUX.FTN;3                        SPOOL DATE: 09-FEB-81

```
C*** SUBROUTINE MUX.FTN ***
C*** J.E.HORN ***
C*** 11/6/79 ***
C*** SUBROUTINE TO SELECT UT MUX CHANNEL ***
        SUBROUTINE MUX(C)
        COMMON /ARG/ NCMD(10),XARG(50)
C*** SEND COMMAND TO SELECT CHANNEL ***
        NCMD(1)=2
        XARG(1)=C
        CALL SNDCMD(1,2,IERR)
C*** UPDATE COMMON ***
        CALL UTSTAT
        RETURN
        END
```

PANIC.FTN;1                      SPOOL DATE: 09-FEB-81

```
C*** SUBROUTINE PANIC.FTN ***
C*** J. E  HORN ***
C*** 7/20/80 ***
C*** SUBROUTINE TO CHECK IF PANIC BUTTON PUSHED ***
        SUBROUTINE PANIC(IPNC)
C*** GET BOX SWITCHES ***
        CALL BOXSW(IFUN,IAX,IDIR,IBUT)
        IPNC=IBUT
        RETURN
        END
```

PARINT.FTN;3                                    SPOOL DATE: 09-FEB-81

```fortran
C*** SUBROUTINE PARINT.FTN ***
C*** J. E. HORN ***
C*** 5/20/80 ***
C*** SUBROUTINE TO CALCULATE WHERE A PARABOLA AND A LINE INTERSECT ***
      SUBROUTINE PARINT(X,Y,T,A,X1,X2,XI,YI,ICODE)
      DIMENSION A(3),XR(2),DEL(2)
C*** X,Y = COORDS OF POINT OF LINE ***
C*** T = ANGLE IN DEGREES OF LINE ***
C*** A = PARABOLA COEFFICIENTS ***
C*** X1,X2 = X BOUNDARIES ***
C*** XI,YI = COORDS OF INTERSECTION POINT ***
C*** ICODE = 0 IF VALID POINT ***
C***         1 IF OUT OF RANGE OF X BOUNDARIES ***
C***         2 IF NO INTERSECTION ***
      DATA SF/57.2957795/
      ICODE=0
C*** CHECK IF VERTICAL LINE (T=+-90 DEGREES) ***
      IF(ABS(T).NE.90.0) GO TO 100
      XI=X
      YI=A(1)+A(2)*XI+A(3)*XI*XI
C*** CHECK IF WITHIN X LIMITS ***
      ICODE=1
      IF(XI.GE.X1.AND.XI.LE.X2) ICODE=0
      IF(XI.GE.X2.AND.XI.LE.X1) ICODE=0
      RETURN
C*** CALCULATE SLOPE (S) AND INTERCEPT (B) ***
100   S=TAN(T/SF)
      B=Y-S*X
C*** CALCULATE RADICAL OF QUADRATIC ***
      R=(A(2)-S)*(A(2)-S)-4.0*A(3)*(A(1)-B)
      IF(R.GE.0) GO TO 200
C*** IMAGINARY ROOTS - NO INTERSECTION ***
      ICODE=2
      RETURN
C*** CALCULATE ROOTS ***
200   R=SQRT(R)
      XR(1)=(S-A(2)+R)/(2.0*A(3))
      XR(2)=(S-A(2)-R)/(2.0*A(3))
C*** SEE WHICH (IF ANY) ROOT IS IN RANGE ***
      DO 300 I=1,2
         IF(XR(I).GE.X1.AND.XR(I).LE.X2) GO TO 400
         IF(XR(I).GE.X2.AND.XR(I).LE.X1) GO TO 400
C*** NOT IN RANGE - CALCULATE DELTA ***
         DEL(I)=AMIN1(ABS(XR(I)-X1),ABS(XR(I)-X2))
300   CONTINUE
C*** NEITHER ROOT IN RANGE - SEE WHICH IS CLOSER ***
      I=1
      IF(DEL(2).LT.DEL(1)) I=2
      ICODE=1
C*** CALCULATE Y INTERSECTION VALUE ***
400   XI=XR(I)
      YI=S*XI+B
      RETURN
      END
```

PEAK.FTN;20                         SPOOL DATE: 09-FEB-81

```
C*** SUBROUTINE PEAK.FTN ***
C*** J. E. HORN ***
C*** 4/17/80 ***
C*** SUBROUTINE TO PEAK ULTRASONIC SIGNAL ON USM ***
        SUBROUTINE PEAK(IAX,IERR)
        DIMENSION DX(6),DXLIM(6),XSTRT(6)
        REAL*8 C(5),B(3),A(3),XX,ARG,VSIG
        COMMON /USM/ X(6)
C*** DX = INCREMENT TO MOVE EACH AXIS ***
        DATA DX/0.02,0.002,0.002,0.2,0.3,0.0/
C*** DXLIM = MAX MOVEMENT FOR EACH AXIS ***
        DATA DXLIM/2.0,0.2,0.2,5.0,8.0,0.0/
C*** VDEL = DELTA VOLTAGE FROM REF ***
C*** VMIN = MINIMUM VOLTAGE ***
        DATA VDEL/0.08/,VMIN/0.3/
C*** SAVE START POSITION ***
50      CALL USMPOS
        DO 100 I=1,6
100        XSTRT(I)=X(I)
C*** ZERO FIT ARRAYS ***
        DO 200 I=1,5
           IF(I.LE.3) B(I)=0.0
200        C(I)=0.0
C*** INITIALIZE PEAKING PARAMETERS ***
        IPASS=0
        DEL=-DX(IAX)
        IERR=0
C*** GET VOLTAGE AND CHECK IF OK IF PASS=0 ***
300     CALL VOLT(VP,VM)
        VREF=-VM
        IF(IPASS.EQ.0.AND.VREF.LT.VMIN) GO TO 1000
C*** MOVE TO NEXT POSITION AND GET VOLTAGE ***
400     XPOS=X(IAX)+DEL
        IF(ABS(XPOS-XSTRT(IAX)).GT.DXLIM(IAX)) GO TO 1100
        CALL SERVO(XPOS,IAX)
C*** CHECK PANIC ***
        CALL PANIC(IPNC)
        IF(IPNC.NE.0) GO TO 1200
        XX=X(IAX)
        CALL VOLT(VP,VM)
        IF(-VM.LE.0.99) GO TO 450
C*** VOLTAGE TOO LARGE - ADJUST ATTENUATION AND START OVER ***
        CALL AUTATN
        GO TO 50
450     VSIG=-VM
C*** ACCUMULATE VALUES IN FIT ARRAYS ***
        ARG=1.0
        DO 500 I=1,5
           C(I)=C(I)+ARG
500        ARG=ARG*XX
        ARG=VSIG
        DO 600 I=1,3
           B(I)=B(I)+ARG
600        ARG=ARG*XX
C*** COMPARE VOLTAGE TO REFERENCE ***
        IF(-VM+VDEL.GT.VREF) GO TO 400
C*** SWITCH DIRECTION IF PASS=0; FIT IF PASS=1 ***
        IF(IPASS.EQ.1) GO TO 700
        IPASS=1
```

PEAK.FTN;20                    SPOOL DATE: 09-FEB-81

```
              DEL=-DEL
              GO TO 300
C*** PERFORM FIT ***
700       CALL FIT(XPEAK,C,B,A)
          WRITE(5,1) IAX,XPEAK
1         FORMAT(' PEAK FOR AXIS',I3,' :',G12.5)
C*** MOVE TO LOCATION OF PEAK ***
          XSTRT(IAX)=XPEAK
          CALL MOVE(XSTRT)
          RETURN
C*** VOLTAGE ERROR ***
1000      IERR=1
          RETURN
C*** LIMIT ERROR - MOVE BACK TO STARTING POSITION ***
1100      IERR=2
          CALL MOVE(XSTRT)
          RETURN
C*** PANIC ERROR ***
1200      IERR=3
          RETURN
          END
```

PREPR.FTN;1                    SPOOL DATE: 09-FEB-81

```
C*** SUBROUTINE PREPR.FTN ***
C*** J. E. HORN ***
C*** 6/13/80 ***
C*** SUBROUTINE TO PRESET POSITION REGISTER ***
          SUBROUTINE PREPR(XPS,IAX)
          DIMENSION XPS(6),XARG(50)
          COMMON /ARG/ NCMD(10),IARG(100)
          EQUIVALENCE (IARG(1),XARG(1))
C*** SET UP COMMAND ***
          NCMD(1)=6
          DO 100 I=1,6
100          XARG(I)=XPS(I)
          IARG(13)=IAX
C*** SEND COMMAND ***
          CALL SNDCMD(1,1,IERR)
C*** UPDATE POSITION ***
          CALL USMPOS
          RETURN
          END
```

PRFEDG.FTN;14                SPOOL DATE: 09-FEB-81

```fortran
C*** SUBROUTINE PRFEDG.FTN ***
C*** J. E. HORN ***
C*** 5/20/80 ***
C*** SUBROUTINE TO PROFILE WELD BEAD EDGE DETAIL AROUND PIPE ***
      SUBROUTINE PRFEDG(V1,V2,IERR)
C*** V1,V2 = UPPER AND LOWER VOLTAGE CUTOFFS ***
C*** IERR = 0 IF NO ERROR; NON-ZERO IF ERROR ***
      DIMENSION XPOS(6),X3CF(2)
      COMMON /USM/ X(6)
      COMMON /UT/ U(5)
      COMMON /EDGDAT/ NP,X1PAR(2),X2INC,FV(2),X2EDG(256)
      DATA X2L1/2.0/,X2L2/0.50/
C*** SET SCAN PARAMETERS ***
      X1CEN=X1PAR(1)
      X1INC=X1PAR(2)
      X1STRT=X1CEN-X1INC*(NP/2)
C*** GET COORDS ***
      CALL USMPOS
      XPOS(1)=X1STRT
      XPOS(2)=X(2)
      CALL COORD(XPOS,X3CF,IERR)
      IF(IERR.NE.0) GO TO 1000
C*** MOVE TO START POSITION ***
      CALL MOVE(XPOS)
C*** CENTER AND SCALE SIGNAL ***
      CALL AUTATN
      CALL CENSIG(IERR)
      IF(IERR.NE.0) GO TO 4000
C*** INCREASE DELAY BY 2 MICROSECS SO SIGNAL STAYS IN WINDOW ***
      D=U(3)+2.0
      CALL DELAY(D)
C*** MAKE SURE AMPLITUDE ABOVE V1 AT START ***
      CALL AMP(V)
      IF(V.LE.V1) GO TO 2000
C*** AT START POSITION, FIND EDGE ***
      CALL FNDEDG(V1,V2,X2INC,X2L1,X3CF,X2VAL,IERR)
      IF(IERR.NE.0) GO TO 3000
C*** START FIND EDGE LOOP ***
      DO 100 I=1,NP
         XPOS(1)=X1STRT+(I-1)*X1INC
         XPOS(2)=X(2)
         CALL COORD(XPOS,X3CF,IERR)
         IF(IERR.NE.0) GO TO 1000
C*** MOVE TO POSITION ***
         CALL MOVE(XPOS)
C*** GET EDGE ***
         CALL FNDEDG(V1,V2,X2INC,X2L2,X3CF,X2VAL,IERR)
         IF(IERR.NE.0) GO TO 3000
         X2EDG(I)=X2VAL
100   CONTINUE
      RETURN
C*** ERROR CONDITIONS ***
1000  WRITE(5,1) IERR
1     FORMAT(' ERROR',I4,' IN COORD')
      RETURN
2000  WRITE(5,2)
2     FORMAT(' ERROR - VOLTAGE TOO SMALL AT START')
      RETURN
3000  WRITE(5,3) IERR
3     FORMAT(' ERROR',I4,' IN FNDEDG')
      RETURN
4000  WRITE(5,4) IERR
4     FORMAT(' ERROR',I4,' IN CENSIG')
      RETURN
      END
```

PROSCA.FTN;13                          SPOOL DATE: 09-FEB-81

```fortran
C*** SUBROUTINE PROSCA.FTN ***
C*** J. E. HORN ***
C*** 6/25/80 ***
C*** SUBROUTINE TO SCAN USING SECTOR PROFILE DATA AND VELOCITY
C*** COMPENSATION ***
        SUBROUTINE PROSCA(NP1,X1C,X1I,X2I)
C*** NP1 = NUMBER OF AXIS 1 POINTS ***
C*** X1C = AXIS 1 CENTER POSITION ***
C*** X1I = AXIS 1 INCREMENT ***
C*** X2I = AXIS 2 INCREMENT (IS ZERO FOR A LINE SCAN) ***
        DIMENSION XP(6)
        COMMON /USM/ X(6)
        COMMON /UT/ U(5)
        COMMON /WF/ IW(1024),R(2),IWF
        COMMON /HDR/ HD(128)
        COMMON /VELPAR/ CVEL,VSDIST,SSV(2)
        COMMON /GEOPAR/ ITYP,AR,PL,DE
        DATA NPX2/10/
C*** INITIALIZE PARAMETERS ***
        NP2=NPX2
        IF(X2I.EQ.0.0) NP2=1
        X1S=X1C-X1I*(NP1/2)
C*** SET UP HEADER ***
        HD(26)=SSV(ITYP)
        HD(27)=AR
        HD(28)=PL
        HD(29)=DE
C*** CALCULATE TIME AND REMEMBER DELAY FOR DELAY CORRECTION ***
        CALL CPLVEL
        TPL=2.0*PL/CVEL
        DSTRT=U(3)
C*** START SCAN ***
        DO 200 I=1,NP1
C*** GET COUPLANT VELOCITY ***
        CALL CPLVEL
        HD(25)=CVEL
C*** SET DELAY BASED ON VELOCITY ***
        T=2.0*PL/CVEL
        D=DSTRT+(T-TPL)
        CALL DELAY(D)
C*** CALCULATE INCIDENT ANGLE ***
        CALL SNELL(AR,AI,SSV(ITYP),CVEL,IERR)
C*** CALCULATE AXIS 1 POSITION ***
        X1=X1S+X1I*(I-1)
        XP(1)=X1
        XP(2)=X(2)
C*** SET GEOMETRY FOR DESIRED PARAMETERS ***
        CALL SETGEO(XP,AI,PL,DE,IERR)
        IF(IERR.EQ.0) GO TO 100
        IF(IERR.LT.8) GO TO 500
C*** EITHER X2 OUT OF RANGE OR PAST PARABLOA SADDLE POINT ***
        WRITE(5,1) IERR,XP(1)
1       FORMAT(' CONDITION',I5,' AT X1 =',F8.3)
C*** MOVE TO FIRST SCAN POSITION ***
100     XP(2)=XP(2)-X2I*(NP2/2)
        X2S=XP(2)
        CALL MOVE(XP)
C*** PERFORM AXIAL SCAN ***
        R(2)=FLOAT(I)
```

PROSCA.FTN;13                           SPOOL DATE: 09-FEB-81

```
              CALL SCAN(2,X2S,X2I,NP2,1,1,IERR)
              IF(IERR.NE.0) GO TO 600
200           CONTINUE
              RETURN
C*** FATAL ERROR ***
500           WRITE(5,2) IERR
2             FORMAT(' FATAL ERROR',I5,' IN SETGEO')
              RETURN
C*** ERROR IN SCAN ***
600           WRITE(5,3) IERR
3             FORMAT(' ERROR',I5,' IN SCAN')
              RETURN
              END
```

RCVWF.FTN;5                             SPOOL DATE: 09-FEB-81

```
C*** SUBROUTINE RCVWF.FTN ***
C*** J.E. HORN ***
C*** 11/6/79 ***
C*** SUBROUTINE TO GET WAVEFORM FROM UT SYSTEM ***
              SUBROUTINE RCVWF
              COMMON /ARG/ NCMD(10),XARG(50)
C*** SEND COMMAND REQUEST WAVEFORM ***
100           NCMD(1)=10
              CALL SNDCMD(1,2,IERR)
C*** WAIT FOR RESPONSE COMMAND ***
200           CALL CMDINP(2,IFLG,IERR)
              IF(IERR.NE.0) GO TO 100
              IF(IFLG.EQ.0) GO TO 200
C*** DECODE COMMAND ***
              CALL CMDDEC(2,IERR)
              IF(NCMD(1).NE.2.OR.IERR.NE.0) GO TO 100
C*** RECEIVE WAVEFORM ***
              CALL GETWF
              RETURN
              END
```

READWF.FTN;5                    SPOOL DATE: 09-FEB-81

```
C*** SUBROUTINE READWF.FTN ***
C*** J.E. HORN ***
C*** 2/6/80 ***
C*** SUBROUTINE TO READ IN WAVEFORM 512 LONG FROM FILE ***
        SUBROUTINE READWF (IWF,ITYP,LUN,IERR)
C*** ITYP = 0 FOR REAL WAVEFORMS OF LENGTH 512 (TEK 7912) ***
C***      = 1 FOR INTEGER WAVEFORMS OF LENGTH 512 (BIO 8100) ***
C***      = 2 FOR INTEGER WAVEFORMS OF LENGTH 1024 (BIO 8100) ***
        DIMENSION IW(1024)
        COMMON /WF/ W(1024)
        COMMON /HDR/ HD(128)
        EQUIVALENCE (W(1),IW(1))
        IERR=0
        IF(ITYP.EQ.1) GO TO 100
C*** REAL WAVEFORMS ***
        NREC=5*IWF-4
        N=4
        GO TO 200
C*** INTEGER WAVEFORMS ***
100     NREC=3*IWF-2
        N=2
C*** READ IN HEADER AND WAVEFORM ***
200     READ(LUN'NREC,END=1000,ERR=1000)HD
        DO 300 I=1,N
        K2=128*I
        K1=K2-127
        READ(LUN'NREC+I,END=1000,ERR=1000)(W(K),K=K1,K2)
300     CONTINUE
C*** IF REAL, RETURN ***
        IF(ITYP.EQ.0) RETURN
C*** CONVERT TO REAL USING VSF(HD(14)) AND ATT(HD(12)) ***
C*** DO BACKWARDS SO WON'T WIPE OUT DATA ***
        N=512
        IF(ITYP.EQ.2) N=1024
        DO 400 I=N,1,-1
        W(I)=FLOAT(IW(I))/128.0*HD(14)*EXP(HD(12)/8.68589)
400     CONTINUE
        RETURN
C*** ERROR IN READING FILE ***
1000    IERR=1
        RETURN
        END
```

RECTFY.FTN;6                    SPOOL DATE: 09-FEB-81

```
C*** SUBROUTINE RECTFY.FTN ***
C*** J.S. EMMONS ***
C*** 6/9/78 ***
C*** SUBROUTINE TO COMPUTE PV SIGNAL AND MAX FROM RF WAVEFORM ***
        SUBROUTINE RECTFY(X,IPTS,RX,RMAX)
        DIMENSION X(1024),RX(256)
        RMAX=0.0
        N=IPTS/4
        DO 200 I=1,N
          JH=I*4
          JL=JH-3
          RX(I)=0.0
          DO 100 J=JL,JH
100         RX(I)=AMAX1(RX(I),ABS(X(J)))
          RMAX=AMAX1(RMAX,RX(I))
200     CONTINUE
        RETURN
        END
```

SCAN.FTN;11                    SPOOL DATE: 09-FEB-81

```fortran
C*** SUBROUTINE SCAN.FTN ***
C*** J. E. HORN ***
C*** 5/17/80 ***
C*** SUBROUTINE TO PERFORM SINGLE AXIS SCAN ***
        SUBROUTINE SCAN(IAX,XSTRT,XINC,NP,INDX,LUN,IERR)
        DIMENSION XX(6),COEF(2)
        COMMON /USM/ X(6)
        COMMON /WF/ IW(1024),R(2),IWF
        COMMON /HDR/ HD(128)
C*** INITIALIZE PARAMETERS ***
        IERR=0
        R(INDX)=1.0
        CALL USMPOS
        DO 100 I=1,6
100        XX(I)=X(I)
C*** START SCAN LOOP ***
        DO 1000 I=1,NP
        XX(IAX)=XSTRT+(I-1)*XINC
C*** MOVE TO SCAN POSITION ***
        CALL MOVE(XX)
C*** CHECK PANIC ***
        CALL PANIC(IERR)
        IF(IERR.EQ.0) GO TO 200
        RETURN
C*** DIGITIZE AND RECEIVE WAVEFORM ***
200        CALL AUTATN
        CALL DIG
C** CREATE HEADER AND STORE WAVEFORM ***
        CALL CREHDR
        IWF=IWF+1
        CALL WRITWF (IWF,2,LUN,IW,HD)
        R(INDX)=R(INDX)+1.0
1000       CONTINUE
        RETURN
        END
```

SECTOR.FTN;7                      SPOOL DATE: 09-FEB-81

```
C*** SUBROUTINE SECTOR.FTN ***
C*** J. E. HORN ***
C*** 5/20/80 ***
C*** SUBROUTINE TO GET SECTOR DATA AT 3 POINTS ***
        SUBROUTINE SECTOR(IERR)
        DIMENSION X1POS(3),IORD(3)
        COMMON /USM/ X(6)
        COMMON /SECDAT/ NSIDE,X1(3),X4(3),X5(3),COEF(2,3),X2CEN(3),
     .  V(3),X2END(2,3),PARCF(3,3)
        COMMON /PRFDAT/ NP,ISIDE,X2EP(2),X2(100),D(100)
        COMMON /PRFCEN/ ICEN,X4REF,X5REF,X3CF(2),XCEN
        COMMON /PRFFIT/ A(3)
        DATA IORD/2,3,1/,X2INC/0.025/,DEL2/2.0/,X2MAP/0.05/,MODE/1/
C*** TELL OPERATOR THAT MUST BE OVER WELD ***
        WRITE(5,1)
1       FORMAT(' *** TRANSDUCER MUST BE OVER WELD ***',/,
     .  ' HIT RETURN TO PROCEED:',////)
        READ(5,6) IANS
6       FORMAT(A1)
C*** SAVE BEGINNING X2 CENTER POSITION ***
        CALL USMPOS
        X2C=X(2)
C*** START LOOP TO DO THREE POSITIONS ***
        DO 500 I=1,3
           ISEC=IORD(I)
C*** MOVE TO X2 AND X1 POSITIONS ***
           CALL SERVO(X2C,2)
           CALL SERVO(X1(ISEC),1)
C*** FIND CENTER OF WELD ***
           CALL WLDCEN(DEL2,X2INC,IERR)
           IF(IERR.NE.0) GO TO 1000
C*** STORE PARAMETERS IN SECDAT COMMON ***
           X4(ISEC)=X4REF
           X5(ISEC)=X5REF
           COEF(1,ISEC)=X3CF(1)
           COEF(2,ISEC)=X3CF(2)
           X2CEN(ISEC)=XCEN
C*** MAP WELD ON DESIRED SIDE ***
C*** NSIDE = 1 - PLUS AXIS 2 SIDE; 2 - MINUS AXIS 2 SIDE ***
           IDIR=NSIDE*2-3
           X2POS=XCEN-DEL2*IDIR
           X3POS=X3CF(1)+X3CF(2)*X2POS
           CALL SERVO(X2POS,2)
           CALL SERVO(X3POS,3)
C*** CENTER AND SCALE SIGNAL ***
           CALL AUTATN
           CALL CENSIG(IERR)
           IF(IERR.NE.0) GO TO 4000
           CALL AMP(V(ISEC))
C*** MAP CURVATURE FOR PARABOLIC FIT ***
           DX2=X2MAP*IDIR
           CALL MAPWLD(MODE,DX2,X2POS,IERR)
           IF(IERR.NE.0) GO TO 2000
C*** FIT MAPWLD DATA IN PRFDAT COMMON ***
           CALL CRVFIT(IERR)
           IF(IERR.NE.0) GO TO 3000
C*** STORE PARAMETERS IN SECDAT COMMON ***
           X2END(1,ISEC)=X2EP(1)
           X2END(2,ISEC)=X2EP(2)
```

SECTOR.FTN;7                    SPOOL DATE: 09-FEB-81

```
              DO 100 J=1,3
100             PARCF(J,ISEC)=A(J)
C*** SET X2C FOR NEXT POINT ***
              X2C=X2CEN(IORD(1))
500           CONTINUE
              RETURN
C*** ERROR CONDITIONS ***
1000          WRITE(5,2) IERR
2             FORMAT(' ERROR',I4,' IN WLDCEN')
              RETURN
2000          WRITE(5,3) IERR
3             FORMAT(' ERROR',I4,' IN MAPWLD')
              RETURN
3000          WRITE(5,4) IERR
4             FORMAT(' ERROR',I4,' IN CRVFIT')
              RETURN
4000          WRITE(5,5) IERR
5             FORMAT(' ERROR',I4,' IN CENSIG')
              RETURN
              END
```

SELBOX.FTN;3                    SPOOL DATE: 09-FEB-81

```
C*** SUBROUTINE SELBOX.FTN ***
C*** J. E. HORN ***
C*** 6/13/80 ***
C*** SUBROUTINE TO SELECT CONTROL BOX ***
              SUBROUTINE SELBOX(IBOX)
              COMMON /ARG/ NCMD(10),IARG(100)
C*** SEND COMMAND TO SELECT BOX ***
              NCMD(1)=11
              IARG(1)=IBOX
              CALL SNDCMD(1,1,IERR)
              RETURN
              END
```

SERVO.FTN;1                     SPOOL DATE: 09-FEB-81

```
C*** SUBROUTINE SERVO.FTN ***
C*** J. E. HORN ***
C*** 3/6/80 ***
C*** SUBROUTINE TO PERFORM SINGLE AXIS SERVO ***
              SUBROUTINE SERVO(XPOS,IAX)
              DIMENSION IARG(100)
              COMMON /ARG/NCMD(10),XARG(50)
              EQUIVALENCE (IARG(1),XARG(1))
C*** SET UP COMMAND AND ARGUMENTS ***
              XARG(1)=XPOS
              IARG(3)=IAX
              NCMD(1)=9
              CALL SNDCMD(1,1,IERR)
C*** GET POSITION/STATUS ***
              CALL USMPOS
              RETURN
              END
```

SETGEO.FTN;11                           SPOOL DATE: 09-FEB-81

```
C*** SUBROUTINE SETGEO.FTN ***
C*** J. E. HORN ***
C*** 6/16/80 ***
C*** SUBROUTINE TO SET GEOMETRY FOR DESIRED PARAMETERS ***
      SUBROUTINE SETGEO(XPOS,AINC,PL,DEDG,ICODE)
C*** XPOS(1) AND (2) ARE AXIS 1 AND 2 POSITIONS FOR CALULATION ***
C*** AINC = INCIDENT ANGLE IN DEGREES ***
C*** PL   = COUPLANT PATH LENGTH IN INCHES ***
C*** DEDG = DISTANCE TO EDGE OF WELD IN INCHES ***
C*** ICODE = 0 IF NO ERRORS ***
C***       = 1 IF OUT OF SECTOR ***
C***       = 2 IF INCIDENT ANGLE OUT OF RANGE ***
C***       = 4 IF PATH LENGTH TOO SMALL ***
C***       = 8 IF X2 OUT OF RANGE ***
C***       =16 IF PAST PARABOLIC SADDLE POINT (USE IDEAL GEOMETRY) ***
      DIMENSION A(3),C(2),XL(2),ALIM(2),XPOS(6)
      COMMON /USM/ X(6)
      COMMON /PRFPAR/ PRDIST,DELANG,DI(2),DPIV,X3PIV
      COMMON /EDGFIT/ ECF(3)
      DATA SF/57.2957795/,PLMIN/0.4/,ALIM/0.0,30.0/
C*** PERFORM INITIAL GEOMETRY CALCULATIONS ***
      CALL INIGEO(XPOS,C,A,XL,ISIDE,ICODE)
      IF(ICODE.EQ.1) RETURN
      ICODE=0
C*** CALCULATE X2 SURFACE COORD FROM DISTANCE TO EDGE ***
      D=ABS(DEDG)*(3-ISIDE*2)
      X2E=ECF(1)+ECF(2)*COS(X(1)/SF)+ECF(3)*SIN(X(1)/SF)
      X2=X2E+D
C*** CHECK IF INCIDENT ANGLE OK ***
      ANG=ABS(AINC)
      IF(ANG.GE.ALIM(1).AND.ANG.LE.ALIM(2)) GO TO 100
      ICODE=2
      RETURN
C*** CHECK IF PATH LENGTH OK ***
100   IF(PL.GE.PLMIN) GO TO 200
      ICODE=4
      RETURN
C*** CHECK IF X2 IN RANGE ***
200   IF(X2.GE.XL(1).AND.X2.LE.XL(2)) GO TO 400
      IF(X2.GE.XL(2).AND.X2.LE.XL(1)) GO TO 400
      ICODE=8
C*** BEGIN CALCULATIONS ***
C*** CALCULATE SURFACE NORMAL AND D AT SURFACE ***
400   ANRM=ATAN(A(2)+2.0*A(3)*X2)*SF
      D=A(1)+A(2)*X2+A(3)*X2*X2
C*** CHECK IF PAST SADDLE POINT ***
      IF(ISIDE.EQ.1.AND.ANRM.LT.0.0) GO TO 500
      IF(ISIDE.EQ.2.AND.ANRM.GT.0.0) GO TO 500
C*** PAST INFLECTION - USE IDEAL GEOMETRY ***
      ICODE=ICODE+16
      ANRM=0.0
      D=PRDIST
C*** CALCULATE INSPECTION ANGLE ***
500   ANG=ANG*(ISIDE*2-3)
      AINSP=ANG-ANRM
C*** CALCULATE BEAM INTERSECTION COORDS ***
      DBI=D-(PL-DI(2))*COS(AINSP/SF)
      X2BI=X2-(PL-DI(2))*SIN(AINSP/SF)
C*** CALCULATE ANGLE OF PROFILE TRANSDUCER AND SIN AND COS ***
```

SETGEO.FTN;11                    SPOOL DATE: 09-FEB-81

```
        TANG=AINSP-(ISIDE*2-3)*DELANG
        CS=COS(TANG/SF)
        SN=SIN(TANG/SF)
C*** CALCULATE X2 AND X3 AT SCANNER ***
        DEL=DI(1)-DBI/CS
        XPOS(2)=(X2BI-(DPIV-DEL-C(1)+X3PIV+DI(1))*SN)/(1.0+C(2)*SN)
        XPOS(3)=DEL+C(1)+C(2)*XPOS(2)
C*** CALCULATE AXIS 5 POSITION ***
        XPOS(5)=-(TANG-XPOS(5))
        RETURN
        END
```

SETSSG.FTN;3                     SPOOL DATE: 09-FEB-81

```
C*** SUBROUTINE SETSSG.FTN ***
C*** J. E. HORN ***
C*** 3/26/80 ***
C*** SUBROUTINE TO SET SCAN SYNC GENERATOR COMPARATOR ***
        SUBROUTINE SETSSG(XCOM,XACT,IAX)
        DIMENSION XARG(50)
        COMMON /ARG/ NCMD(10),IARG(100)
C*** SEND COMMAND TO SET COMPARATOR ***
100     NCMD(1)=13
        XARG(1)=XCOM
        IARG(3)=IAX
        CALL SNDCMD(1,1,IERR)
C*** WAIT FOR RESPONSE WITH ACTUAL VALUE ***
200     CALL CMDINP (1,IFLG,IERR)
        IF(IERR.NE.0) GO TO 100
        IF(IFLG.EQ.0) GO TO 200
C*** DECODE COMMAND AND CHECK IF CORRECT ONE ***
        CALL CMDDEC(1,IERR)
        IF(NCMD(1).NE.3.OR.IERR.NE.0) GO TO 100
C*** SET ACTUAL VALUE ***
        XACT=XARG(1)
        RETURN
        END
```

SNDLNK.FTN;2                     SPOOL DATE: 09-FEB-81

```
C*** SUBROUTINE SNDLNK.FTN ***
C*** J. E. HORN ***
C*** 5/27/80 ***
C*** SUBROUTINE TO EXECUTE LINK COMMANDS ***
        SUBROUTINE SNDLNK
        COMMON /LNKTSK/ LNKCMD,LNKARG(5),LNKFLG(2)
C*** SET EVENT FLAG 1 AND DECLARE SIGNIFICANT EVENT ***
        CALL SETEF(LNKFLG(1))
        CALL DECLAR
C*** WAIT FOR FLAG 2 TO GO HIGH - THEN CLEAR IT ***
        CALL WAITFR(LNKFLG(2))
        CALL CLREF(LNKFLG(2))
        RETURN
        END
```

SNELL.FTN;3                           SPOOL DATE: 09-FEB-81

```fortran
C*** SUBROUTINE SNELL.FTN ***
C*** J.E. HORN ***
C*** 6/18/80 ***
C*** SUBROUTINE TO PERFORM SNELL'S LAW CALCULATIONS ***
      SUBROUTINE SNELL(A1,A2,V1,V2,IERR)
C*** GIVEN A1,V1,V2 - CALCULATE A2 ***
C*** IERR=0 OK
C*** IERR=1 PAST CRITICAL
      DATA SF/57.2957795/
      IERR=0
      SA2=SIN(A1/SF)*V2/V1
      IF(SA2.LT.1.0.AND.SA2.GT.-1.0)GOTO 100
C*** PAST CRITICAL - RETURN ***
      IERR=1
      RETURN
C*** TAKE INVERSE SIN ***
100   CA2=SQRT(1.0-SA2*SA2)
      A2=ATAN(SA2/CA2)*SF
      RETURN
      END
```

SSWP.FTN;1                            SPOOL DATE: 09-FEB-81

```fortran
C*** SUBROUTINE SSWP.FTN ***
C*** J.E. HORN ***
C*** 11/1/79 ***
C*** SUBROUTINE TO START USM SWEEP ***
      SUBROUTINE SSWP (X1,X2,ISPD,IAX)
      DIMENSION IARG(100)
      COMMON /ARG/ NCMD(10),XARG(50)
      EQUIVALENCE (IARG(1),XARG(1))
C*** SET UP COMMAND ***
      NCMD(1)=3
      XARG(1)=X1
      XARG(2)=X2
C*** ISPD=0 --LOW SPEED; ISPD=1 --HIGH SPEED ***
      IARG(5)="200
      IF(ISPD.NE.0) IARG(5)="220
      IARG(6)=IAX
C*** SEND COMMAND ***
      CALL SNDCMD (1,1,IERR)
      RETURN
      END
```

SVOPRO.FTN;5                    SPOOL DATE: 09-FEB-81

```fortran
C*** SUBROUTINE SVOPRO.FTN ***
C*** J. E. HORN ***
C*** 4/21/80 ***
C*** SUBROUTINE TO SERVO AXIS 3 TO PROFILE DISTANCE ***
        SUBROUTINE SVOPRO(XPR3,IERR)
        COMMON /USM/ X(6)
        COMMON /UT/ U(5)
        COMMON /VELPAR/ VEL,VSDIST,SSVEL(2)
        COMMON /PRFPAR/ PRDIST
        IERR=0
C*** UPDATE VELOCITY ***
        CALL CPLVEL
C*** SET MUX TO CHANNEL 2, CENTER SIGNAL, AND CALCULATE DISTANCE ***
        CALL MUX(2,0)
        CALL CENSIG(IERR)
        IF(IERR.NE.0) GO TO 1000
        CALL TIME(T)
        DIST=VEL*T*0.5
        DEL=PRDIST-DIST
C*** CALCULATE DELAY CHANGE ***
        DELD=DEL*2.0/VEL
        DLY=U(3)+DELD
        CALL DELAY(DLY)
C*** MOVE TO POSITION AND CALCULATE AGAIN ***
        X3=X(3)+DEL
        CALL SERVO(X3,3)
        CALL TIME(T)
        DIST=VEL*T*0.5
        DEL=PRDIST-DIST
        XPR3=X(3)+DEL
C*** CENTER SIGNAL ***
        CALL CENSIG(IERR)
1000    RETURN
        END
```

TIMAVG.FTN;1                    SPOOL DATE: 09-FEB-81

```fortran
C*** SUBROUTINE TIMAVG.FTN ***
C*** J. E. HORN ***
C*** 4/4/80 ***
C*** SUBROUTINE TO AVERAGE TIME FROM TRANSMIT ***
        SUBROUTINE TIMAVG(TAVG,NT)
        TAVG=0.0
        DO 100 I=1,NT
          CALL TIME(T)
100       TAVG=TAVG+T
        TAVG=TAVG/FLOAT(NT)
        RETURN
        END
```

TIME.FTN;2                    SPOOL DATE: 09-FEB-81

```fortran
C*** SUBROUTINE TIME.FTN ***
C*** J. E. HORN ***
C*** 4/4/80 ***
C*** SUBROUTINE TO GET TIME FROM TRANSMIT ***
        SUBROUTINE TIME(T)
        DIMENSION XX(2),TT(3)
        COMMON /UT/ U(5)
C*** TAKE 3 TIME READINGS AND FIND MAX AND MIN ***
        IMAX=1
        IMIN=1
        DO 100 I=1,3
           CALL BIORCV(2,XX)
           TT(I)=XX(1)
           IF(TT(I).GT.TT(IMAX)) IMAX=I
           IF(TT(I).LT.TT(IMIN)) IMIN=I
100        CONTINUE
C*** FIND MEDIAN ***
        DO 200 I=1,3
           IF(I.NE.IMAX.AND.I.NE.IMIN) IMED=I
200        CONTINUE
        T=TT(IMED)+U(3)
        RETURN
        END
```

TRGFIT.FTN;4                    SPOOL DATE: 09-FEB-81

```fortran
C*** SUBROUTINE TRGFIT.FTN ***
C*** J. E. HORN ***
C*** 6/16/80 ***
C*** SUBROUTINE TO FIT X2 EDGE PROFILE TO SINE AND COSINE OF X1 ***
C*** X2=A(1)+A(2)*COS(X1)+A(3)*SIN(X1) ***
        SUBROUTINE TRGFIT(IERR)
        REAL*8 A(3),B(3),C(3,3)
        COMMON /EDGDAT/ NP,X1CEN,X1INC,X2INC,FV(2),X2EDG(256)
        COMMON /EDGFIT/ RA(3)
        DATA SF/57.2957795/
C*** CHECK IF ENOUGH POINTS - MUST BE 4 OR MORE ***
        IERR=1
        IF(NP.LT.4) RETURN
        IERR=0
C*** ZERO OUT FIT ARRAYS ***
        DO 100 I=1,3
          B(I)=0.0
          DO 100 J=1,3
            C(I,J)=0.0
100       CONTINUE
C*** ACCUMULATE DATA INTO ARRAYS ***
        X1ST=X1CEN-X1INC*(NP/2)
        DO 200 I=1,NP
          X1=(X1ST+(I-1)*X1INC)/SF
          CS=COS(X1)
          SN=SIN(X1)
          C(1,1)=C(1,1)+1.0
          C(1,2)=C(1,2)+CS
          C(1,3)=C(1,3)+SN
          C(2,2)=C(2,2)+CS*CS
          C(2,3)=C(2,3)+CS*SN
          C(3,3)=C(3,3)+SN*SN
          B(1)=B(1)+X2EDG(I)
          B(2)=B(2)+X2EDG(I)*CS
          B(3)=B(3)+X2EDG(I)*SN
200     CONTINUE
C*** FILL IN OTHER HALF OF C ARRAY ***
        C(2,1)=C(1,2)
        C(3,1)=C(1,3)
        C(3,2)=C(2,3)
C*** PERFORM FIT ***
        CALL FIT3X3(A,B,C)
C*** CONVERT COEFFICIENTS TO SINGLE PRECISION ***
        DO 300 I=1,3
300       RA(I)=SNGL(A(I))
        RETURN
        END
```

TRMMSK.FTN;2                    SPOOL DATE: 09-FEB-81

```fortran
C*** SUBROUTINE TRMMSK.FTN ***
C*** J. E. HORN ***
C*** 11/9/79 ***
C*** SUBROUTINE TO SET TERMINAL MASK ***
        SUBROUTINE TRMMSK(M)
        COMMON /ARG/ NCMD(10),IARG(100)
C*** SET UP AND SEND COMMAND ***
        NCMD(1)=7
        IARG(1)=M
        CALL SNDCMD(1,1,IERR)
        RETURN
        END
```

UPMSK.FTN;2          SPOOL DATE: 09-FEB-81

```fortran
C*** SUBROUTINE UPMSK.FTN ***
C*** J. E. HORN ***
C*** 3/6/80 ***
C*** SUBROUTINE TO UPDATE MASKS ***
      SUBROUTINE UPMSK(IVAL,IOPT)
C*** IVAL=VALUE TO SET MASK TO ***
C*** IOPT=MASK OPTION ***
C*** 0: ALL USM AND UT FUNCTIONS ***
C*** 1-6: USM ***
C*** 7-9: UT ***
C*** 10: USM TERMINAL ***
C*** 11: ALL USM MOTIONS ***
C*** 12: ALL UT FUNCTIONS ***
      COMMON /MASK/ MSK(10)
      I1=1
      I2=10
      IF(IOPT.EQ.0) GO TO 300
      IF(IOPT.EQ.11) GO TO 100
      IF(IOPT.EQ.12) GO TO 200
C*** SINGLE FUNCTION ***
      I1=IOPT
      I2=IOPT
      GO TO 300
C*** ALL USM MOTIONS ***
100   I1=1
      I2=6
      GO TO 300
C*** ALL UT FUNCTIONS ***
200   I1=7
      I2=9
C*** SET MASK VALUES ***
300   DO 400 I=I1,I2
400     MSK(I)=IVAL
C*** SEND MASK COMMANDS ***
      CALL USMMSK(MSK(1))
      CALL UTMSK(MSK(7))
      CALL TRMMSK(MSK(10))
      RETURN
      END
```

USE01.FTN;3          SPOOL DATE: 09-FEB-81

```fortran
C*** SUBROUTINE USE01.FTN ***
C*** J. E. HORN ***
C*** 3/6/80 ***
C*** 'ATT' COMMAND - SET ATTENUATION ***
      SUBROUTINE USE01
      COMMON /UT/ U(5)
      COMMON /MASK/ MSKUSM(6),MSKUT(3),MSKTRM
      COMMON /CSICOM/ ICMD,ISWT,NARG,CARG(10),IFLG(10),MSKCMD(50),MARG
      IF(ISWT.EQ.1) GO TO 100
C*** SET ATTENUATION TO ARG VALUE ***
      A=U(2)
      IF(IFLG(1).EQ.1) A=CARG(1)
      CALL ATTN(A)
      RETURN
C*** AUTO ATTENUATION SET ***
100   IF(MSKUT(2).EQ.1) CALL AUTATN
      RETURN
      END
```

USE02.FTN;5                    SPOOL DATE: 09-FEB-81

```
C*** SUBROUTINE USE02.FTN ***
C*** J.E. HORN ***
C*** 3/6/80 ***
C*** 'BOX' COMMAND - SELECT CONTROL BOX MODE ***
       SUBROUTINE USE02
       COMMON /CSICOM/ ICMD,ISWT,NARG,CARG(10),IFLG(10),MSKCMD(50),MARG
C*** SEE WHICH SWITCH ***
       IF(ISWT.EQ.0) GO TO 100
       GO TO (1000,1000,3000) ISWT
C*** PUT IN BOX MODE ***
100    CALL USEBOX(0)
       RETURN
C*** SELECT WHICH BOX ***
1000   CALL SELBOX(ISWT)
       RETURN
C*** ENTER BOX IN PROFILE MODE ***
3000   CALL USEBOX(1)
       RETURN
       END
```

USE03.FTN;2                    SPOOL DATE: 09-FEB-81

```
C*** SUBROUTINE USE03.FTN ***
C*** J.E. HORN ***
C*** 3/6/80 ***
C*** 'DEL' COMMAND - SET DELAY ***
       SUBROUTINE USE03
       COMMON/UT/ U(5)
       COMMON /CSICOM/ ICMD,ISWT,NARG,CARG(10),IFLG(10),MSKCMD(50),MARG
       IF(ISWT.EQ.1) GO TO 100
C*** SET DELAY TO ARGUMENT ***
       D=U(3)
       IF(IFLG(1).EQ.1) D=CARG(1)
       CALL DELAY (D)
       RETURN
C*** SET DELAY TO CENTER SIGNAL ***
100    CALL CENSIG(IERR)
       IF(IERR.NE.0) WRITE(5,1) IERR
1      FORMAT(' *** ERROR #',I4,' ***')
       RETURN
       END
```

USE04.FTN;6　　　　　　　　　SPOOL DATE: 09-FEB-81

```
C*** SUBROUTINE USE04.FTN ***
C*** J.E. HORN ***
C*** 5/20/80 ***
C*** 'DIG' COMMAND - DIGITIZE WITH PLOT AND STORE OPTIONS ***
C*** ASSUMES DISPLAY IS OFF ***
        SUBROUTINE USE04
        COMMON /WF/ IW(1024),RINDX(2),IWF
        COMMON /HDR/ HD(128)
        COMMON /CSICOM/ ICMD,ISWT,NARG,CARG(10),IFLG(10),MSKCMD(50),MARG
        COMMON /FNAME/ NC,NAME(16)
C*** DIGITIZE AND RECEIVE WAVEFORM ***
        CALL DIG
C*** SEE WHICH SWITCH ***
        IF(ISWT.EQ.0) RETURN
        GO TO (100,200) ISWT
C*** PLOT OPTION ***
100     CALL UTPLOT(RINDX,NAME)
        RETURN
C*** STORE OPTION ***
200     CALL CREHDR
        IWF=IWF+1
        CALL WRITWF(IWF,2,1,IW,HD)
        RINDX(1)=RINDX(1)+1.0
        RINDX(2)=RINDX(2)+1.0
        RETURN
        END
```

USE05.FTN;1　　　　　　　　　SPOOL DATE: 09-FEB-81

```
C*** SUBROUTINE USE05.FTN ***
C*** J.E. HORN ***
C*** 3/6/80 ***
C*** 'DIS' COMMAND - DISABLE MASKS ***
        SUBROUTINE USE05
        COMMON /CSICOM/ ICMD,ISWT,NARG,CARG(10),IFLG(10),MSKCMD(50),MARG
        CALL UPMSK(0,ISWT)
        RETURN
        END
```

USE06.FTN;1　　　　　　　　　SPOOL DATE: 09-FEB-81

```
C*** SUBROUTINE USE06 ***
C*** J.E. HORN ***
C*** 3/6/80 ***
C*** 'ENA' COMMAND - ENABLE MASKS ***
        SUBROUTINE USE06
        COMMON /CSICOM/ ICMD,ISWT,NARG,CARG(10),IFLG(10),MSKCMD(50),MARG
        CALL UPMSK(1,ISWT)
        RETURN
        END
```

USE07.FTN;1　　　　　　　　　SPOOL DATE: 09-FEB-81

```
C*** SUBROUTINE USE07.FTN ***
C*** J.E. HORN ***
C*** 3/6/80 ***
C*** 'ESW' COMMAND - END SWEEP ***
        SUBROUTINE USE07
        CALL ESWP
        RETURN
        END
```

USE08.FTN; 1                    SPOOL DATE: 10-FEB-81

```
C*** SUBROUTINE USE08.FTN ***
C*** J.E. HORN ***
C*** 3/6/80 ***
C*** 'MOV' COMMAND - MOVE USM MOTIONS
        SUBROUTINE USE08
        DIMENSION XX(6)
        COMMON /USM/ X(6)
        COMMON /CSICOM/ ICMD,ISWT,NARG,CARG(10),IFLG(10),MSKCMD(50),MARG
C*** GET CURRENT POSITION ***
        CALL USMPOS
C*** SEE IF SINGLE AXIS OR ALL AXES ***
        IF(ISWT.EQ.0) GOTO 100
C*** SINGLE AXIS ***
        IF(IFLG(1).EQ.0) RETURN
        CALL SERVO(CARG(1),ISWT)
        RETURN
C*** ALL AXES - FILL UP SERVO ARRAY ***
100     DO 200 I=1,6
           XX(I)=X(I)
           IF(IFLG(I).EQ.1) XX(I)=CARG(I)
200        CONTINUE
C*** EXECUTE MOVE ***
        CALL MOVE(XX)
        RETURN
        END
```

USE09.FTN; 2                    SPOOL DATE: 09-FEB-81

```
C*** SUBROUTINE USE09.FTN ***
C*** J.E. HORN ***
C*** 3/6/80 ***
C*** 'MUX' COMMAND - SET MULTIPLEXER CHANNEL ***
        SUBROUTINE USE09
        COMMON /UT/ U(5)
        COMMON /CSICOM/ ICMD,ISWT,NARG,CARG(10),IFLG(10),MSKCMD(50),MARG
        C=FLOAT(ISWT)
C*** SEE IF CHANNEL 3; IF SO, SET WINDOW ***
        IF(C.NE.3) GO TO 100
        WIN=20.48
        CALL BIOCMD(4,WIN)
        GO TO 200
C*** SEE IF 3 LAST CHANNEL ***
100     IF(U(1).NE.3) GO TO 200
        WIN=10.24
        CALL BIOCMD(4,WIN)
C*** SET NEW MUX CHANNEL ***
200     CALL MUX(C)
        RETURN
        END
```

USE10.FTN;5                    SPOOL DATE: 09-FEB-81

```fortran
C*** SUBROUTINE USE10.FTN ***
C*** J. E. HORN ***
C*** 3/6/80 ***
C*** 'PLO' COMMAND - PLOT WAVEFORM ON UT SYSTEM ***
      SUBROUTINE USE10
      COMMON /WF/ IW(1024),RINDX(2),IWF
      COMMON /FNAME/ NC,NAME(16)
      CALL UTPLOT(RINDX,NAME)
      RETURN
      END
```

USE11.FTN;5                    SPOOL DATE: 09-FEB-81

```fortran
C*** SUBROUTINE USE11.FTN ***
C*** J. E. HORN ***
C*** 3/6/80 ***
C*** 'STA' COMMAND - USM POSITION AND UT STATUS ***
      SUBROUTINE USE11
      COMMON /USM/ X(6),ISTAT
      COMMON /UT/ U(5)
C*** UPDATE COMMON AREAS ***
      CALL USMPOS
      CALL UTSTAT
C*** WRITE OUT USM POSITION/STATUS ***
      WRITE(5,1)X,ISTAT
1     FORMAT(' POSITION: ',6F9.4,/,' USM STATUS: ',O8)
C*** WRITEOUT UT STATUS ***
      WRITE(5,2) U
2     FORMAT(' MUX: ',F4.1,2X,'ATT: ',F5.1,2X,'DEL: ',
     .  F5.1,2X,'V SF: ',F6.2,2X,'T SF: ',F6.2)
      RETURN
      END
```

USE12.FTN;6                    SPOOL DATE: 09-FEB-81

```fortran
C*** SUBROUTINE USE12.FTN ***
C*** J. E. HORN ***
C*** 3/6/80 ***
C*** 'STO' COMMAND - STORE UT WAVEFORM ***
      SUBROUTINE USE12
      COMMON /WF/ IW(1024),RINDX(2),IWF
      COMMON /HDR/ HD(128)
C*** CREATE HEADER ***
      CALL CREHDR
C*** CALCULATE WAVEFORM NUMBER ***
      IWF=IWF+1
      CALL WRITWF(IWF,1,1,IW,HD)
      RINDX(1)=RINDX(1)+1.0
      RINDX(2)=RINDX(2)+1.0
      RETURN
      END
```

USE13.FTN;3					SPOOL DATE: 09-FEB-81

```fortran
C*** SUBROUTINE USE13.FTN ***
C*** J.E. HORN ***
C*** 3/6/80 ***
C*** 'SWE' COMMAND - SWEEP USM AXIS ***
      SUBROUTINE USE13
      COMMON /CSICOM/ ICMD,ISWT,NARG,CARG(10),IFLG(10),MSKCMD(50),MARG
C*** ISWT=AXIS ***
C*** CARG(1)=START COORD
C*** CARG(2)=END COORD
C*** CARG(3)=SPEED (0-LOW,1-HI)
      IF(IFLG(1)+IFLG(2)+IFLG(3).NE.3) RETURN
      ISPD=0
      IF(CARG(3).GT.0.5)ISPD=1
      CALL SSWP (CARG(1),CARG(2),ISPD,ISWT)
      RETURN
      END
```

USE14.FTN;3					SPOOL DATE: 09-FEB-81

```fortran
C*** SUBROUTINE USE14.FTN ***
C*** J.E. HORN ***
C*** 3/6/80 **
C*** 'BIO' COMMAND - SEND/RECIEVE BIOMATION COMMANDS ***
      SUBROUTINE USE14
      DIMENSION XX(2)
      COMMON /CSICOM/ ICMD,ISWT,NARG,CARG(10),IFLG(10),MSKCMD(50),MARG
C*** SEE IF SEND COMMAND OR RECEIVE COMMAND ***
      IF(ISWT.GT.8) GO TO 100
C*** SEND COMMAND ***
      IF(ISWT.LE.4.AND.IFLG(1).EQ.0) RETURN
      CALL BIOCMD(ISWT,CARG(1))
      RETURN
C*** RECEIVE COMMAND ***
100   ISWT=ISWT-8
      CALL BIORCV (ISWT,XX)
C*** WRITE OUT RECEIVED INFO ***
      IF(ISWT.EQ.1) WRITE(5,1)XX
1     FORMAT (' + VOLTAGE: ', F8.4,5X,' - VOLTAGE: ',F8.4)
      IF(ISWT.EQ.2) WRITE(5,2)XX(1)
2     FORMAT(' TIME: ',F9.4)
      IF(ISWT.EQ.3)WRITE(5,3)XX
3     FORMAT(' TRIGGER: ',F8.4,5X,' WINDOW: ',F9.4)
      RETURN
      END
```

USE15.FTN;2                    SPOOL DATE: 09-FEB-81

```
C*** SUBROUTINE USE15.FTN ***
C*** J.E. HORN ***
C*** 3/6/80 ***
C*** 'PRE' COMMAND - PRESET POSITION REGISTER ***
        SUBROUTINE USE15
        DIMENSION XPS(6)
        COMMON /USM/ X(6)
        COMMON /CSICOM/ ICMD,ISWT,NARG,CARG(10),IFLG(10),MSKCMD(50),MARG
C*** SEE WHICH SWITCH ***
        IF(ISWT.EQ.7) GO TO 200
        IF(IFLG(1).EQ.0) RETURN
        IAX=ISWT
        DO 100 I=1,6
100        XPS(I)=0.0
        XPS(IAX)=CARG(1)
        GO TO 400
C*** ALL AXES PRESET ***
200     CALL USMPOS
        DO 300 I=1,6
           XPS(I)=X(I)
           IF(IFLG(I).EQ.1) XPS(I)=CARG(I)
300        CONTINUE
        IAX=0
C*** PRESET ***
400     CALL PREPR(XPS,IAX)
        RETURN
        END
```

USE16.FTN;3                    SPOOL DATE: 09-FEB-81

```
C*** SUBROUTINE USE16.FTN ***
C*** J.E. HORN ***
C*** 3/6/80 ***
C*** 'HEL' COMMAND - PRINTS HELP MENU ***
        SUBROUTINE USE16
        COMMON /CSICOM/ ICMD,ISWT,NARG,CARG(10),IFLG(10),MSKCMD(50),MARG
        LUN=5
        IF(ISWT.EQ.0)GO TO 100
C*** ASSIGN DEVICE TO PRINTER ***
        LUN=6
        CALL ASSIGN(6,'LP:')
100     CALL HELP(LUN)
        IF(LUN.EQ.6) CLOSE(UNIT=6)
        RETURN
        END
```

```
C*** SUBROUTINE USE17.FTN ***
C*** J.E. HORN ***
C*** 5/17/80 ***
C*** 'SCA' COMMAND - LINE OR VOLUMETRIC SCAN ***
        SUBROUTINE USE17
        DIMENSION XX(6), COEF(2)
        COMMON /USM/ X(6)
        COMMON /WF/ IW(1024), R(2), IWF
        COMMON /HDR/ HD(128)
        COMMON /CSICOM/ ICMD, ISWT, NARG, CARG(10), IFLG(10), MSKCMD(50), MARG
        DATA NPX2 /10/
C*** GET STARTING POSITION AND STORE IT ***
        CALL USMPOS
        DO 100 I=1,6
100        XX(I)=X(I)
C*** ZERO OPTIONAL HEADER PARAMETERS ***
        DO 200 I=25,29
200        HD(I)=0.0
C*** SEE WHICH SWITCH ***
        GO TO(1000,2000) ISWT
C*** 'LI' SWITCH - LINE SCAN ***
1000    IF(IFLG(1)+IFLG(2)+IFLG(3).NE.3) RETURN
        IAX=1
        XINC=CARG(2)
        NP=IFIX(CARG(3)+0.5)
        XSTRT=CARG(1)-XINC*(NP/2)
        R(1)=1.0
        INDX=2
        CALL SCAN(IAX, XSTRT, XINC, NP, INDX, 1, IERR)
        IF(IERR.NE.0) GO TO 3000
        RETURN
C*** 'VO' SWITCH - VOLUMETRIC SCAN ***
2000    DO 2100 I=1,5
2100       IF(IFLG(I).EQ.0) RETURN
C*** SET UP PARAMETERS ***
        X1INC=CARG(2)
        X2INC=CARG(4)
        NP=IFIX(CARG(5)+0.5)
        X1ST=CARG(1)-X1INC*(NP/2)
        X2ST=CARG(3)-X2INC*(NPX2/2)
        INDX=1
        IAX=2
C** START AXIS 1 SCAN LOOP ***
        DO 2300 I=1,NP
          X1=X1ST+(I-1)*X1INC
          CALL SERVO(X1,1)
C*** DO AXIS 2 SCAN ***
          R(2)=FLOAT(I)
          CALL SCAN(IAX, X2ST, X2INC, NPX2, INDX, 1, IERR)
          IF(IERR.NE.0) GO TO 3000
2300      CONTINUE
        RETURN
C*** ERROR - PRINT OUT ***
3000    WRITE(5,1) IERR
1       FORMAT(' ERROR', I5, ' IN SCAN')
        RETURN
        END
```

USE18.FTN;10                    SPOOL DATE: 09-FEB-81

```
C*** SUBROUTINE USE18.FTN ***
C*** J. E. HORN ***
C*** 3/6/80 ***
C*** 'FIL' COMMAND - CLOSE AND ASSIGN LUN #1 ***
        SUBROUTINE USE18
        COMMON /FNAME/ NC,NAME(16)
        COMMON /WF/ IW(1024),RINDX(2),IWF
        COMMON /CSICOM/ ICMD,ISWT,NARG,CARG(10),IFLG(10),MSKCMD(50),MARG
C*** SEE WHICH SWITCH ***
        ISWT=ISWT+1
        GO TO (1000,2000) ISWT
C*** OPEN WAVEFORM FILE ***
1000    CLOSE (UNIT=1)
        CALL ASIGN(1)
1100    DEFINE FILE 1(5000,256,U,NR1)
        RINDX(1)=1.0
        RINDX(2)=1.0
        IWF=0
        RETURN
C*** CLOSE WAVEFORM FILE ***
2000    CLOSE (UNIT=1)
        NAME(1)='NL'
        NAME(2)=': '
        NC=3
        CALL ASSIGN(1,NAME,NC)
        GO TO 1100
        END
```

USE19.FTN;4                     SPOOL DATE: 09-FEB-81

```
C*** SUBROUTINE USE19.FTN ***
C*** J.E. HORN ***
C*** 4/4/80 ***
C*** 'VEL' COMMAND - GET VELOCITY, CALIBRATE VELOCITY AND PRINT DISTANCE ***
        SUBROUTINE USE19
        COMMON /VELPAR/ VEL,VSDIST,SSVEL(2)
        COMMON /CSICOM/ ICMD,ISWT,NARG,CARG(10),IFLG(10),MSKCMD(50),MARG
C*** SEE WHICH SWITCH ***
        IF(ISWT.EQ.0) GO TO 1000
        GO TO (2000,3000,4000) ISWT
C*** GET COUP VELOCITY AND PRINT COUPLANT AND SS VELOCITIES ***
1000    CALL CPLVEL
1100    WRITE(5,1) VEL,SSVEL
1       FORMAT(' COUPLANT VELOCITY: ',T30,F8.5,/,
     .         ' SHEAR VELOCITY: ',T30,F8.5,/,
     .         ' LONGITUDINAL VELOCITY: ',T30,F8.5)
        RETURN
C*** CALIBRATE VELOCITY ***
2000    CALL VELCAL(VCAL)
        WRITE(5,2)VCAL
2       FORMAT(' CALIBRATION VELOCITY: ',T30,F8.5)
        GO TO 1000
C*** PRINT CURRENT VELOCITY SENSING DISTANCE ***
3000    WRITE(5,3) VSDIST
3       FORMAT (' VELOCITY SENSING DISTANCE: ',T30,F8.4)
        GO TO 1000
C*** SET SHEAR AND LONGITUDINAL VELOCITIES ***
4000    DO 4100 I=1,2
          IF(IFLG(1).EQ.1) SSVEL(I)=CARG(I)
4100    CONTINUE
        GO TO 1100
        END
```

USE20.FTN;3                    SPOOL DATE: 09-FEB-81

```
C*** SUBROUTINE USE20.FTN ***
C*** J. E. HORN ***
C*** 4/17/80 ***
C*** 'PEA' COMMAND - PEAK UT SIGNAL ON USM ***
        SUBROUTINE USE20
        COMMON /CSICOM/ ICMD,ISWT,NARG,CARG(10),IFLG(10),MSKCMD(50),MARG
        IAX=ISWT
        CALL PEAK(IAX,IERR)
        IF(IERR.NE.0) WRITE(5,1) IERR
1       FORMAT(' *** ERROR #',I4,' IN PEAKING ***')
        RETURN
        END
```

USE21.FTN;6                    SPOOL DATE: 09-FEB-81

```
C*** SUBROUTINE USE21.FTN ***
C*** J. E. HORN ***
C*** 5/7/80 ***
C*** 'PRO' COMMAND - EXECUTE PROFILE TRANSDUCER FUNCTIONS ***
        SUBROUTINE USE21
        COMMON /VELPAR/ VEL,VSDIST,SSVEL(2)
        COMMON /PRFPAR/ PRDIST,DELANG,DI(2),DPIV,X3PIV
        COMMON /CSICOM/ ICMD,ISWT,NARG,CARG(10),IFLG(10),MSKCMD(50),MARG
C*** SEE WHICH SWITCH ***
        ISWT=ISWT+1
        GO TO(1000,2000,3000,4000,5000) ISWT
C*** 'DI' SWITCH - PRINT PROFILE DISTANCE ***
1000    WRITE(5,1) PRDIST
1       FORMAT(' PROFILE DISTANCE: ',T20,F9.4)
        RETURN
C*** 'DD' SWITCH - SET DESIRED PROFILE DISTANCE ***
2000    IF(IFLG(1).EQ.1) PRDIST=CARG(1)
        GO TO 1000
C*** 'MD' SWITCH - MEASURE CURRENT PROFILE DISTANCE ***
3000    CALL CPLVEL
        CALL MEADIS(DIS)
        WRITE(5,2) DIS
2       FORMAT(' MEASURED DISTANCE: ',T20,F9.4)
        GO TO 1000
C*** 'SV' SWITCH - SERVO TO DESIRED PROFILE DISTANCE ***
4000    CALL SVOPRO(XPR3,IERR)
        IF(IERR.NE.0) GO TO 4100
        WRITE(5,3) XPR3
3       FORMAT(' AXIS 3 CALCULATED POSITION: ',F9.4)
        GO TO 3000
C*** 'PI' SWITCH - SET PIVOT DIST AND X3 COORD AT PIVOT ***
5000    IF(IFLG(1).EQ.1) DPIV=CARG(1)
        IF(IFLG(2).EQ.1) X3PIV=CARG(2)
        WRITE(5,4) DPIV,X3PIV
4       FORMAT(' PIVOT DISTANCE: ',T20,F9.4,/,
       .       ' X3 COORD AT PIVOT: ',T20,F9.4)
        RETURN
C*** ERROR ***
4100    WRITE(5,5) IERR
5       FORMAT(' *** ERROR #',I4,' ***')
        RETURN
        END
```

```
USE22.FTN;4                    SPOOL DATE: 09-FEB-81

C*** SUBROUTINE USE22.FTN ***
C*** J. E. HORN ***
C*** 5/7/80 ***
C*** 'SIG' COMMAND - GET TIME & VOLT, CENTER & FIND SIGNAL ***
        SUBROUTINE USE22
        COMMON /UT/ U(5)
        COMMON /CSICOM/ ICMD, ISWT, NARG, CARG(10), IFLG(10), MSKCMD(50), MARG
C*** SEE WHICH SWITCH ***
        IF(ISWT.EQ.0) GO TO 1000
        GO TO(2000,3000) ISWT
C*** GET TIME, VOLTAGE, AND AMPLITUDE ***
1000    CALL TIME(T)
        CALL VOLT(VP,VM)
        A=AMAX1(VP,-VM)*U(4)*EXP(U(2)/8.685889638)
        WRITE(5,1) T,VP,VM,A
1       FORMAT(' TIME IN MICROSECONDS: ',F9.4,/,
      . ' + PEAK: ',F8.4,5X,'- PEAK: ',F8.4,/,
      . ' AMP IN VOLTS: ',F9.4)
        RETURN
C*** CENTER SIGNAL ***
2000    CALL CENSIG(IERR)
        IF(IERR.EQ.0) RETURN
C*** ERROR ***
2100    WRITE(5,2) IERR
2       FORMAT(' *** ERROR #',I4,' ***')
        RETURN
C*** FIND SIGNAL ***
3000    CALL FNDSIG(IERR)
        IF(IERR.NE.0) GO TO 2100
        RETURN
        END
```

```
C*** SUBROUTINE USE23.FTN ***
C*** J.E. HORN ***
C*** 5/8/80 ***
C*** 'WEL' COMMAND- FIND CENTER OF WELD BEAD AND PROFILE WELD BEAD ***
        SUBROUTINE USE23
        COMMON /PRFDAT/ NP,ISIDE,X2EP(2),X2(100),D(100)
        COMMON /PRFCEN/ ICEN,X4REF,X5REF,X3CF(2),XCEN
        COMMON /PRFFIT/ A(3)
        COMMON /CSICOM/ ICMD,ISWT,NARG,CARG(10),IFLG(10),MSKCMD(50),MARG
        DATA SF/57.2957795/,MODE/1/
C** SEE WHICH SWITCH ***
        GO TO (1000,2000,3000,4000) ISWT
C*** FIND CENTER OF WELD ***
C*** ARGS ARE DISTANCE FROM CENTER AND STEP INCREMENT ***
1000    IF(IFLG(1)+IFLG(2).NE.2) RETURN
        WRITE(5,1)
1       FORMAT(' USE CONTROL BOX TO MOVE TO CENTER OF WELD:')
        CALL USEBOX
        WRITE(5,2)
2       FORMAT(' *** START WELD BEAD CENTERING ***')
        CALL WLDCEN(CARG(1),CARG(2),IERR)
        IF(IERR.NE.0) GOTO 10000
        WRITE(5,3) XCEN
3       FORMAT(' AXIS 2 WELD CENTER:',F8.4)
        RETURN
C*** MAP WELD BEAD CURVATURE ***
2000    IF(IFLG(1).EQ.0) RETURN
        CALL MAPWLD(MODE,CARG(1),XWB,IERR)
        IF(IERR.NE.0) GO TO 10000
        WRITE(5,4) XWB
4       FORMAT(' AXIS 2 WELD BEAD EDGE:',F8.4)
        RETURN
C*** FIT PROFILE DATA ***
3000    CALL CRVFIT(IERR)
        IF(IERR.NE.0) GO TO 10000
        WRITE(5,5) NP,ISIDE,A
5       FORMAT(' NUMBER OF POINTS:',I5,' FOR SIDE',I3,/,
       .' COEFFICIENTS:',3G14.4)
        RETURN
C*** DUMP FITTED DATA ***
4000    WRITE(5,6)
6       FORMAT(2X,'I',5X,'X2',7X,'D',5X,'FITTED D',3X,'ANG')
        DO 4100 I=1,NP
C*** CALCULATE DISTANCE AND ANGLE ***
        DIST=A(1)+A(2)*X2(I)+A(3)*X2(I)*X2(I)
        ANG=A(2)+2.0*A(3)*X2(I)
        ANG=ATAN(ANG)*SF
        WRITE(5,7) I,X2(I),D(I),DIST,ANG
7       FORMAT(1X,I3,F9.4,2F9.5,F8.3)
4100    CONTINUE
        RETURN
C*** ERROR - PRINT MESSAGE ***
10000   WRITE(5,8)
8       FORMAT(' *** ERROR ***')
        RETURN
        END
```

```
JSE24.FTN;24                    SPOOL DATE: 09-FEB-81

C*** SUBROUTINE USE24.FTN ***
C*** J. E. HORN ***
C*** 5/20/80 ***
C*** SUBROUTINE TO PROFILE SECTOR OF PIPE ***
        SUBROUTINE USE24
        COMMON /CSICOM/ ICMD,ISWT,NARG,CARG(10),IFLG(10),MSKCMD(50),MARG
        COMMON /SECDAT/ NSIDE,X1(3),X4(3),X5(3),COEF(2,3),X2CEN(3),
       . V(3),X2END(2,3),PAR(3,3)
        COMMON /EDGDAT/ IEDG(523)
C*** GET SECTOR DATA ***
        NSIDE=ISWT
        IF(IFLG(1)+IFLG(2).NE.2) RETURN
C*** ZERO EDGE DATA ***
        DO 100 I=1,523
100         IEDG(I)=0
C*** CALCULATE X1 POSITIONS ***
        CARG(2)=ABS(CARG(2))
        X1(1)=CARG(1)-CARG(2)
        X1(2)=CARG(1)
        X1(3)=CARG(1)+CARG(2)
C*** CALL SECTOR TO GET SECDAT COMMON AREA ***
        CALL SECTOR(IERR)
        IF(IERR.EQ.0) RETURN
C*** PRINT ERROR MESSAGE ***
        WRITE(5,1)
1       FORMAT(' ERROR IN SECTOR')
        RETURN
        END

USE25.FTN;1                     SPOOL DATE: 09-FEB-81

C*** SUBROUTINE USE25.FTN ***
C*** J. E. HORN ***
C*** 5/23/80 ***
C*** 'PAU' COMMAND - WAIT FOR OPERATOR TO HIT RETURN ***
        SUBROUTINE USE25
        WRITE(5,1)
1       FORMAT('$HIT ''RETURN'' TO CONTINUE ')
        READ(5,2) IANS
2       FORMAT(A1)
        RETURN
        END
```

USE26.FTN;11　　　　　　　　　　　SPOOL DATE: 09-FEB-81

```
C*** SUBROUTINE USE26.FTN ***
C*** J. E. HORN ***
C*** 6/18/80 ***
C*** 'EDG' COMMAND - PROFILE WELD BEAD EDGE AND FIT DATA ***
        SUBROUTINE USE26
        COMMON /CSICOM/ ICMD,ISWT,NARG,CARG(10),IFLG(10),MSKCMD(50),MARG
        COMMON /SECDAT/ NSIDE,X1(3),X4(3),X5(3),COEF(2,3),X2CEN(3),
       .  V(3),X2END(2,3),PAR(3,3)
        COMMON /EDGDAT/ NP,X1PAR(2),X2INC,FV(2),X2EDG(256)
        COMMON /EDGFIT/ ECF(3)
        DATA DIST/0.75/
C*** SEE WHICH SWITCH ***
        GO TO (1000,2000) ISWT
C*** PROFILE WELD BEAD EDGE ***
C*** CHECK IF SIDE AND VOLTAGES ARE PRESENT ***
1000    IF(NSIDE.NE.1.AND.NSIDE.NE.2) GO TO 10000
        VAVG=(V(1)+V(2)+V(3))/3.0
        IF(VAVG.LE.0.0) GO TO 10100
C*** ALL OK -- CHECK ARGUMENTS ***
        IF(IFLG(1)+IFLG(2)+IFLG(3)+IFLG(4)+IFLG(5).NE.5) RETURN
C*** ZERO EDGE COEFFICIENTS ***
        DO 1100 I=1,3
1100       ECF(I)=0.0
C*** CALCULATE PARAMETERS
        X1PAR(1)=CARG(1)
        X1PAR(2)=ABS(CARG(2))
        NP=MINO(IFIX(CARG(3)+0.5),256)
        V1=CARG(4)*VAVG
        V2=CARG(5)*VAVG
        FV(1)=CARG(4)
        FV(2)=CARG(5)
C*** MOVE IN CLOSER TO WELD ***
        IDIR=NSIDE*2-3
        X2=X2CEN(1)-DIST*IDIR
        CALL SERVO(X2,2)
C*** PROFILE WELD BEAD EDGE AROUND PIPE ***
        X2INC=0.005*IDIR
        CALL PRFEDG(V1,V2,IERR)
        IF(IERR.NE.0) GO TO 10100
        RETURN
C*** FIT EDGE PROFILE DATA ***
2000    CALL TRGFIT(IERR)
        IF(IERR.NE.0) GOTO 10200
        WRITE(5,4) ECF
4       FORMAT(' EDGE COEFFICIENTS : ',3G14.5)
        RETURN
C*** ERROR MESSAGES ***
10000   WRITE(5,1)
1       FORMAT(' NO VALID DATA FROM SECTOR')
        RETURN
10100   WRITE(5,2)
2       FORMAT(' ERROR IN PRFEDG')
        RETURN
10200   WRITE(5,3)
3       FORMAT(' TOO FEW POINTS FOR FIT')
        RETURN
        END
```

```
USE27.FTN;7                    SPOOL DATE: 09-FEB-81

C*** SUBROUTIEN USE27.FTN ***
C*** J. E. HORN ***
C*** 6/18/80 ***
C*** 'DAT' COMMAND - DUMP, STORE, AND READ SECTOR AND EDGE DATA ***
        SUBROUTINE USE27
        COMMON /CSICOM/ ICMD,ISWT,NARG,CARG(10),IFLG(10),MSKCMD(50),MARG
        COMMON /SECDAT/ NSIDE,X1(3),X4(3),X5(3),COEF(2,3),X2CEN(3),
       . V(3),X2END(2,3),PAR(3,3)
        COMMON /EDGDAT/ NP,X1PAR(2),X2INC,FV(2),X2EDG(256)
        COMMON /EDGFIT/ ECF(3)
C*** SEE WHICH SWITCH ***
        IF(ISWT.EQ.0) GO TO 100
        GO TO (1000,2000) ISWT
C*** DUMP DATA IN COMMON AREAS ***
100     WRITE(5,1) NSIDE,X1,X2CEN,X4,X5,V,X2END,COEF,PAR
1       FORMAT(' SECTOR PROFILE DATA FOR SIDE',I4,/,
       . ' AXIS 1 COORDS: ',T18,3F10.3,/,' AXIS 2 CENTER: ',T18,3F10.3,/,
       . ' AXIS 4 COORDS: ',T18,3F10.3,/,' AXIS 5 COORDS: ',T18,3F10.3,/,
       . ' VOLTAGES: ',T18,3F10.3,/,' AXIS 2 LIMITS: ',T18,3(2F8.3,2X),/,
       . ' AXIS 3 COEFS: ',T18,3(2F8.3,2X),/,
       . ' PARABOLIC COEFS: ',3(T18,3(G13.4,5X)/)/)
        WRITE(5,2) NP,X1PAR,X2INC,FV,ECF,(X2EDG(I),I=1,NP)
2       FORMAT(' EDGE PROFILE DATA -',I5,' POINTS',/,
       . ' AXIS 1 CENTER AND INCREMENT: ',T30,2F10.3,/,
       . ' AXIS 2 INCREMENT: ',T30,F10.3,/,
       . ' FRACTIONAL VOLTAGES: ',T30,2F10.3,/,
       . ' EDGE COEFFICIENTS: ',T30,3G13.4,/,
       . ' AXIS 2 EDGE COORDS: ',/,26(1X,10F7.3,/))
        RETURN
C*** STORE DATA IN FILE ***
1000    WRITE(5,3)
3       FORMAT(' ENTER INFORMATION FOR PROFILE DATA FILE: ')
        CALL ASIGN(2)
        DEFINE FILE 2(4,256,U,NR2)
        WRITE(2'1) FLOAT(NSIDE),X1,X4,X5,COEF,X2CEN,V,X2END,PAR
        WRITE(2'2) FLOAT(NP),X1PAR,X2INC,FV,ECF
        WRITE(2'3) (X2EDG(I),I=1,128)
        WRITE(2'4) (X2EDG(I),I=129,256)
1100    CLOSE (UNIT=2)
        WRITE(5,4)
4       FORMAT(' PROFILE FILE CLOSED')
        RETURN
C*** READ DATA FROM FILE AND CLOSE IT ***
2000    WRITE(5,3)
        CALL ASIGN(2)
        DEFINE FILE 2(4,256,U,NR2)
        READ(2'1) RN,X1,X4,X5,COEF,X2CEN,V,X2END,PAR
        NSIDE=IFIX(RN+0.5)
        READ(2'2) RN,X1PAR,X2INC,FV,ECF
        READ(2'3) (X2EDG(I),I=1,128)
        READ(2'4) (X2EDG(I),I=129,256)
        NP=IFIX(RN+0.5)
        GO TO 1100
        END
```

USE28.FTN;16　　　　　　　　　SPOOL DATE: 09-FEB-81

```
C*** SUBROUTINE USE28.FTN ***
C*** J. E. HORN ***
C*** 6/18/80 ***
C*** 'GEO' COMMAND - SUBROUTINE TO PERFORM GEOMETRY CALCULATIONS ***
        SUBROUTINE USE28
        DIMENSION AINC(2),AREF(2),T(2,2),XPOS(6)
        COMMON /CSICOM/ ICMD,ISWT,NARG,CARG(10),IFLG(10),MSKCMD(50),MARG
        COMMON /USM/ X(6)
        COMMON /VELPAR/ CVEL,VSDIST,SSVEL(2)
        COMMON /GEOPAR/ ITYP,AR,PL,DE
        DATA T/'SHEA','R:  ','LONG',':   '/
C*** SEE WHICH SWITCH ***
        IF(ISWT.EQ.0) GO TO 5200
        GO TO(1000,2000,3000,4000,5000) ISWT
C*** 'IN' SWITCH - CALCULATE REFRACTED ANGLE GIVEN INCIDENT ***
1000    IF(IFLG(1).EQ.0) RETURN
        AINC(1)=CARG(1)
        AINC(2)=CARG(1)
1100    WRITE(5,10) AINC(1)
10      FORMAT(9X,'INC ANG: ',F6.2)
        DO 1200 I=1,2
           CALL SNELL(AINC(I),AREF(I),CVEL,SSVEL(I),IERR)
           IF(IERR.EQ.0) WRITE(5,1)T(1,I),T(2,I),AREF(I)
1       FORMAT(1X,2A4,'REF ANG: ',F6.2)
           IF(IERR.NE.0) WRITE(5,2)T(1,I),T(2,I)
2       FORMAT(1X,2A4,'REF ANG: PAST CRITICAL')
1200    CONTINUE
        RETURN
C*** 'RE' SWITCH - CALCULATE INCIDENT ANGLE GIVEN REFRACTED ANGLE ***
2000    IF(IFLG(1).EQ.0) RETURN
        AREF(1)=CARG(1)
        AREF(2)=CARG(1)
        WRITE(5,11) AREF(1)
11      FORMAT(9X,'REF ANG: ',F6.2)
        DO 2100 I=1,2
           CALL SNELL(AREF(I),AINC(I),SSVEL(I),CVEL,IERR)
           WRITE(5,12) T(1,I),T(2,I),AINC(I)
12      FORMAT(1X,2A4,'INC ANG: ',F6.2)
2100    CONTINUE
        RETURN
C*** 'CA' SWITCH - CALCULATE GEOMETRY AT CURRENT POSITION ***
3000    CALL CALGEO(AI,PLEN,DEDG,DCEN,IERR)
        IF(IERR.NE.0) WRITE(5,3) IERR
3       FORMAT(' ERROR CODE: ',I5)
        WRITE(5,4) PLEN,DEDG,DCEN
4       FORMAT(' COUP PATH',6X,'EDG DIS',6X,'CEN DIS',/,
     .  1X,F9.4,6X,F7.4,6X,F7.4)
        AINC(1)=AI
        AINC(2)=AI
        GO TO 1100
C*** 'MO' SWITCH - MOVE USM FOR DESIRED GEOMETRY AT CURRENT X1 POS ***
4000    CALL USMPOS
        XPOS(1)=X(1)
        XPOS(2)=X(2)
C*** CALCULATE INCIDENT ANGLE ***
        CALL SNELL(AR,AI,SSVEL(ITYP),CVEL,IERR)
        CALL SETGEO(XPOS,AI,PL,DE,IERR)
        IF(IERR.NE.0)WRITE(5,5)IERR
5       FORMAT(' ERROR CODE: ',I5)
```

USE28.FTN;16                    SPOOL DATE: 09-FEB-81

```fortran
            WRITE(5,6) XPOS
 6          FORMAT(' CALCULATED POSITION: ',6F8.4,/,
           .'$DO YOU WANT TO MOVE ?')
            CALL ANSWR(IANS)
            IF(IANS.EQ.0) RETURN
            CALL MOVE (XPOS)
            RETURN
C*** 'SE' SWITCH - SET SCAN PARAMETERS ***
 5000       IF(IFLG(1).EQ.0) GO TO 5100
            ITYP=1
            IF(CARG(1).GT.1.5) ITYP=2
 5100       IF(IFLG(2).EQ.1) AR=CARG(2)
            IF(IFLG(3).EQ.1) PL=CARG(3)
            IF(IFLG(4).EQ.1) DE=CARG(4)
 5200       IF(ITYP.EQ.1) WRITE(5,7)
 7          FORMAT(' SHEAR MODE')
            IF(ITYP.EQ.2) WRITE(5,8)
 8          FORMAT(' LONGITUDINAL MODE')
            WRITE(5,9) AR,PL,DE
 9          FORMAT(' REFRACTED ANGLE: ',T25,F6.2,/,' COUPLANT PATH: ',
           .T25,F8.4,/,' EDGE DISTANCE: ',T25,F8.4)
            RETURN
            END
```

USE29.FTN;6                     SPOOL DATE: 09-FEB-81

```fortran
C*** SUBROUTINE USE29.FTN ***
C*** J. E. HORN ***
C*** 6/25/80 ***
C*** 'PSC' COMMAND - PERFORM PROFILE LINE OR VOLUMETRIC SCAN ***
            SUBROUTINE USE29
            COMMON /CSICOM/ ICMD,ISWT,NARG,CARG(10),IFLG(10),MSKCMD(50),MARG
C*** SEE WHICH SWITCH ***
            GO TO (1000,2000) ISWT
C*** 'LI' SWITCH - LINE SCAN ***
 1000       IF(IFLG(1)+IFLG(2)+IFLG(3).NE.3) RETURN
            X1C=CARG(1)
            X1I=CARG(2)
            NP=IFIX(CARG(3)+0.5)
            CALL PROSCA(NP,X1C,X1I,0.0)
            RETURN
C*** 'VO' SWITCH - VOLUMETRIC SCAN ***
 2000       IF(IFLG(1)+IFLG(2)+IFLG(3)+IFLG(4).NE.4) RETURN
            X1C=CARG(1)
            X1I=CARG(2)
            X2I=CARG(3)
            NP=IFIX(CARG(4)+0.5)
            CALL PROSCA(NP,X1C,X1I,X2I)
            RETURN
            END
```

USEBOX.FTN;21                    SPOOL DATE: 09-FEB-81

```
C*** SUBROUTINE USEBOX.FTN ***
C*** J.E. HORN ***
C*** 12/7/79 ***
C*** SUBROUTINE TO INTERPRET CONTROL BOX FOR USM AND UT SYSTEM ***
      SUBROUTINE USEBOX(MODE)
C*** MODE = 0 FOR USUAL BOX MODE ***
C***      = 1 TO CALULATE GEOMETRY (FUNCTION 7, AXIS 3) OR MEASURE
C***          COUPLANT VELOCITY (FUNCTION 7, AXIS 2) ***
C*** IDIR = -1 FOR LONG PRINTOUT ***
C***      = +1 FOR SHORT PRINTOUT ***
      DIMENSION DINC(4),AINC(4),AR(2),IERR(2)
      COMMON /USM/ X(6)
      COMMON /UT/ U(5)
      COMMON /VELPAR/ CVEL,VSD,SSV(2)
      DATA DINC/0.1,1.0,5.0,10.0/,AINC/1.0,2.0,5.0,10.0/,
     . DMIN/0.0/,DMAX/500.0/,AMIN/0.0/,AMAX/79.0/
C*** DISABLE TERMINAL ***
      CALL TRMMSK(0)
C*** MONITOR BOX SWITCHES ***
100   CALL BOXSW(IFUN,IAX,IDIR,IBUT)
C*** SEE IF EXIT (IFUN=8,IBUT=1)
      IF(IFUN.EQ.8.AND.IBUT.EQ.1) GO TO 10000
C*** CHECK FOR NOTHING ***
      IF(IAX.EQ.0) GO TO 100
C*** CHECK FOR MULTIPLEXER ***
      IF(IFUN.EQ.6.AND.IAX.GT.0.AND.IAX.LT.4) GO TO 1000
C*** CHECK FOR DELAY ***
      IF(IAX.EQ.7.AND.IFUN.LE.4) GO TO 2000
C*** CHECK FOR ATTENUATION ***
      IF(IAX.EQ.8.AND.IFUN.LE.4) GO TO 3000
C*** CHECK FOR COUPLANT VELOCITY ***
      IF(MODE.EQ.1.AND.IFUN.EQ.7.AND.IAX.EQ.2) GO TO 4000
C*** CHECK FOR GEOMETRY CALCULATION ***
      IF(MODE.EQ.1.AND.IFUN.EQ.7.AND.IAX.EQ.3) GO TO 5000
      GO TO 100
C*** SET MULTIPLEXER CHANNEL ***
1000  C=FLOAT(IAX)
      CALL MUX(C)
      GO TO 100
C*** DELAY ***
2000  D=U(3)+IDIR*DINC(IFUN)
      IF(D.LT.DMIN) D=DMIN
      IF(D.GT.DMAX) D=DMAX
      CALL DELAY (D)
      GO TO 100
C*** ATTENUATION ***
3000  A=U(2)+IDIR*AINC(IFUN)
      IF(A.LT.AMIN) A=AMIN
      IF(A.GT.AMAX) A=AMAX
      CALL ATTN(A)
      GO TO 100
C*** GET COUPLANT VELOCITY IF IDIR = +1 ***
4000  IF(IDIR.EQ.1) CALL CPLVEL
      GO TO 100
C*** CALCULATE GEOMETRY ***
5000  CALL CALGEO(AI,PL,DE,DC,I1)
C*** CALCULATE REFRACTED ANGLES FOR SHEAR AND LONGITUDINAL ***
      CALL SNELL(AI,AR(1),CVEL,SSV(1),IERR(1))
      CALL SNELL(AI,AR(2),CVEL,SSV(2),IERR(2))
```

USEBOX.FTN;21                    SPOOL DATE: 09-FEB-81

```
              IF(IDIR.EQ.1) GO TO 4100
C*** LONG PRINTOUT ***
              IF(I1.NE.0) WRITE(5,1) I1
1             FORMAT(' ERROR CODE:',I5)
              WRITE(5,2) AI,PL,DE,DC
2             FORMAT(' INC ANG:',T12,F6.2,/,
             .       ' PTH LEN:',T12,F8.4,/,' EDG DIS:',T12,F8.4,/,
             .       ' CEN DIS:',T12,F8.4)
4050          IF(IERR(1).EQ.0) WRITE(5,3) AR(1)
3             FORMAT(' REF(SH):',T12,F6.2)
              IF(IERR(1).NE.0) WRITE(5,4)
4             FORMAT(' REF(SH):',T12,'PAST CRITICAL')
              IF(IERR(2).EQ.0) WRITE(5,5) AR(2)
5             FORMAT(' REF(LO):',T12,F6.2)
              IF(IERR(2).NE.0) WRITE(5,6)
6             FORMAT(' REF(LO):',T12,'PAST CRITICAL')
              WRITE(5,7)
7             FORMAT(///)
              GO TO 100
C*** SHORT PRINTOUT - ANGLES ONLY ***
4100          IF(I1.NE.0) WRITE(5,1) I1
              WRITE(5,8) AI
8             FORMAT(' INC:',T12,F6.2)
              GO TO 4050
C*** RETURN ***
10000         CALL USMPOS
              CALL UTSTAT
              RETURN
              END
```

USMMSK.FTN;1                    SPOOL DATE: 09-FEB-81

```
C*** SUBROUTINE USMMSK.FTN ***
C*** J. E. HORN ***
C*** 11/9/79 ***
C*** SUBROUTINE TO SET USM CONTROL BOX MASK ***
              SUBROUTINE USMMSK(M)
              DIMENSION M(6)
              COMMON /ARG/ NCMD(10),IARG(100)
C*** SET UP AND SEND COMMAND ***
              NCMD(1)=8
              DO 100 I=1,6
100              IARG(I)=M(I)
              CALL SNDCMD(1,1,IERR)
              RETURN
              END
```

USMPOS.FTN;2          SPOOL DATE: 09-FEB-81

```fortran
C*** SUBROUTNE USMPOS.FTN ****
C*** J.E. HORN ***
C*** 10/31/79 ***
C*** SUBROUTINE TO GET USM POSITION/STATUS
       SUBROUTINE USMPOS
       DIMENSION IARG(100)
       COMMON /USM/ X(6),ISTAT
       COMMON /ARG/ NCMD(10),XARG(50)
       EQUIVALENCE (XARG(1),IARG(1))
C*** SEND COMMAND TO REQUEST POSITON STATUS ***
       NCMD(1)=1
100    CALL SNDCMD(1,1,IERR)
C*** WAIT FOR POSITION/STATUS ***
150    CALL CMDINP (1,IFLG,IERR)
       IF(IERR.NE.0) GO TO 100
       IF(IFLG.EQ.0) GO TO 150
C*** DECODE COMMAND ***
       CALL CMDDEC (1,IERR)
       IF(NCMD(1).NE.1.OR.IERR.NE.0) GO TO 100
C*** UPDATE COMMON AREA ***
       DO 200 I=1,6
200       X(I)=XARG(I)
       ISTAT=IARG(13)
       RETURN
       END
```

UTMSK.FTN;3          SPOOL DATE: 09-FEB-81

```fortran
C*** SUBROUTINE UTMSK.FTN ***
C*** J. E. HORN ***
C*** 11/9/79 ***
C*** SUBROUTINE TO SET UT FUNTION MASK ***
       SUBROUTINE UTMSK(M)
       DIMENSION M(3)
       COMMON /ARG/ NCMD(10),IARG(100)
C*** SET UP AND SEND COMMAND ***
       NCMD(1)=5
       DO 100 I=1,3
100       IARG(I)=M(I)
       CALL SNDCMD(1,2,IERR)
       RETURN
       END
```

UTPLOT.FTN;2                    SPOOL DATE: 09-FEB-81

```
C*** SUBROUTINE UTPLOT.FTN ***
C*** J. E. HORN ***
C*** 11/6/79 ***
C*** SUBROUTINE TO PLOT WAVEFORM ON UT SYSTEM ***
        SUBROUTINE UTPLOT (R,H)
        DIMENSION R(2),H(8)
        COMMON /USM/ X(6)
        COMMON /ARG/ NCMD(10),XARG(50)
C*** SEND COMMAND TO PLOT WITH HEADER INFORMATION ***
        NCMD(1)=9
        XARG(1)=R(1)
        XARG(2)=R(2)
        DO 100 I=1,6
100       XARG(I+2)=X(I)
        DO 200 I=1,8
200       XARG(I+8)=H(I)
        CALL SNDCMD (1,2,IERR)
        RETURN
        END
```

UTSTAT.FTN;1                    SPOOL DATE: 09-FEB-81

```
C*** SUBROUTINE UTSTAT.FTN ***
C*** J. E. HORN ***
C*** 11/6/79 ***
C*** SUBROUTINE TO GET UT SYSTEM STATUS ***
        SUBROUTINE UTSTAT
        COMMON /UT/ U(5)
        COMMON /ARG/ NCMD(10),XARG(50)
C*** SEND COMMAND TO REQUEST STATUS ***
100     NCMD(1)=1
        CALL SNDCMD(1,2,IERR)
C*** WAIT FOR STATUS ***
200     CALL CMDINP(2,IFLG,IERR)
        IF(IERR.NE.0)GO TO 100
        IF(IFLG.EQ.0) GO TO 200
C*** DECODE COMMAND ***
        CALL CMDDEC(2,IERR)
        IF(NCMD(1).NE.1.OR.IERR.NE.0) GO TO 100
C*** UPDATE COMMON AREA ***
        DO 300 I=1,5
300       U(I)=XARG(I)
        RETURN
        END
```

VELCAL.FTN;12　　　　　　　　　　　　　SPOOL DATE: 09-FEB-81

```fortran
C*** SUBROUTINE VELCAL.FTN ***
C*** J.E. HORN ***
C*** 4/4/80 ***
C*** SUBROUTINE TO CALIBRATE VELOCITY SENSING TRANSDUCER ***
      SUBROUTINE VELCAL (VL)
      COMMON /USM/ X(6)
      COMMON /UT/ U(5)
      COMMON /VELPAR/ VEL,VSDIST,SSVEL(2)
      DATA DEL3 /0.12/,NT/10/
C*** ASSUMES USM SET UP NORMAL TO SURFACE ***
C*** GET TIME AND SET UP DELAY SO SIGNAL IS CENTERED ***
      CALL MUX(2.0)
      CALL CENSIG(IERR)
C*** MOVE TOWARD PIPE ***
      CALL USMPOS
      XSTRT=X(3)
      XX=X(3)-DEL3/2.0
      CALL SERVO (XX,3)
      X1=X(3)
C*** AVERAGE TIME NT TIMES ***
      CALL TIMAVG(T1,NT)
C*** MOVE AWAY FROM PIPE ***
      XX=X(3)+DEL3
      CALL SERVO (XX,3)
      X2=X(3)
C*** AVERAGE TIME NT TIMES ***
      CALL TIMAVG(T2,NT)
C*** MOVE BACK TO STARTING POSITION ***
      CALL SERVO (XSTRT,3)
C*** CALCULATE VELOCITY ***
      DX=(X2-X1)*2.0
      DT=T2-T1
      VL=DX/DT
C*** SWITCH TO CHANNEL 1 AND MEASURE TIME ***
      CALL MUX(1.0)
      CALL FNDSIG(IERR)
      CALL TIMAVG(T3,NT)
C*** CALCULATE CORRESPONDING DISTANCE ***
      VSDIST=VL*T3*0.5
      CALL MUX(2.0)
      RETURN
      END
```

VOLT.FTN;3                    SPOOL DATE: 09-FEB-81

```fortran
C*** SUBROUTINE VOLT.FTN ***
C*** J. E. HORN ***
C*** 4/17/80 ***
C*** SUBROUTINE TO GET ULTRASONIC VOLTAGE ***
C*** UNITS ARE IN PERCENT OF FULL SCALE ***
        SUBROUTINE VOLT(V1,V2)
        DIMENSION XX(2),VP(3),VM(3)
        IMXP=1
        IMNP=1
        IMXM=1
        IMNM=1
C*** TAKE 3 MEASUREMENTS - FIND MAX AND MIN FOR PLUS AND MINUS ***
        DO 100 I=1,3
           CALL BIORCV(1,XX)
           VP(I)=XX(1)
           VM(I)=XX(2)
           IF(VP(I).GT.VP(IMXP)) IMXP=I
           IF(VP(I).LT.VP(IMNP)) IMNP=I
           IF(VM(I).GT.VM(IMXM)) IMXM=I
           IF(VM(I).LT.VM(IMNM)) IMNM=I
100     CONTINUE
C*** FIND MEDIAN FOR PLUS AND MINUS ***
        DO 200 I=1,3
           IF(I.NE.IMXP.AND.I.NE.IMNP) IMDP=I
           IF(I.NE.IMXM.AND.I.NE.IMNM) IMDM=I
200     CONTINUE
        V1=VP(IMDP)
        V2=VM(IMDM)
        RETURN
        END
```

```
C*** SUBROUTINE WLDCEN.FTN ***
C*** J. E. HORN ***
C*** 4/21/80 ***
C*** SUBROUTINE TO FIND CENTER OF WELD BEAD ALONG AXIS 2 ***
C*** AXES 4 AND 5 ARE PEAKED AND AXIS 3 IS MOVED TO PRDIST ***
        SUBROUTINE WLDCEN(DEL2,X2INC,IERR)
        DIMENSION X2END(2),XWB2(2),XPR3(2),XPK4(2),XPK5(2)
        COMMON /PRFCEN/ ICEN,X4REF,X5REF,X3CF(2),XCEN
        COMMON /USM/ X(6)
        COMMON /UT/ U(5)
        DATA FR/0.5/,MODE/0/
C*** GET CURRENT POSITION ***
        CALL USMPOS
C*** SET MUX TO PROFILE CHANNEL (2) ***
        CALL MUX(2.0)
C*** INITIALIZE SCAN PARAMETERS ***
        XCEN=X(2)
        IERR=0
C*** GO THROUGH ALIGNMENT PROCEDURE ON BOTH SIDES OF WELD ***
        DO 100 I=1,2
           IDIR=I*2-3
           DX2=DEL2*IDIR
C*** MOVE AXIS 2 TO SELECTED SIDE OF WELD ***
           X2=XCEN+DX2
           CALL SERVO(X2,2)
C*** CHECK PANIC ***
           CALL PANIC(IPNC)
           IF(IPNC.NE.0) GO TO 10500
C*** FIND SIGNAL ***
           CALL FNDSIG(IERR)
           IF(IERR.NE.0) GO TO 10000
C*** PEAK AXES 4 AND 5 ***
           CALL PEAK(4,IERR)
           IF(IERR.NE.0) GO TO 10100
           CALL PEAK(5,IERR)
           IF(IERR.NE.0) GO TO 10200
C*** REMEMBER PEAK VALUES ***
           XPK4(I)=X(4)
           XPK5(I)=X(5)
C*** SERVO AXIS 3 TO PROFILE DISTANCE AND REMEMBER IT ***
           CALL SVOPRO(XPR3(I),IERR)
           IF(IERR.NE.0) GO TO 10300
100     CONTINUE
C*** TAKE AVERAGE OF 4 AND 5 ***
        X4REF=(XPK4(1)+XPK4(2))/2.0
        X5REF=(XPK5(1)+XPK5(2))/2.0
        CALL SERVO(X4REF,4)
        CALL SERVO(X5REF,5)
C*** MOVE TO BOTH SIDES AND SERVO PROFILE AGAIN ***
        DO 200 I=2,1,-1
           IDIR=I*2-3
           DX2=DEL2*IDIR
           X2=XCEN+DX2
           CALL SERVO(X2,2)
C*** CHECK PANIC ***
           CALL PANIC(IPNC)
           IF(IPNC.NE.0) GO TO 10500
           X2END(I)=X(2)
C*** MOVE AXIS 3 AND SERVO TO PRDIST ***
```

WLDCEN.FTN;26　　　　　　　　　　SPOOL DATE: 09-FEB-81

```
            CALL SERVO(XPR3(I),3)
            CALL SVOPRO(XPR3(I),IERR)
            IF(IERR.NE.0) GO TO 10300
200     CONTINUE
C*** CALCULATE X3 COEFS (DELTA 3/DELTA 2) ***
            DX2=X2END(2)-X2END(1)
            DX3=XPR3(2)-XPR3(1)
            X3CF(2)=DX3/DX2
            X3CF(1)=XPR3(1)-X3CF(2)*X2END(1)
C*** COEFFICIENTS FOUND - SET COMPLETION FLAG ***
            ICEN=1
C*** WRITE OUT INFO ***
            WRITE(5,1) U(2),U(3),X4REF,X5REF,X3CF
1           FORMAT(' ATTENUATION:',T20,F8.0,/,' DELAY:',T20,F8.1,/,
        .   ' AXIS 4 POSITION:',T20,F8.3,/,' AXIS 5 POSITION:',T20,F8.3,/,
        .   ' X3 COEFFICIENTS:',T20,2F8.5)
C*** START LOOP TO FIND EDGES OF WELD BEAD ***
            DO 300 I=1,2
                IDIR=I*2-3
                DX2=(DEL2*FR)*IDIR
C*** MOVE CLOSER TO WELD CENTER AND MOVE TO AXIS 3 POSITION ***
                X2=XCEN+DX2
                CALL SERVO(X2,2)
C*** CHECK PANIC ***
                CALL PANIC(IPNC)
                IF(IPNC.NE.0) GO TO 10500
                X3=X3CF(1)+X3CF(2)*X2
                CALL SERVO(X3,3)
C*** MAP WELD BEAD CURVATURE ***
                DX2=-X2INC*IDIR
                CALL MAPWLD(MODE,DX2,XWB2(I),IERR)
                IF(IERR.NE.0) GO TO 10400
300     CONTINUE
C*** CALCULATE CENTER **
            XCEN=(XWB2(1)+XWB2(2))/2.0
            WRITE(5,6) XCEN,X(1)
6           FORMAT(' X2 CENTER =',F8.4,' AT X1 =',F8.3)
            RETURN
C*** ERROR CONDITIONS ***
10000   IERR=1
            WRITE(5,2) X(2)
2           FORMAT(' ERROR IN FINDING SIGNAL AT X(2) =',F8.3)
            GO TO 20000
10100   IAX=4
10150   IERR=2
            WRITE(5,3) IAX,X(2)
3           FORMAT(' ERROR IN PEAKING AXIS',I3,' AT X(2) =',F8.3)
            GO TO 20000
10200   IAX=5
            GO TO 10150
10300   IERR=3
            WRITE(5,4) X(2)
4           FORMAT(' ERROR IN SVOPRO AT X(2) =',F8.3)
            GO TO 20000
10400   WRITE(5,5) X(2)
5           FORMAT(' ERROR IN MAPWLD AT X(2) =',F8.3)
            GO TO 20000
C*** PANIC ERROR ***
10500   IERR=4
```

WLDCEN.FTN;26                    SPOOL DATE: 09-FEB-81

```
        WRITE(5,7)
7       FORMAT(' PANIC ERROR')
        GO TO 20100
C*** MOVE BACK TO CENTER POSITION ***
20000   CALL SERVO(XCEN,2)
C*** CLEAR COMPLETION FLAG ***
20100   ICEN=0
        RETURN
        END
```

WRITWF.FTN;10                    SPOOL DATE: 09-FEB-81

```
C*** SUBROUTINE WRITWF.FTN ***
C*** J. E. HORN ***
C*** 3/6/80 ***
C*** SUBROUTINE TO WRITE INTEGER WAVEFORM OUT TO DIRECT ACCESS FILE ***
        SUBROUTINE WRITWF(IWF,ITYP,LUN,W,HD)
C*** IWF   = WAVEFORM NUMBER ***
C*** ITYP  = 0 FOR REAL WAVEFORM OF LENGTH 512 (TEK 7912) ***
C***        = 1 FOR INTEGER WAVEFORM OF LENGTH 512 (BIO 8100) ***
C***        = 2 FOR INTEGER WAVEFORM OF LENGTH 1024 (BIO 8100) ***
C*** LUN   = LOGICAL UNIT NUMBER OF OUTPUT FILE ***
C*** W     = WAVEFORM ARRAY (MAX DIMENSION=512) ***
C*** HD    = HEADER ARRAY ***
        DIMENSION W(512),HD(128)
C*** CALCULATE RECORD NUMBER ***
        NREC=5*IWF-4
        IF(ITYP.EQ.1) NREC=3*IWF-2
C*** WRITE OUT HEADER ***
        WRITE(LUN'NREC)HD
C***WRITE OUT WAVEFORM ***
        WRITE(LUN'NREC+1) (W(K),K=1,128)
        WRITE(LUN'NREC+2) (W(K),K=129,256)
        IF(ITYP.EQ.1) RETURN
        WRITE(LUN'NREC+3) (W(K),K=257,384)
        WRITE(LUN'NREC+4) (W(K),K=385,512)
        RETURN
        END
```

CALGEO.FTN;1                     SPOOL DATE: 09-FEB-81

COMPAR.FTN;24                    SPOOL DATE: 09-FEB-81

```fortran
C*** BLOCK DATA COMPAR.FTN ***
C*** J. E. HORN ***
C*** 11/1/79 ***
C*** BLOCK COMMON TO INITIALIZE CENTRAL COMPUTER COMMON AREAS ***
      BLOCK DATA
      COMMON /USM/ X(6),ISTAT
      COMMON /UT/ U(5)
      COMMON /VELPAR/ CVEL,VSDIST,SSVEL(2)
      COMMON /PRFPAR/ PRDIST,DELANG,DI(2),DPIV,X3PIV
      COMMON /PRFCEN/ ICEN,X4REF,X5REF,X3CF(2),XCEN
      COMMON /PRFDAT/ NP,ISIDE,X2EP(2),X2(100),D(100)
      COMMON /PRFFIT/ PCF(3)
      COMMON /SECDAT/ NSIDE,X1(3),X4(3),X5(3),COEF(2,3),X2CEN(3),
     . V(3),X2END(2,3),PARCF(3,3)
      COMMON /EDGDAT/ NPEDG,X1PAR(2),X2INC,FV(2),X2EDG(256)
      COMMON /EDGFIT/ ECF(3)
      COMMON /GEOPAR/ ITYP,AREF,PLEN,DEDG
      COMMON /MASK/ MSKUSM(6),MSKUT(3),MSKTRM
      COMMON /WF/ IW(1024),RINDX(2),IWF
      COMMON /HDR/ HD(128)
      COMMON /FNAME/ NC,NAME(16)
      COMMON /SND/ IC1(2),IP1(2),ICD1(128,2),MX1(2),L1(20,2),NS1(2)
      COMMON /RCV/ IC2(2),IP2(2),ICD2(128,2),MX2(2),L2(20,2),NS2(2)
      COMMON /ARG/ NCMD(10),IARG(100)
      COMMON /LNKTSK/ LNKCMD,LNKARG(5),LNKFLG(2)
      COMMON /CSIEF/ NFLG(2)
      COMMON /CSICOM/ ICMD,ISWT,NARG,CARG(10),IFLG(10),MSKCMD(50),MARG
C*** INITIALIZE VELOCITY PARAMETERS ***
      DATA CVEL/0.046/,VSDIST/1.53/,SSVEL/0.122835,0.222441/
C*** INITIALIZE PROFILE PARAMETERS ***
      DATA PRDIST/0.915/,DELANG/14.15/,DI/0.915,1.025/
      DATA DPIV/2.27/,X3PIV/0.0137/
C*** SET ICEN=0 TO INDICATE NO CENTERING HAS BEEN DONE ***
      DATA ICEN/0/
C*** INITIALIZE GEOMETRY PARAMETERS ***
      DATA ITYP/2/,AREF/60.0/,PLEN/1.05/,DEDG/0.17/
C*** ENABLE ALL MASKS ***
      DATA MSKUSM/6*1/,MSKUT/3*1/,MSKTRM/1/
C*** INITIALIZE WAVEFORM INDECES AND HEADER ***
      DATA RINDX/2*1.0/,HD/128*0.0/,IWF/0/
C*** LET DEFAULT FILENAME BE NULL DEVICE ***
      DATA NAME/'NL',': ',14*'   '/,NC/3/
C*** INITIALIZE LINK ADDRESSES ***
      DATA IC1/1,2/,IC2/1,2/
C*** INITIALIZE MAX COMMAND AND COMMAND LENGTHS FOR SND ***
      DATA MX1/13,11/,L1/0,12,6,0,0,13,1,6,3,3,1,1,3,7*0,
     . 0,2,2,2,3,4,2,0,32,0,0,9*0/
C*** INITIALIZE MAX COMMAND AND COMMAND LENGTHS FOR RCV ***
      DATA MX2/3,3/,L2/13,4,2,17*0,10,0,6,17*0/
C*** INITIALIZE FIFO LENGTHS ***
      DATA NS1/64,64/,NS2/64,64/
C*** INITIALIZE EVENT FLAGS FOR INTERTASK COMMUNICATION ***
      DATA LNKFLG/40,41/
C*** INITIALIZE EVENT FLAGS FOR CSI TASK ***
      DATA NFLG/42,43/
C*** DISABLE NULL COMMAND AND ENABLE ALL OTHERS ***
      DATA MARG/-1/,MSKCMD/50*1/
      END
```

CSIDAT.FTN;67                    SPOOL DATE: 09-FEB-81

```
C*** BLOCK DATA CSIDAT.FTN ***
C*** B. K. JENTZEN ***
C*** 1/7/80 ***
C*** COMMAND SET FOR CSITSK (USE TASK) ***
        BLOCK DATA
        COMMON/COMAND/COMM(50),IMAX,ISWTCH(2,200),NLINK(2,50)
C*** SET MAXIMUM COMMAND CODE VALUE ***
        DATA IMAX/29/
C*** SET COMMAND MNEMONICS ***
        DATA COMM /'ATT','BOX','DEL','DIG','DIS',
       .           'ENA','ESW','MOV','MUX','PLO','STA',
       .           'STO','SWE','BIO','PRE','HEL','SCA',
       .           'FIL','VEL','PEA','PRO','SIG','WEL',
       .           'SEC','PAU','EDG','DAT','GEO','PSC',21*0.0/
C*** SET SWITCH CODES AND NUMBER OF ARGUMENTS ***
        DATA ISWTCH/' ',1,'AU',0,
       .          ' ',0,'1',0,'2',0,'PR',0,
       .          ' ',1,'CE',0,
       .          ' ',0,'PL',0,'ST',0,
       .          'AL',0,'1',0,'2',0,'3',0,'4',0,'5',0,'6',0,'MU',0,
       1          'AT',0,'DE',0,'TE',0,'US',0,'UT',0,
       .          'AL',0,'1',0,'2',0,'3',0,'4',0,'5',0,'6',0,'MU',0,
       1          'AT',0,'DE',0,'TE',0,'US',0,'UT',0,
       .          ' ',0,
       .          'AL',6,'1',1,'2',1,'3',1,'4',1,'5',1,'6',1,
       .          ' ',-1,'1',0,'2',0,'3',0,
       .          ' ',0,
       .          ' ',0,
       .          ' ',0,
       .          ' ',-1,'1',3,'2',3,'3',3,'4',3,'5',3,'6',3,
       .          ' ',-1,'VS',1,'TS',1,'TR',1,'WI',1,'LO',0,'UN',0,'DI',0,
       1          'DX',0,'VO',0,'TI',0,'TW',0,
       .          ' ',-1,'1',1,'2',1,'3',1,'4',1,'5',1,'6',1,'AL',6,
       .          'TT',0,'LP',0,
       .          ' ',-1,'LI',3,'VO',5,
       .          'WF',0,'CL',0,
       .          ' ',0,'CA',0,'DI',0,'SS',2,
       .          ' ',-1,'1',0,'2',0,'3',0,'4',0,'5',0,'6',0,
       .          'DI',0,'DD',1,'MD',0,'SV',0,'PI',2,
       .          ' ',0,'CE',0,'FI',0,
       .          ' ',-1,'CE',2,'PR',1,'FI',0,'DU',0,
       .          ' ',-1,'1',2,'2',2,
       .          ' ',0,
       .          ' ',-1,'PR',5,'FI',0,
       .          'DU',0,'ST',0,'RE',0,
       .          ' ',0,'IN',1,'RE',1,'CA',0,'MO',0,'SE',4,
       .          ' ',-1,'LI',3,'VO',4,142*0/
C*** SET SWITCH POINTERS AND NUMBER OF SWITCHES FOR EACH COMMAND ***
        DATA NLINK /1,2,3,4,7,2,9,3,12,13,25,13,38,1,39,7,46,4,50,1,
       .          51,1,52,1,53,7,60,12,72,8,80,2,82,3,85,2,87,4,91,7,
       .          98,5,103,3,106,5,111,3,114,1,115,3,118,3,121,6,127,3,42*0/
        END
```

CSITSK.FTN;3                    SPOOL DATE: 09-FEB-81

```
C*** PROGRAM CSITSK.FTN ***
C*** J. E. HORN ***
C*** 6/11/80 ***
C*** PROGRAM TO GET CSI COMMANDS ***
        COMMON /CSIEF/ NFLG(2)
        COMMON /CSICOM/ ICMD,ISWT,NARG,CARG(10),IFLG(10),MSKCMD(50),MARG
        DATA IHEL/16/,IPAU/25/
C*** CLEAR FLAG 2 ON STARTUP ***
        CALL CLREF(NFLG(2))
C*** WAIT FOR FLAG 1 THEN CLEAR ***
100     CALL WAITFR(NFLG(1))
        CALL CLREF(NFLG(1))
C*** CALL CSI AND GET COMMAND ***
200     CALL CSI
C*** EXECUTE IF HELP OR PAUSE ***
        IF(ICMD.NE.IHEL.AND.ICMD.NE.IPAU) GO TO 300
        IF(ICMD.EQ.IHEL) CALL HELCMD
        IF(ICMD.EQ.IPAU) CALL PAUCMD
        GO TO 200
C*** SET FLAG 2 AND DECLARE SIGNIFICANT EVENT ***
300     CALL SETEF(NFLG(2))
        CALL DECLAR
C*** SEE IF TERMINATION COMMAND ***
        IF(ICMD.NE.-1) GO TO 100
C*** PRINT MESSAGE AND STOP ***
        WRITE(5,1)
1       FORMAT(' *** CSI TERMINATING ***')
        CALL EXIT
        END
```

DIS.FTN;50                         SPOOL DATE: 09-FEB-81

```fortran
C*** PROGRAM DIS.FTN ***
C*** J.E.HOFN ***
C*** 2/6/80 ***
C*** REV 3/21/80 JEH - SPLIT INTO SUBROUTINES ***
C*** PROGRAM TO DISPLAY WAVEFORMS ***
            BYTE NAME
            COMMON /CSICOM/ ICMD,ISWT,NARG,CARG(10),IFLG(10),MSKCSI(50),MARG
            COMMON /FNAME/ NC,NAME(32)
            COMMON /HDR/ HD(128)
            COMMON /WF/ W(1024),IPTS
            COMMON /WNDW/ IXLL,IYLL,IXUR,IYUR
            COMMON /DISCOM/ PSF,NWF,ITYP,HS,ICOM,ICOP
            COMMON /PKVL/ PV(500),IWF1,IWF2,INC
            DATA PSF/0.5/,NWF/0/,ITYP/2/,ICOM/4/,HS/1.024/,ICOP/0/,IPTS/1024/
            DATA IXLL,IYLL,IXUR,IYUR/100,100,900,700/
            CALL ASSIGN (4,'TTO:')
C*** GET COMMAND FROM CSI ***
100         CALL CSI
            IF(ICMD.EQ.-1) CALL EXIT
            GO TO (1000,2000,3000,4000,5000,6000,7000,8000,9000,
           .   10000,11000,12000,13000,14000)ICMD
C*** #1 - FIL (ASSIGN FILE) ***
1000        CALL DIS01
            GO TO 100
C*** #2 - MAX (FIND MAX OF WAVEFORM IN BUFFER ) ***
2000        CALL DIS02
            GO TO 100
C*** #3 - PLO (PLOT WAVEFORM OR PROFILE DATA) ***
3000        CALL DIS03
            GO TO 100
C*** #4 - PSF (PLOT SCALE FACTOR) ***
4000        CALL DIS04
            GO TO 100
C*** #5 - REA (READ WAVEFORM) ***
5000        CALL DIS05
            GO TO 100
C*** #6 - HEL (HELP COMMAND) ***
6000        CALL DIS06
            GO TO 100
C*** #7 - TYP (SET WAVEFORM TYPE) ***
7000        CALL DIS07
            GO TO 100
C*** #8 - ISO (ISOPLOT) ***
8000        CALL DIS08
            GO TO 100
C*** #9 - PPV (PLOT PEAK VOLTAGE) ***
9000        CALL DIS09
            GO TO 100
C*** #10 - SPE (PLOT POWER/FREQUENCY SPECTRUM) ***
10000       CALL DIS10
            GO TO 100
C*** #11 - COM (CHANGE FFT COMPRESSION) ***
11000       CALL DIS11
            GO TO 100
C*** #12 - MUL (MULTIPLE WAVEFORM PLOTS) ***
12000       CALL DIS12
            GO TO 100
C*** #13 - WIN (SET GRAPHICS WINDOW) ***
13000       CALL DIS13
            GO TO 100
C*** #14 - COP (SET HARD COPY MODE) ***
14000       CALL DIS14
            GO TO 100
            END
```

LINK.FTN;1                SPOOL DATE: 09-FEB-81

```
C*** PROGRAM LINK.FTN ***
C*** J. E. HORN ***
C*** 5/27/80 ***
C*** PROGRAM TO SEND/RECEIVE COMMANDS OVER COMMUNICATIONS LINK VIA
C*** SIGNIFICANT EVENTS ***
      COMMON /LNKTSK/ LNKCMD,LNKARG(5),LNKFLG(2)
C*** CLEAR FLAG 2 ***
      CALL CLREF(LNKFLG(2))
C*** GET LINK COMMAND ***
100   CALL GETCMD
C*** IGNORE INVALID COMMAND ***
      IF(LNKCMD.LT.1.OR.LNKCMD.GT.4) GO TO 100
C*** EXECUTE COMMAND ***
      GO TO (1000,2000,3000,4000) LNKCMD
C*** #1 - COMMAND INPUT ***
1000  CALL LNK01
      GO TO 10000
C*** #2 - SEND COMMAND ***
2000  CALL LNK02
      GO TO 10000
C*** #3 - RECEIVE WAVEFORM ***
3000  CALL LNK03
      GO TO 10000
C*** #4 - CHECK LINK ***
4000  CALL LNK04
C*** DECLARE COMMAND FINISHED ***
10000 CALL FINCMD
      GO TO 100
      END
```

```
USE.FTN;40                    SPOOL DATE: 09-FEB-81

C*** PROGRAM USE.FTN ***
C*** J. E. HORN **
C*** 3/6/80 ***
C*** PROGRAM TO OPERATE ULTRASONIC SCANNING EQUIPMENT ***
        COMMON /CSICOM/ ICMD,ISWT,NARG,CARG(10),IFLG(10),MSKCMD(50),MARG
        COMMON /FNAME/ NC,NAME(16)
        COMMON /LNKTSK/ LNKCMD,LNKARG(5),LNKFLG(2)
        COMMON /CSIEF/ NFLG(2)
C*** CLEAR LINK EVENT FLAGS 1 AND 2 ***
        CALL CLREF(LNKFLG(1))
        CALL CLREF(LNKFLG(2))
C*** CLEAR CSI EVENT FLAGS 1 AND 2 ***
        CALL CLREF(NFLG(1))
        CALL CLREF(NFLG(2))
C*** CHECK IF COMMUNICATION LINKS ACTIVE ***
        CALL CHKLNK(1,I1)
        CALL CHKLNK(2,I2)
        IF(I1.EQ.1.AND.I2.EQ.1) GO TO 100
C*** BOTH LINKS NOT ACTIVE - SEE IF WANT TO PROCEED ***
        WRITE(5,1)I1,I2
1       FORMAT(' COMMUNICATION LINK STATUS:',/,
       .  ' 1:ACTIVE, 0:INACTIVE, -1:CAN''T CLEAR',/,
       .  ' LINK #1 STATUS: ',I5,5X,'LINK #2 STATUS: ',I5,/,
       .  '$DO YOU WANT TO PROCEED?')
        CALL ANSWR (IANS)
        IF(IANS.EQ.0) CALL EXIT
C*** ASSIGN NULL DEVICE AS FILE #1 ***
100     CALL ASSIGN (1,NAME,3)
        DEFINE FILE 1(5000,256,U,NR1)
C*** GET COMMAND FROM COMMAND STRING INTERPRETER ***
500     CALL CSI
C*** SEE IF TERMINATION COMMAND ***
        IF(ICMD.EQ.-1) CALL EXIUSE
C*** EXECUTE COMMAND ***
        GO TO (1000,2000,3000,4000,5000,6000,7000,8000,9000,10000,
       .  11000,12000,13000,14000,15000,500,17000,18000,19000,20000,
       .  21000,22000,23000,24000,500,26000,27000,28000,29000) ICMD
C*** #1 - ATT (ATTENUATION) ***
1000    CALL USE01
        GO TO 500
C*** #2 - BOX (CONTROL BOX) ***
2000    CALL USE02
        GO TO 500
C*** #3 - DEL (DELAY) ***
3000    CALL USE03
        GO TO 500
C*** #4 - DIG (DIGITIZE) ***
4000    CALL USE04
        GO TO 500
C*** #5 - DIS (DISABLE MASKS) ***
5000    CALL USE05
        GO TO 500
C*** #6 - ENA (ENABLE MASKS) ***
6000    CALL USE06
        GO TO 500
C*** #7 - ESW(END SWEEP) ***
7000    CALL USE07
        GO TO 500
C*** #8 - MOV(MOVE USM) ***
```

USE.FTN;40                    SPOOL DATE: 09-FEB-81

```
8000    CALL USE08
        GO TO 500
C*** #9 - MUX (SET MULTIPLEXER CHANNEL) ***
9000    CALL USE09
        GO TO 500
C*** #10 - PLO (PLOT WAVEFORM ON UT COMPUTER) ***
10000   CALL USE10
        GO TO 500
C*** #11 - STA (USM POSITION AND UT STATUS) ***
11000   CALL USE11
        GO TO 500
C*** #12 - STO (STORE WAVEFORM) ***
12000   CALL USE12
        GO TO 500
C*** #13 - SWE (SWEEP) ***
13000   CALL USE13
        GO TO 500
C*** #14 - BIO (SET/READ BIOMATION PARAMETERS) ***
14000   CALL USE14
        GO TO 500
C*** #15 - PRE (PRESET POSITION REGISTERS) ***
15000   CALL USE15
        GO TO 500
C*** #17 - SCA (LINE SCAN WITH ANY AXIS) ***
17000   CALL USE17
        GO TO 500
C*** #18 - FIL (CLOSE AND REASSIGN OUTPUT FILE) ***
18000   CALL USE18
        GO TO 500
C*** #19 - VEL (GET/CALIBRATE VELOCITY) ***
19000   CALL USE19
        GO TO 500
C*** #20 - PEA (PEAK ULTRASONIC SIGNAL) ***
20000   CALL USE20
        GO TO 500
C*** #21 - PRO (EXECUTE PROFILE FUNCTIONS) ***
21000   CALL USE21
        GO TO 500
C*** #22 - SIG (MEASURE, CENTER, AND FIND SIGNAL) ***
22000   CALL USE22
        GO TO 500
C*** #23 - WEL (PROFILE AND FIND CENTER OF WELD BEAD) ***
23000   CALL USE23
        GO TO 500
C*** #24 - SEC (PROFILE SECTOR) ***
24000   CALL USE24
        GO TO 500
C*** #26 - EDG (PROFILE WELD BEAD EDGE AND FIT DATA) ***
26000   CALL USE26
        GO TO 500
C*** #27 - DAT (DUMP, STORE, AND READ PROFILE DATA) ***
27000   CALL USE27
        GO TO 500
C*** #28 - GEO (PERFORM REFRACTED ANGLE GEOMETRY CALCULATIONS) ***
28000   CALL USE28
        GO TO 500
C*** #29 - PSC (PROFILE SCAN - LINE OR VOLUMETRIC) ***
29000   CALL USE29
        GO TO 500
        END
```

USECOM.FTN;35          SPOOL DATE: 09-FEB-81

```
C*** BLOCK DATA USECOM.FTN ***
C*** J. E. HORN ***
C*** 11/1/79 ***
C*** BLOCK COMMON TO INITIALIZE CENTRAL COMPUTER COMMON AREAS ***
      BLOCK DATA
      COMMON /USM/ X(6),ISTAT
      COMMON /UT/ U(5)
      COMMON /VELPAR/ CVEL,VSDIST,SSVEL(2)
      COMMON /PRFPAR/ PRDIST,DELANG,DI(2),DPIV,X3PIV
      COMMON /PRFCEN/ X4REF,X5REF,X3CF(2),XCEN
      COMMON /PRFDAT/ NP,ISIDE,X2EP(2),X2(100),D(100)
      COMMON /PRFFIT/ A(3)
      COMMON /SECDAT/ NSIDE,X1(3),X4(3),X5(3),COEF(2,3),X2CEN(3),
     . V(3),X2END(2,3),PARCF(3,3)
      COMMON /EDGDAT/ NPEDG,X1PAR(2),X2INC,FV(2),X2EDG(128)
      COMMON /MASK/ MSKUSM(6),MSKUT(3),MSKTRM
      COMMON /WF/ IW(512),RINDX(2),IWF
      COMMON /HDR/ HD(128)
      COMMON /SND/ IC1(2),IP1(2),ICD1(128,2),MX1(2),L1(20,2),NS1(2)
      COMMON /RCV/ IC2(2),IP2(2),ICD2(128,2),MX2(2),L2(20,2),NS2(2)
C*** INITIALIZE VELOCITY PARAMETERS ***
      DATA CVEL/0.046/,VSDIST/1.53/,SSVEL/0.122835,0.222441/
C*** INITIALIZE PROFILE PARAMETERS ***
      DATA PRDIST/0.915/,DELANG/14.15/,DI/0.915,1.025/
C*** ENABLE ALL MASKS ***
      DATA MSKUSM/6*1/,MSKUT/3*1/,MSKTRM/1/
C*** INITIALIZE WAVEFORM INDECES AND HEADER ***
      DATA RINDX/2*1.0/,HD/128*0.0/,IWF/0/
C*** INITIALIZE LINK ADDRESSES ***
      DATA IC1/1,2/,IC2/1,2/
C*** INITIALIZE MAX COMMAND AND COMMAND LENGTHS FOR SND ***
      DATA MX1/12,10/,L1/0,12,6,0,0,1,1,6,3,3,1,3,8*0,
     . 0,2,2,2,3,4,2,0,32,0,10*0/
C*** INITIALIZE MAX COMMAND AND COMMAND LENGTHS FOR RCV ***
      DATA MX2/3,3/,L2/13,4,2,17*0,10,0,6,17*0/
C*** INITIALIZE FIFO LENGTHS ***
      DATA NS1/64,64/,NS2/64,64/
      END
```

UTSTOP.FTN;1          SPOOL DATE: 09-FEB-81

```
C*** PROGRAM UTSTOP.FTN ***
C*** J. E. HORN ***
C*** 6/25/80 ***
C*** PROGRAM TO STOP UTMON ON UT SYSTEM ***
      COMMON /ARG/ NCMD(10),IARG(100)
      NCMD(1)=11
      CALL SNDCMD(1,2,IERR)
      CALL EXIT
      END
```

What is claimed is:

1. An ultrasonic deployment apparatus for performing a task upon a specimen which apparatus comprises:
   (A) a scanning head having an ultrasonic profiling element and task performing means for performing a task on a specimen,
   (B) mechanical support means, for support, positioning and aligning said scanning head, and
   (C) computer means for the control of said mechanical support means, said computer means adapted to repeatably locate specific locations on said specimen using a reference system established by said computer means by observation by said profiling element of surface reference marks on a surface of said specimen.

2. An ultrasonic deployment apparatus for the inspection of specimens which comprises:
   (A) couplant supply means;
   (B) a scanning head having fluid communication with said couplant supply means, a profiling ultrasonic element for mapping the surface of the specimen, an acoustical velocity measuring ultrasonic element for measuring the velocity of sound in the couplant, at least one specimen inspection element for inspection of the specimen, and having a bellows for forming a couplant filled volume above a surface of the specimen thereby providing an acoustical communication path between the specimen and said scanning head thereby accommodating passage of ultrasonic waves therebetween;
   (C) mechanical support means for supporting, aligning and positioning said scanning head in proximity to the specimen; and
   (D) control means for said mechanical support means for controllably aligning and positioning said scanning head, which control means comprises a computer system which is programmed to control a specimen inspection traveling scan of the scanning head and moreover to automatically control the position and alignment of the scanning head in response to data obtained by previous and concurrent profiling scans to achieve and maintain desirable position and alignment of said scanning head with respect to said specimen and to use specimen surface features to identify a computer coordinate system and to use said coordinate system to identify and interpret inspection data, said computer moreover programmed to continuously interpret data received from specimen inspection scans and profiling scans using concurrently monitored couplant acoustical velocity measurements.

3. An ultrasonic deployment apparatus for the inspection of specimens which comprises:
   (A) couplant supply means;
   (B) a scanning head having fluid communication with said couplant supply means, a profiling ultrasonic element for mapping the surface of the specimen, an acoustical velocity measuring ultrasonic element for measuring the velocity of sound in the couplant, at least one specimen inspection element for inspection of the specimen, and having an outlet disposed to direct a stream of couplant to the surface of the specimen forming an acoustic communication path between the specimen and said scanning head thereby accommodating passage of ultrasonic waves therebetween;
   (C) mechanical support means for supporting, aligning and positioning said scanning head in proximity to the specimen; and
   (D) control means for said mechanical support means for controllably aligning and positioning said scanning head, which control means comprises a computer system which is programmed to control a specimen inspection traveling scan of the scanning head and moreover to automatically control the position and alignment of the scanning head in response to data obtained by previous and concurrent profiling scans to achieve and maintain desirable position and alignment of said scanning head with respect to said specimen and to use specimen surface features to identify a computer coordinate system and to use said coordinate system to identify and interpret inspection data, said computer moreover programmed to continuously interpret data received from specimen inspection scans and profiling scans using concurrently monitored couplant acoustical velocity measurements.

4. An ultrasonic deployment apparatus for the inspection of specimens which comprises:
   (A) couplant supply means;
   (B) a casing in fluid communication with said couplant supply means having an acoustical velocity measuring ultrasonic element for measuring the velocity of sound in the couplant; and
   (C) a scanning head in close proximity to and in fluid communication with said casing, said scanning head having a profiling ultrasonic element for mapping the surface of the specimen, at least one specimen inspection element for inspection of the specimen, and having a couplant containment bellows;
   (D) mechanical support means for supporting, aligning and positioning said scanning head; and
   (E) control means for said mechanical support means for controllably aligning and positioning said scanning head, which control means comprises a computer system which is programmed to control a specimen inspection traveling scan of the scanning head and moreover to automatically control the position and alignment of the scanning head in response to data obtained by previous and concurrent profiling scans to achieve and maintain desirable position and alignment of said scanning head with respect to said specimen and to use specimen surface features to identify a computer coordinate system and to use said coordinate system to identify and interpret inspection data, said computer moreover programmed to continuously interpret data received from specimen inspection scans and profiling scans using concurrently monitored couplant acoustical velocity measurements.

* * * * *